(12) United States Patent
Hatazawa et al.

(10) Patent No.: US 9,307,764 B2
(45) Date of Patent: Apr. 12, 2016

(54) PESTICIDAL DIARYL—HETEROCYCLYL DERIVATIVES

(75) Inventors: Mamoru Hatazawa, Ibaraki (JP); Tetsuya Murata, Osaka (JP); Peter Bruechner, Krefeld (DE); Daiei Yamazaki, Yamaguchi (JP); Eiichi Shimojo, Tochigi (JP); Teruyuki Ichihara, Tochigi (JP); Katsuhiko Shibuya, Tochigi (JP); Tadashi Ishikawa, Tokyo (JP)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/113,778

(22) PCT Filed: Apr. 24, 2012

(86) PCT No.: PCT/EP2012/057435
§ 371 (c)(1),
(2), (4) Date: Jan. 10, 2014

(87) PCT Pub. No.: WO2012/146572
PCT Pub. Date: Nov. 1, 2012

(65) Prior Publication Data
US 2014/0128614 A1  May 8, 2014

(30) Foreign Application Priority Data

Apr. 28, 2011 (JP) .................................. 2011-101535

(51) Int. Cl.
| | |
|---|---|
| *A01N 43/76* | (2006.01) |
| *A01N 43/82* | (2006.01) |
| *C07C 215/16* | (2006.01) |
| *C07C 233/36* | (2006.01) |
| *C07C 271/20* | (2006.01) |
| *C07C 275/24* | (2006.01) |
| *C07C 317/32* | (2006.01) |
| *C07C 317/44* | (2006.01) |
| *C07C 323/36* | (2006.01) |
| *C07C 323/60* | (2006.01) |
| *C07D 263/04* | (2006.01) |
| *C07D 291/04* | (2006.01) |
| *A01N 53/00* | (2006.01) |
| *A01N 33/04* | (2006.01) |
| *A01N 33/08* | (2006.01) |
| *A01N 37/16* | (2006.01) |
| *A01N 37/34* | (2006.01) |
| *A01N 41/12* | (2006.01) |
| *C07C 215/68* | (2006.01) |
| *C07C 215/70* | (2006.01) |
| *C07C 225/22* | (2006.01) |
| *C07C 229/42* | (2006.01) |
| *C07C 237/20* | (2006.01) |
| *C07C 255/59* | (2006.01) |
| *C07C 313/04* | (2006.01) |
| *C07C 313/12* | (2006.01) |

(52) U.S. Cl.
CPC ............... *A01N 43/76* (2013.01); *A01N 33/04* (2013.01); *A01N 33/08* (2013.01); *A01N 37/16* (2013.01); *A01N 37/34* (2013.01); *A01N 41/12* (2013.01); *A01N 43/82* (2013.01); *A01N 53/00* (2013.01); *C07C 215/16* (2013.01); *C07C 215/70* (2013.01); *C07C 225/22* (2013.01); *C07C 229/42* (2013.01); *C07C 233/36* (2013.01); *C07C 237/20* (2013.01); *C07C 255/59* (2013.01); *C07C 271/20* (2013.01); *C07C 275/24* (2013.01); *C07C 313/04* (2013.01); *C07C 313/12* (2013.01); *C07C 317/32* (2013.01); *C07C 317/44* (2013.01); *C07C 323/36* (2013.01); *C07C 323/60* (2013.01); *C07D 263/04* (2013.01); *C07D 291/04* (2013.01); *C07C 2101/02* (2013.01); *C07C 2102/08* (2013.01); *C07C 2102/10* (2013.01)

(58) Field of Classification Search
None
See application file for complete search history.

(56) References Cited

U.S. PATENT DOCUMENTS

| | | | |
|---|---|---|---|
| 8,450,483 | B2 | 5/2013 | Goergens et al. |
| 2010/0216792 | A1 | 8/2010 | Goergens et al. |
| 2011/0152332 | A1 | 6/2011 | Murata et al. |

FOREIGN PATENT DOCUMENTS

| | | |
|---|---|---|
| JP | 2008-110971 | 5/2008 |
| JP | 2008110971 A | 5/2008 |

(Continued)

OTHER PUBLICATIONS

Database Registry Chemical Abstracts Service, Columbus, Ohio, Accession No. RN 196391-45-4, Entered STN: Oct. 30, 1997.*

(Continued)

*Primary Examiner* — Samantha Shterengarts
(74) *Attorney, Agent, or Firm* — McBee, Moore, Woodward & Vanik, IP LLC

(57) ABSTRACT

To provide pesticidal allylAryl heterocycle derivatives that are useful as a pesticidal compound.
Pesticidal allylAryl heterocycle derivatives that are expressed by the Formula (I),

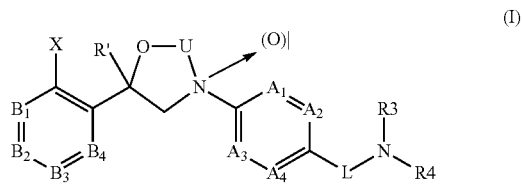

and pesticides and an agent for controlling animal parasites which include the allylAryl heterocycle derivatives as an effective component.

11 Claims, No Drawings

(56) References Cited

FOREIGN PATENT DOCUMENTS

| | | |
|---|---|---|
| JP | 2013509383 A | 3/2013 |
| WO | 2007123853 | 11/2007 |
| WO | 2007123853 A2 | 11/2007 |
| WO | 2010020522 | 2/2010 |
| WO | 2010020522 A2 | 2/2010 |
| WO | 2010043315 | 4/2010 |
| WO | 2010043315 A1 | 4/2010 |
| WO | 2011051455 | 5/2011 |

OTHER PUBLICATIONS

International Search Report dated Jun. 13, 2012, issued in counterpart International Application No. PCT/EP2012/057435.
Ghosh et al., Journal of Organic Chemistry, 2006, 71, pp. 1258-1261.
International Search Report for PCT/EP2012/057432 Mailed Jun. 13, 2012.

* cited by examiner

PESTICIDAL DIARYL—HETEROCYCLYL DERIVATIVES

CROSS REFERENCE TO RELATED APPLICATIONS

This application is a §371 National Stage Application of PCT/EP2012/057435, filed Apr. 24, 2012, which claims priority to Japanese Application No. 2011-101535, filed Apr. 28, 2011.

BACKGROUND OF THE INVENTION

1. Field of the Invention

The present invention relates to novel pesticidal allylAryl heterocycle derivatives and use thereof as pesticides.

2. Description of Related Art

In Patent Documents 1 to 4, it is described that some kinds of 5-membered heterocyclic compounds or nitrogen-containing heterocyclic compounds are useful as an agent for controlling harmful organisms.

PRIOR ART LITERATURES

WO 2007/123853, Japanese Patent Publication No. 2008-110971, WO 2010/020522, WO 2010/043315.

SUMMARY

Inventors of the present invention conducted extensive research to develop a novel compound which is highly effective as pesticides and has a broad spectrum of use. As a result, the inventors found that the novel allylAryl heterocycle derivatives represented by the following Formula (I), and N-oxide and salts thereof have a high activity, a broad spectrum of use and safety, and also are effective against harmful insects that are resistant to an organic phosphorous agent or a carbamate agent.

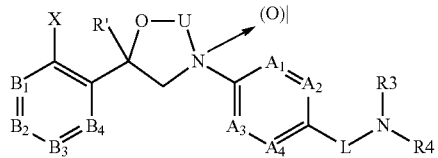

(I)

In the formula, R' represents $C_{1-12}$ alkyl or $C_{1-12}$ haloalkyl,
l represents 0 or 1,
U represents $CH_2$, S=O or $SO_2$,
$A_1$, $A_2$, $A_3$ and $A_4$ each independently represent C—Y or N, with the proviso that two of $A_1$, $A_2$, $A_3$ and $A_4$ may simultaneously represent N, or two Ys may form, together with the carbon atom to which they are bound, a benzene ring or a 5- to 6-membered heteroaromatic ring when $A_1$ and $A_2$ represent C—Y,
$B_1$, $B_2$, $B_3$ and $B_4$ each independently represent C—X or N,
L represents $(CR^1R^2)_n$,
n represents 1, 2 or 3,
$R^1$ and $R^2$ each independently represent hydrogen, cyano, $C_{1-12}$ alkyl, $C_{3-8}$ cycloalkyl, $C_{3-8}$ cycloalkyl-$C_{1-12}$ alkyl, $C_{2-6}$ alkenyl, $C_{2-6}$ alkynyl, $C_{1-12}$ alkoxy-carbonyl or $C_{1-12}$ thioalkoxy-carbonyl, and herein, each group from $C_{1-12}$ alkyl to $C_{1-12}$ thioalkoxy-carbonyl above may be optionally substituted with halogen, or $R^1$ and $R^2$ may form, together with the carbon atom to which they are bound, a 3- to 6-membered hydrocarbon ring,
or $R^1$ may form, together with Y of $A_2$, $C_{2-3}$ alkylene when n represents 1 and $A_2$ represents C—Y,
$R^3$ represents hydrogen, amino, hydroxy, cyano, $C_{1-12}$ alkyl, $C_{1-12}$ alkoxy, $C_{1-12}$ alkyl-carbonylamino, $C_{1-12}$ alkylamino, $C_{3-8}$ cycloalkyl, $C_{2-12}$ alkenyl, $C_{2-12}$ alkynyl, $C_{1-12}$ alkyl-carbonyl, —$CH_2$—$R^5$, —C(=O)$R^5$ or C(=S)$R^5$, and herein, each group from $C_{1-12}$ alkyl to $C_{1-12}$ alkyl-carbonyl above may be optionally substituted,
$R^4$ represents hydrogen, cyano, formyl, thioformyl, $C_{1-12}$ alkyl-carbonyl, $C_{1-12}$ alkyl-thiocarbonyl, $C_{1-12}$ alkylamino-carbonyl, $C_{1-12}$ alkylamino-thiocarbonyl, $C_{2-24}$ (total carbon number) dialkylamino-carbonyl, $C_{2-24}$ (total carbon number) dialkylamino-thiocarbonyl, $C_{1-12}$ alkoxyamino-carbonyl, $C_{1-12}$ alkoxyamino-thiocarbonyl, $C_{1-12}$ alkoxy-carbonyl, $C_{1-12}$ alkoxy-$C_{1-12}$ alkyl-carbonyl, $C_{1-12}$ thioalkoxy-$C_{1-12}$ alkyl-carbonyl, $C_{1-12}$ alkylsulfonyl-$C_{1-12}$ alkyl-alkyl-carbonyl, $C_{1-12}$ alkylsulfenyl-$C_{1-12}$ carbonyl, $C_{1-12}$ alkoxy-thiocarbonyl, $C_{1-12}$ thioalkoxy-carbonyl, $C_{1-12}$ thioalkoxy-thiocarbonyl, $C_{1-12}$ alkylsulfonyl, $C_{3-8}$ cycloalkyl-carbonyl, $C_{3-8}$ cycloalkyl-$C_{1-12}$ alkyl-carbonyl, $C_{2-12}$ alkenyl-carbonyl, $C_{2-12}$ alkynyl-carbonyl, $C_{3-8}$ cycloalkylamino-carbonyl, $C_{2-12}$ alkenylamino-carbonyl, $C_{2-12}$ alkynylamino-carbonyl, —C(=O)$R^5$ or C(=S)$R^5$, and herein, each group from $C_{1-12}$ alkyl-carbonyl to $C_{2-12}$ alkynylamino-carbonyl above may be optionally substituted,
or $R^3$ and $R^4$ may form, together with the nitrogen atom to which they are bound, a 3- to 6-membered heterocycle, and herein, the heterocycle may be optionally substituted with X, keto, thioketo, or nitroimino,
X and Y, which may be the same or different from each other, represent hydrogen, halogen, nitro, cyano, hydroxy, mercapto, $SF_5$, amino, $C_{1-12}$ alkyl, $C_{3-8}$ cycloalkyl, $C_{1-12}$ alkoxy, $C_{1-12}$ alkylthio, $C_{1-12}$ alkylsulfinyl, $C_{1-12}$ alkylsulfonyl, $C_{1-12}$ alkylsulfonyloxy, $C_{1-12}$ alkylaminosulfonyl, $C_{2-24}$ (total carbon number) dialkylaminosulfonyl, $C_{1-12}$ alkylcarbonylamino, benzoylamino, tri($C_{1-12}$ alkyl)silyl, $C_{1-12}$ alkoxyimino, $C_{1-12}$ alkylsulfinylimino, $C_{1-12}$ alkylsulfonylimino, $C_{1-12}$ alkoxy-carbonyl, $C_{1-12}$ alkylcarbonyl, aminocarbonyl, $C_{1-12}$ alkylamino-carbonyl, amino-thiocarbonyl, $C_{1-12}$ alkylamino-thiocarbonyl, $C_{2-24}$ (total carbon number) dialkylamino-carbonyl or $C_{2-24}$ (total carbon number) dialkylamino-thiocarbonyl, and herein, each group from $C_{1-12}$ alkyl to $C_{2-24}$ (total carbon number) dialkylamino-thiocarbonyl above may be optionally substituted, and
$R^5$ represents a phenyl group which may be optionally substituted or a 5- to 6-membered heterocyclic group that contains at least one hetero atom optionally selected from N, O, and S and may be optionally substituted.

DETAILED DESCRIPTION OF A PREFERRED EMBODIMENT

For the descriptions hereinbelow, unless specifically described otherwise, definition of the symbols in each formula has the same meanings as those described above.

The compounds having the Formula (I) of the present invention can be prepared according to the following preparation method (a) and/or (b).

Preparation Method (a)

A method of reacting the compounds that are represented by the following formula Formula (Int. 1):

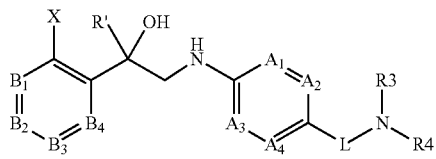

with the compounds that are represented by the following formula in an appropriate diluent, if necessary, in the presence of a base.

Formula (Int. 2):

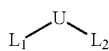

In the above formula, $L_1$ independently represents halogen or $C_{1-4}$ haloalkylsulfonyloxy, or two $L_1$ represent =O when U represents $CH_2$.

Preparation method (b): A method of oxidizing the compounds that are represented by the following formula with an appropriate oxidizing agent, if necessary, in the presence of a catalyst when U is $SO_2$.

Formula (I-2):

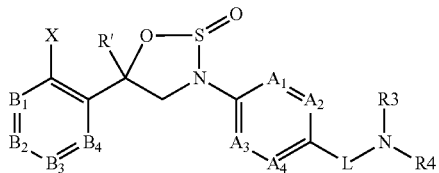

In the present specification, the term "alkyl" indicates linear or branched $C_{1-12}$ alkyl, for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl and the like, preferably $C_{1-6}$ alkyl, and more preferably $C_{1-4}$ alkyl.

In addition, for an alkyl moiety that is included as a part of the constitution in other groups, those described in the above for the "alkyl" can be also exemplified.

The term "alkyl substituted with halogen" means "haloalkyl" and it indicates a carbon chain in which at least one hydrogen on linear or branched $C_{1-12}$ alkyl, preferably $C_{1-6}$ alkyl, and more preferably $C_{1-4}$ alkyl is substituted with a halogen(s), for example, $CH_2F$, $CHF_2$, $CF_3$, $CF_2Cl$, $CFCl_2$, $CF_2Br$, $CF_2CF_3$, $CFHCF_3$, $CH_2CF_3$, $CFClCF_3$, $CCl_2CF_3$, $CF_2CH_3$, $CF_2CH_2F$, $CF_2CHF_2$, $CF_2CF_2Cl$, $CF_2CF_2Br$, $CFHCH_3$, $CFHCHF_2$, $CFHCHF_2$, $CHFCF_3$, $CHFCF_2Cl$, $CHFCF_2Br$, $CFClCF_3$, $CCl_2CF_3$, $CF_2CF_2CF_3$, $CH_2CF_2CF_3$, $CF_2CH_2CF_3$, $CF_2CF_2CH_3$, $CHFCF_2CF_3$, $CF_2CHFCF_3$, $CF_2CF_2CHF_2$, $CF_2CF_2CH_2F$, $CF_2CF_2CF_2Cl$, $CF_2CF_2CF_2Br$, $CH(CHF_2)CF_3$, $CH(CF_3)CF_3$, $CF(CF_3)CF_3$, $CF(CF_3)CF_2Br$, $CF_2CF_2CF_2CF_3$, $CH(CF_3)CF_2CF_3$ or $CF(CF_3)CF_2CF_3$. Perfluoroalkyls in which each substitutable hydrogen on alkyl is substituted with fluorine are also included. The haloalkyl may be further substituted.

The term "alkoxy" indicates linear or branched $C_{1-12}$, preferably $C_{1-6}$, and more preferably $C_{1-4}$ alkoxy, for example, methoxy, ethoxy, n-propoxy, i-propoxy, n-, iso-, sec- or tert-butoxy, pentyloxy, or hexyloxy. The alkoxy may be further substituted.

The term "halogen" and the halogen moiety in a group which is substituted with halogen represent fluorine, chlorine, bromine, and iodine, preferably fluorine, chlorine and bromine.

The term "cycloalkyl" represents $C_{3-8}$ cycloalkyl including cyclopropyl, cyclobutyl, cyclopentyl, cyclohexyl, cycloheptyl, and cyclooctyl, preferably $C_{3-7}$ cycloalkyl, and more preferably $C_{3-6}$ cycloalkyl.

In addition, for a cycloalkyl moiety that is included as a part of the constitution in other groups, those described in the above for the "cycloalkyl" can be also exemplified.

The term "cycloalkyl substituted with halogen" represents "halocycloalkyl" including fluorocyclopropyl, chlorocyclopropyl, difluorocyclopropyl, dichlorocyclopropyl, and undecafluorocyclohexyl.

The term "alkenyl" represents $C_{2-12}$ alkenyl, preferably $C_{2-5}$ alkenyl including vinyl, allyl, 1-propenyl, 1- (or 2-, or 3-)butenyl, 1-pentenyl and the like, and more preferably $C_{2-4}$ alkenyl.

The term "alkynyl" represents $C_{2-12}$ alkynyl, preferably $C_{2-5}$ alkynyl including ethynyl, propargyl, 1-propynyl, butan-3-ynyl, pentan-4-ynyl and the like, and more preferably $C_{2-4}$ alkynyl.

The term "heterocycle" represents a 5- or 6-membered heterocyclic group which contains at least one of N, O and S as a hetero atom. The cycle represents a fused heterocyclic group which may be benzo-fused and the carbon atom of the cycle may be substituted with oxo or thioxo.

Specific examples of the heterocycle include pyrrolidinyl, piperidinyl, morpholinyl, and thiomorpholinyl (examples of the saturated), dihydropyrrolyl, dihydroisoxazolyl, dihydropyrazolyl, dihydrooxazolyl, dihydrothiazolyl (examples of the partially saturated), furyl, thienyl, pyrrolyl, isoxazolyl, pyrazolyl, oxazolyl, isothiazolyl, thiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, benzothiazolyl, quinolyl and the like. The heterocycle may be further substituted with any substituent group.

With respect to the compounds having the Formula (I) of the present invention, examples of the preferred compounds include the followings.

R' represents $C_{1-6}$ alkyl or $C_{1-6}$ haloalkyl, $A_1$, $A_2$, $A_3$ and $A_4$ each independently represent C—Y or N, $B_1$, $B_2$, $B_3$ and $B_4$ each independently represent C—X or N, X and Y each independently represent hydrogen, halogen, nitro, cyano, hydroxy, mercapto, amino, $SF_5$, $C_{1-6}$ alkyl, $C_{3-7}$ cycloalkyl, $C_{1-6}$ alkoxy, $C_{1-6}$ alkylthio, $C_{1-6}$ alkylsulfinyl, $C_{1-6}$ alkylsulfonyl, $C_{1-6}$ alkylsulfonyloxy, $C_{1-6}$ alkylaminosulfonyl, di($C_{1-6}$ alkyl)amino-sulfonyl, $C_{1-6}$ alkyl-carbonylamino, benzoylamino, tri($C_{1-6}$ alkyl)silyl, $C_{1-6}$ alkoxyimino, $C_{1-6}$ alkylsulfinylimino, $C_{1-6}$ alkylsulfonylimino, $C_{1-6}$ alkoxy-carbonyl, $C_{1-6}$ alkyl-carbonyl, aminocarbonyl, $C_{1-6}$ alkylamino-carbonyl, aminothiocarbonyl, $C_{1-6}$ alkylamino-thiocarbonyl, di($C_{1-6}$ alkyl)amino-carbonyl or di($C_{1-6}$ alkyl) amino-thiocarbonyl, and herein, each group from $C_{1-6}$ alkyl to di($C_{1-6}$ alkyl)amino-thiocarbonyl above may be optionally substituted with halogen, $R^1$ and $R^2$ each independently represent hydrogen, cyano, $C_{1-6}$ alkyl, $C_{3-7}$ cycloalkyl, $C_{3-7}$ cycloalkyl-$C_{1-6}$ alkyl, $C_{2-6}$ alkenyl, $C_{2-6}$ alkynyl, $C_{1-6}$ alkoxy-carbonyl or $C_{1-6}$ thioalkoxy-carbonyl, and herein, each group from $C_{1-6}$ alkyl to $C_{1-6}$ thioalkoxy-carbonyl above may be optionally substituted with halogen, or $R^1$ and $R^2$ may form, together with the carbon atom to which they are bound, a 3- to 6-membered hydrocarbon ring, or $R^1$ may form, together with Y of $A_2$, $C_{2-3}$ alkylene when n represents 1 and $A_2$ represents C—Y, $R^3$ represents hydrogen, amino, hydroxy, cyano, $C_{1-6}$ alkyl, $C_{1-6}$ alkoxy, $C_{1-6}$ alkyl-carbonylamino, $C_{1-6}$ alkylamino, $C_{3-7}$ cycloalkyl, $C_{2-6}$ alkenyl, $C_{2-6}$ alkynyl, $C_{1-6}$ alkyl-carbonyl, —CH$_2$—R$^5$, —C(=O)R$^5$ or C(=S)R$^5$, and herein, each group from $C_{1-6}$ alkyl to $C_{1-6}$ alkyl-carbonyl above may be optionally substituted with halogen, $R^4$ represents hydrogen, cyano, formyl, thioformyl, $C_{1-6}$ alkyl-carbonyl, $C_{1-6}$ alkyl-thiocarbonyl, $C_{1-6}$ alkylamino-carbonyl, $C_{1-6}$ alkylamino-thiocarbonyl, di($C_{1-6}$ alkyl)amino-carbonyl, di($C_{1-6}$ alkyl)amino-thiocarbonyl, $C_{1-6}$ alkoxyamino-carbonyl, $C_{1-6}$ alkoxyamino-thiocarbonyl, $C_{1-6}$ alkoxy-carbonyl, $C_{1-6}$ alkoxy-$C_{1-6}$ alkyl-carbonyl, $C_{1-6}$ thioalkoxy-$C_{1-6}$ alkyl-carbonyl, $C_{1-6}$ alkylsulfenyl-$C_{1-6}$ alkyl-carbonyl, $C_{1-6}$ alkylsulfonyl-$C_{1-6}$ alkyl-carbonyl, $C_{1-6}$ alkoxy-thiocarbonyl, $C_{1-6}$ thioalkoxy-carbonyl, $C_{1-6}$ thioalkoxy-thiocarbonyl, $C_{1-6}$ alkylsulfonyl, $C_{3-7}$ cycloalkyl-carbonyl, $C_{3-7}$ cycloalkyl-$C_{1-6}$ alkyl-carbonyl, $C_{2-6}$ alkenyl-carbonyl, $C_{2-6}$ alkynyl-carbonyl, $C_{3-7}$ cycloalkylamino-carbonyl, $C_{2-6}$ alkenylamino-carbonyl, $C_{2-6}$ alkynylamino-carbonyl, —C(=O)R$^5$ or C(=S)R$^5$, and herein, each group from $C_{1-6}$ alkyl-carbonyl to $C_{2-6}$ alkynylamino-carbonyl above may be optionally substituted with halogen, and $R^5$ represents a phenyl group which may be optionally substituted or a 5- to 6-membered heterocyclic group that contains at least one hetero atom optionally selected from N, O, and S and may be optionally substituted.

Among the compounds having the Formula (I), examples of the particularly preferred compounds include the followings.

R' represents $C_{1-4}$ alkyl or $C_{1-4}$ haloalkyl, $A_1$, $A_2$, $A_3$ and $A_4$ each independently represent C—Y or N, $B_1$, $B_2$, $B_3$ and $B_4$ each independently represent C—X or N, X and Y each independently represent hydrogen, halogen, nitro, cyano, hydroxy, mercapto, amino, SF$_5$, $C_{1-4}$ alkyl, $C_{3-6}$ cycloalkyl, $C_{1-4}$ alkoxy, $C_{1-4}$ alkylthio, $C_{1-4}$ alkylsulfinyl, $C_{1-4}$ alkylsulfonyl, $C_{1-4}$ alkylsulfonyloxy, $C_{1-4}$ alkylamino-sulfonyl, di($C_{1-4}$ alkyl)amino-sulfonyl, $C_{1-4}$ alkyl-carbonylamino, benzoylamino, tri($C_{1-4}$ alkyl)silyl, $C_{1-4}$ alkoxyimino, $C_{1-4}$ alkylsulfinylimino, $C_{1-4}$ alkylsulfonylimino, $C_{1-4}$ alkoxy-carbonyl, $C_{1-4}$ alkyl-carbonyl, aminocarbonyl, $C_{1-4}$ alkylamino-carbonyl, aminothiocarbonyl, $C_{1-4}$ alkylamino-thiocarbonyl, di($C_{1-4}$ alkyl)amino-carbonyl or di($C_{1-4}$ alkyl)amino-thiocarbonyl, and herein, each group from $C_{1-4}$ alkyl to di($C_{1-4}$ alkyl)amino-thiocarbonyl above may be optionally substituted with halogen, $R^1$ and $R^2$ each independently represent hydrogen, cyano, $C_{1-4}$ alkyl, $C_{3-6}$ cycloalkyl, $C_{3-6}$ cycloalkyl-$C_{1-4}$ alkyl, $C_{2-4}$ alkenyl, $C_{2-4}$ alkynyl, $C_{1-4}$ alkoxy-carbonyl or $C_{1-4}$ thioalkoxy-carbonyl, and herein, each group from $C_{1-4}$ alkyl to $C_{1-4}$ thioalkoxy-carbonyl above may be optionally substituted with halogen, or $R^1$ and $R^2$ may form, together with the carbon atom to which they are bound, a 3- to 6-membered hydrocarbon ring, or $R^1$ may form, together with Y of $A_2$, $C_{2-3}$ alkylene when n represents 1 and $A_2$ represents C—Y, $R^3$ represents hydrogen, amino, hydroxy, cyano, $C_{1-4}$ alkyl, $C_{1-4}$ alkoxy, $C_{1-4}$ alkyl-carbonylamino, $C_{1-4}$ alkylamino, $C_{3-6}$ cycloalkyl, $C_{2-4}$ alkenyl, $C_{2-4}$ alkynyl, $C_{1-4}$ alkyl-carbonyl, —CH$_2$—R$^5$, —C(=O)R$^5$ or C(=S)R$^5$, and herein, each group from $C_{1-4}$ alkyl to $C_{1-4}$ alkyl-carbonyl above may be optionally substituted with halogen, $R^4$ represents hydrogen, cyano, formyl, thioformyl, $C_{1-4}$ alkyl-carbonyl, $C_{1-4}$ alkyl-thiocarbonyl, $C_{1-4}$ alkylamino-carbonyl, $C_{1-4}$ alkylamino-thiocarbonyl, di($C_{1-4}$ alkyl)amino-carbonyl, di($C_{1-4}$ alkyl)amino-thiocarbonyl, $C_{1-4}$ alkoxyamino-carbonyl, $C_{1-4}$ alkoxyamino-thiocarbonyl, $C_{1-4}$ alkoxy-carbonyl, $C_{1-4}$ alkoxy-$C_{1-4}$ alkyl-carbonyl, $C_{1-4}$ thioalkoxy-$C_{1-4}$ alkyl-carbonyl, $C_{1-4}$ alkylsulfenyl-$C_{1-4}$ alkyl-carbonyl, $C_{1-4}$ alkylsulfonyl-$C_{1-4}$ alkyl-carbonyl, $C_{1-4}$ alkoxy-thiocarbonyl, $C_{1-4}$ thioalkoxy-carbonyl, $C_{1-4}$ thioalkoxy-thiocarbonyl, $C_{1-4}$ alkylsulfonyl, $C_{3-6}$ cycloalkyl-carbonyl, $C_{3-6}$ cycloalkyl-$C_{1-4}$ alkyl-carbonyl, $C_{2-4}$ alkenyl-carbonyl, $C_{2-4}$ alkynyl-carbonyl, $C_{3-6}$ cycloalkylamino-carbonyl, $C_{2-4}$ alkenylamino-carbonyl, $C_{2-4}$ alkynylamino-carbonyl, —C(=O)R$^5$ or C(=S)R$^5$, and herein, each group from $C_{1-4}$ alkyl-carbonyl to $C_{2-4}$ alkynylamino-carbonyl above may be optionally substituted with halogen, and $R^5$ represents a phenyl group which may be optionally substituted or a 5- to 6-membered heterocyclic group that contains at least one hetero atom optionally selected from N, O, and S and may be optionally substituted.

Further, among the compounds having the Formula (I), examples of the most preferred compounds include the followings.

R' represents CF$_3$, $A_1$, $A_2$, $A_3$ and $A_4$ each independently represent C—Y or N, $B_1$, $B_2$, $B_3$ and $B_4$ each independently represent C—X or N, X and Y each independently represent hydrogen, halogen, $C_{1-4}$ alkyl or $C_{1-4}$ haloalkyl, and particularly preferably hydrogen, methyl, chloro, bromo or CF$_3$, $R^1$ represents hydrogen, or may form, together with Y of $A_2$, $C_{2-3}$ alkylene when n represents 1 and $A_2$ represents C—Y, $R^2$ represents hydrogen or $C_{1-4}$ alkyl, and particularly preferably hydrogen or methyl, $R^3$ represents hydrogen or $C_{1-4}$ alkyl, $R^4$ represents hydrogen, $C_{1-4}$ alkyl-carbonyl, $C_{1-4}$ haloalkyl-carbonyl, $C_{3-6}$ cycloalkyl-carbonyl, $C_{1-4}$ alkoxy-$C_{1-4}$ alkyl-carbonyl, $C_{1-4}$ thioalkoxy-$C_{1-4}$ alkyl-carbonyl, $C_{1-4}$ alkylsulfenyl-$C_{1-4}$ alkyl-carbonyl, $C_{1-4}$ alkylsulfonyl-$C_{1-4}$ alkyl-carbonyl or $C_{1-4}$ alkylamino-carbonyl, and particularly preferably $C_{1-4}$ alkyl-carbonyl, $C_{1-4}$ haloalkyl-carbonyl or $C_{3-6}$ cycloalkyl-carbonyl.

Examples of the subgroups of the compounds having the Formula (I) of the present invention include Formula (I-1-a), (I-1-b), (I-2-a), (I-2-b), (I-3-a) and (I-3-b) described below.

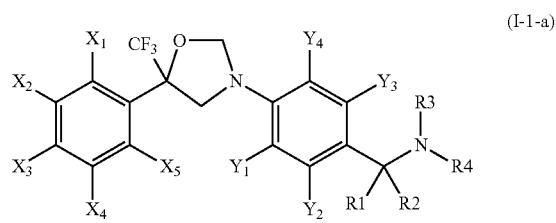

(I-1-a)

Wherein, $X^1$, $X^2$, $X^3$, $X^4$ and $X^5$ have the same meanings as those defined with respect to X; $Y^1$, $Y^2$, $Y^3$ and $Y^4$ have the same meanings as those defined with respect to Y; and $R^1$, $R^2$, $R^3$ and $R^4$ have the same meanings as those described above.

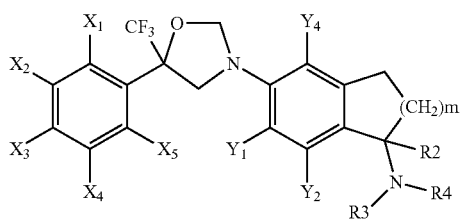

(I-1-b)

Wherein, $X^1$, $X^2$, $X^3$, $X^4$ and $X^5$ have the same meanings as those defined with respect to X; $Y^1$, $Y^2$ and $Y^4$ have the same meanings as those defined with respect to Y; and m, $R^2$, $R^3$ and $R^4$ have the same meanings as those described above.

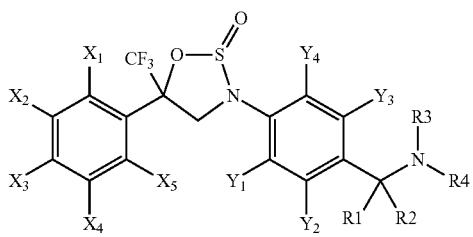

(I-2-a)

Wherein, $X^1$, $X^2$, $X^3$, $X^4$ and $X^5$ have the same meanings as those defined with respect to X; $Y^1$, $Y^2$, $Y^3$ and $Y^4$ have the same meanings as those defined with respect to Y; and $R^1$, $R^2$, $R^3$ and $R^4$ have the same meanings as those described above.

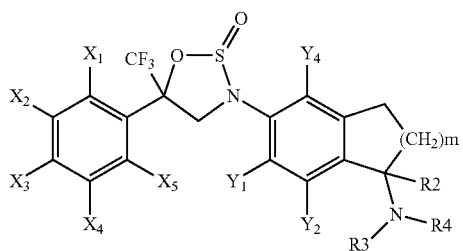

(I-2-b)

Wherein, $X^1$, $X^2$, $X^3$, $X^4$ and $X^5$ have the same meanings as those defined with respect to X; $Y^1$, $Y^2$ and $Y^4$ have the same meanings as those defined with respect to Y; and m, $R^2$, $R^3$ and $R^4$ have the same meanings as those described above.

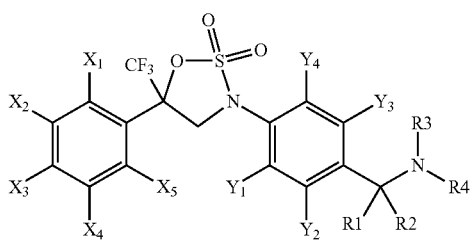

(I-3-a)

Wherein, $X^1$, $X^2$, $X^3$, $X^4$ and $X^5$ have the same meanings as those defined with respect to X; $Y^1$, $Y^2$, $Y^3$ and $Y^4$ have the same meanings as those defined with respect to Y; and $R^1$, $R^2$, $R^3$ and $R^4$ have the same meanings as those described above.

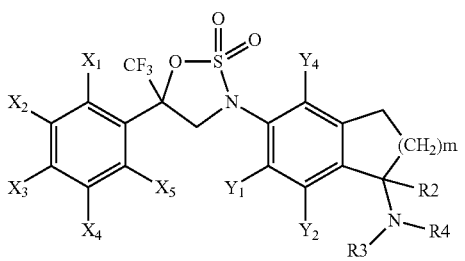

(I-3-b)

Wherein, $X^1$, $X^2$, $X^3$, $X^4$ and $X^5$ have the same meanings as those defined with respect to X; $Y^1$, $Y^2$ and $Y^4$ have the same meanings as those defined with respect to Y; and m, $R^2$, $R^3$ and $R^4$ have the same meanings as those described above.

The compound of Formula (Int. 1) in Preparation method (a) is obtained by hydrolysis of the compound of Formula (Int. 3), which can be produced with reference to the method described in Japanese Patent Application No. 2009-250744, in an appropriate solvent like water-containing ethanol or water-containing tetrahydron in the presence of an acid catalyst like hydrochloric acid:

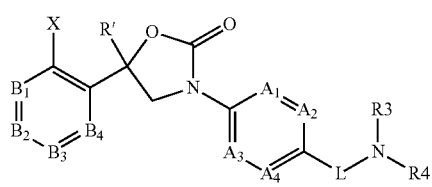

(Int.3)

Representative examples of the compound of Formula (Int. 3) include N-{4-[5-(3,5-dichlorophenyl)-2-oxo-5-(trifluoromethyl)-1,3-oxazolidin-3-yl]-2-(trifluoromethyl) benzyl}propane amide, N-{4-[5-(3,5-dichlorophenyl)-2-oxo-5-(trifluoromethyl)-1,3-oxazolidin-3-yl]-2-(trifluoromethyl)benzyl}cyclopropane carboxamide, N-{4-[2-oxo-5-(3,4,5-trichlorophenyl)-5-(trifluoromethyl)-1,3-oxazolidin-3-yl]-2-(trifluoromethyl)benzyl}propane amide, N-{4-[2-oxo-5-(3,4,5-trichlorophenyl)-5-(trifluoromethyl)-1,3-oxazolidin-3-yl]-2-(trifluoromethyl) benzyl}cyclopropane carboxamide, 2-cyclopropyl-N-{4-[2-oxo-5-(3,4,5-trichlorophenyl)-5-(trifluoromethyl)-1,3-oxazolidin-3-yl]-2-(trifluoromethyl)benzyl}acetamide, N-{4-[2-oxo-5-(3,4,5-trichlorophenyl)-5-(trifluoromethyl)-1,3-oxazolidin-3-yl]-2-(trifluoromethyl)benzyl}acetamide, 3,3,3-trifluoro-N-{4-[2-oxo-5-(3,4,5-trichlorophenyl)-5-(trifluoromethyl)-1,3-oxazolidin-3-yl]-2-(trifluoromethyl) benzyl}propane amide, N-(1-{4-[2-oxo-5-(3,4,5-trichlorophenyl)-5-(trifluoromethyl)-1,3-oxazolidin-3-yl] phenyl}ethyl)propane amide, N-(1S)-1-{4-[2-oxo-5-(3,4,5-trichlorophenyl)-5-(trifluoromethyl)-1,3-oxazolidin-3-yl] phenyl}ethyl)cyclopropane carboxamide, N-(1R)-1-{4-[2-oxo-5-(3,4,5-trichlorophenyl)-5-(trifluoromethyl)-1,3-oxazolidin-3-yl]phenyl}ethyl)cyclopropane carboxamide, N-[4-{2-oxo-5-(trifluoromethyl)-5-[3-(trifluoromethyl)phenyl]-1,3-oxazolidin-3-yl}-2-(trifluoromethyl)benzyl]propane amide, N-[4-{5-[3,5-bis(trifluoromethyl)phenyl]-2-oxo-5-(trifluoromethyl)-1,3-oxazolidin-3-yl}-2-(trifluoromethyl)benzyl]propane amide, N-{5-[5-(3,5-dichlorophenyl)-2-oxo-5-(trifluoromethyl)-1,3-oxazolidin- 3-yl]-2,3-dihydro-1H-inden-1-yl}propane amide, and N-{5-[2-oxo-5-(3,4,5-trichlorophenyl)-5-(trifluoromethyl)-1,3-oxazolidin-3-yl]-2,3-dihydro-1H-inden-1-yl}cyclopropane carboxamide.

The reaction of the Preparation method (a) can be carried out in a suitable diluent, and examples thereof include aliphatic hydrocarbons (e.g. hexane, cyclohexane, heptane etc.), aliphatic halogenated hydrocarbons (e.g. dichloromethane, chloroform, carbon tetrachloride, dichloroethane, etc.), aromatic hydrocarbons (e.g. benzene, toluene, xylene, chlorobenzene etc.), ethers (e.g. diethyl ether, dibutyl ether, dimethoxyethane (DME), tetrahydrofuran, dioxane etc.), esters (e.g. ethyl acetate, ethyl propionate etc.), acid amides (e.g. dimethylformamide (DMF), dimethylacetamide (DMA), N-methylpyrrolidone etc.), nitriles (e.g. acetonitrile, propionitrile etc.), dimethylsulfoxide (DMSO), water or mixed solvents thereof and the like.

Examples of the base for Preparation method (a) include alkali metal bases like lithium hydride, sodium hydride, potassium hydride, butyl lithium, tert-butyl lithium, trimethylsilyl lithium, lithium hexamethyl disilazide, sodium carbonate, potassium carbonate, cesium carbonate, tripotassium phosphate, sodium acetate, potassium acetate, sodium methoxide, sodium ethoxide, sodium-tert-butoxide, and potassium-tert-butoxide, organic bases like triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicyclo undecene, diazabicyclo octane, and imidazole, and the like.

Preparation method (a) can be carried out within a substantially wide temperature range. It may be generally carried out at the temperature from about −78° C. to about 200° C., preferably from about −10° C. to about 150° C. Said reaction is desirably carried out at normal pressure although it may be carried out under elevated or reduced pressure. The reaction time is from 0.1 to 72 hours, preferably from 0.1 to 24 hours.

For carrying out Preparation method (a), for example, by reacting from 1 to 3 mole of base and from 1 to 3 mole of the compound of Formula (Int. 2) with 1 mole of the compound of Formula (Int. 1) in a diluent, for example toluene, the compound having the Formula (I) of the present invention can be obtained.

Representative examples of the compound of Formula (Int. 1) include N-[4-{[3,3,3-trifluoro-2-hydroxy-2-(3,4,5-trichlorophenyl)propyl]amino}-2-(trifluoromethyl)benzyl] propane amide, and N-[4-{[3,3,3-trifluoro-2-hydroxy-2-(3,4,5-trichlorophenyl)propyl]amino}-2-(trifluoromethyl) benzyl]cyclopropane carboxamide.

Representative examples of the compound of Formula (Int. 2) include formaldehyde, thionyl chloride, and sulfuryl chloride.

Preparation method (b) can be carried out with reference to the method described in Journal of Organic Chemistry, 2006, 71, 1258-1261, etc.

The compound of Formula (I-2), which is a starting material for Preparation method (b), is included in the compounds of the present invention, and representative examples thereof include N-{4-[2-oxide-5-(3,4,5-trichlorophenyl)-5-(trifluoromethyl)-1,2,3-oxathiazolin-3-yl]-2-(trifluoromethyl) benzyl}propane amide, N-{4-[2-oxide-5-(3,4,5-trichlorophenyl)-5-(trifluoromethyl)-1,2,3-oxathiazolin-3-yl]-2-(trifluoromethyl)benzyl}cyclopropane carboxamide, and N-{5-[2-oxide-5-(3,4,5-trichlorophenyl)-5-(trifluoromethyl)-1,2,3-oxathiazolin-3-yl]-2,3-dihydro-1H-inden-1-yl) propane amide.

Examples of the diluent used for Preparation method (b) include methylene chloride, chloroform, dichloroethane, and acetonitrile.

Examples of the oxidizing agent used for Preparation method (b) include sodium periodate.

Examples of the catalyst used for Preparation method (b) include ruthenium (III) chloride.

For carrying out Preparation method (b), for example, by reacting from 0.01 to 0.1 mole of catalyst, for example ruthenium (III) chloride, and from 1 to 5 mole of oxidizing agent, for example sodium periodate, with 1 mole of the compound of Formula (I-2) in a diluent, for example methylene chloride, acetonitrile, the compound having the Formula (I-3) that is included in the compounds having the Formula (I) of the present invention can be obtained.

As shown in Scheme 1, Preparation methods (a) and (b) can be performed according to an appropriate synthetic process.

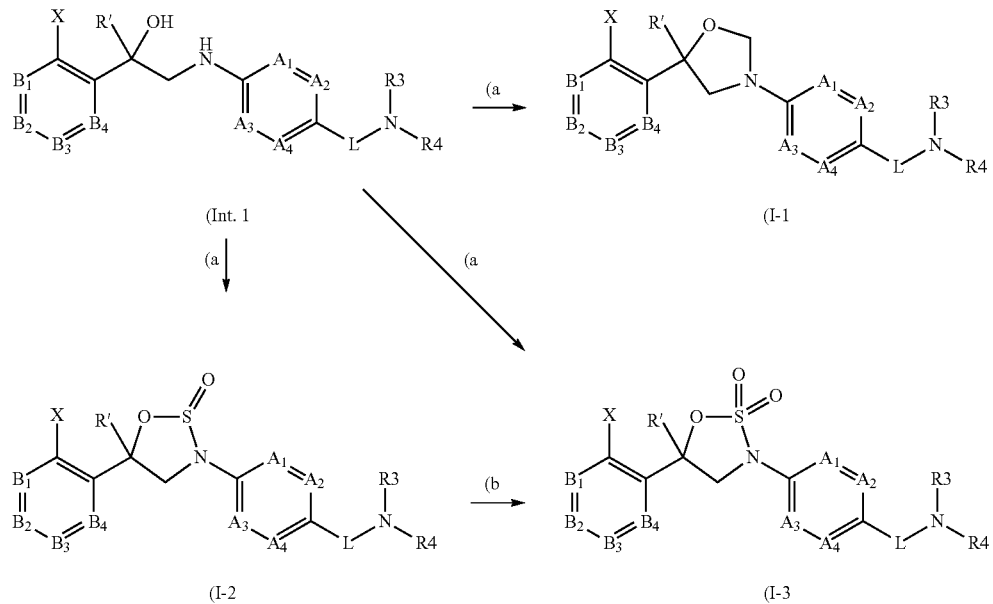

(Scheme 1)

Further, as shown in Scheme 2, hydrolysis of the compound of Formula (Int. 4), which can be produced with reference to the method described in Japanese Patent Application No. 2009-250744 described above, can give the compound of Formula (Int. 5), the compound of Formula (Int. 6) can be synthesized therefrom according to Preparation method (a) and/or (b), and subsequently the compound having the Formula (I-4), (I-5) or (I-6) that is included in the compounds having the Formula (I) of the present invention can be produced by following the method described in Japanese Patent Application No. 2009-250744 described above.

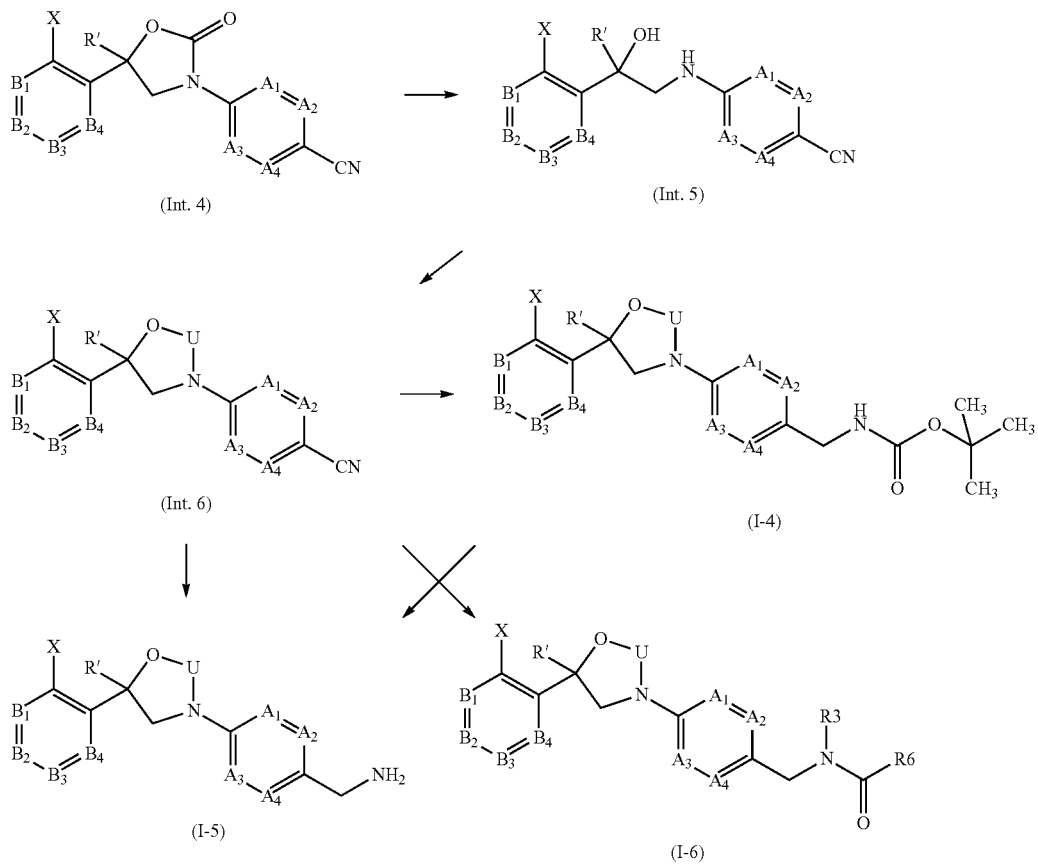

Some of the compounds having the Formula (I) of the present invention may have an asymmetric carbon, and therefore an optical isomer is included therein.

The compounds having the Formula (I) of the present invention exhibit a potent pesticidal effect, and therefore can be used as pesticides. Furthermore, the active compounds having the Formula (I) of the present invention exhibit a selective controlling effect against noxious pests without causing any damages on crop plants that are cultivated. Therefore, the compounds of the present invention can be used for controlling a wide variety of harmful organisms including, for example, harmful sucking insects, chewing insects and other plant parasitic pests, stored grain pests, hygienic pests etc., and can be applied for the removal and eradication of them.

Examples of the pests include the pests described below.

As an insect, coleopteran pests, such as *Callosobruchus Chinensis, Sitophilus zeamais, Tribolium castaneum, Epilachna vigintiocto-maculata, Agriotes ogurae fuscicollis, Anomala rufocuprea, Leptinotarsadecemlineata, Diabrotica* spp., *Monochamus alternatus endai, Lissorhoptrus oryzophilus, Lyctus brunneus;* lepidopteran pests, such as *Lymantria dispar, Malacosoma neustria, Pieris rapae crucivora, Spodoptera litura, Mamestra brassicae, Chilo suppressalis, Ostrinia nubilalis, Cadra cautella, Adoxophyes honmai, Cydia pomonella, Agrotis segetum, Galleria mellonella, Plutella xylostella, Heliothis virescens, Phyllocnistis citrella;* hemipterous pests, such as *Nephotettix cincticeps, Nilaparvata lugens, Pseudococcus comstocki, Unaspis yanonensis, Myzus persicas, Aphis pomi, Aphis gossypii, Lipaphis erysimi, Stephanitis nashi, Nezara* spp., *Trialeurodes vaporariorum, Psylla* spp.;

thysanoptera pests, such as *Thrips palmi, Franklinella occidentalis;* orthopteran pests, such as *Gryllotalpa africana, Locusta migratoria;* blattaria pests, such as Blatella germanica, Periplaneta americana, Reticulitermes speratus, Coptotermes formosanus;

dipterous pests, such as *Musca domestica, Aedes aegypti, Delia platura, Culex pipiens pallens, Anopheles sinensis, Culex tritaeniorhynchus, Liriomyza trifolii* and the like can be mentioned.

Further, as mites, *Tetranychus cinnabarinus, Tetranychus urticae, Panonychus citri, Aculops pelekassi, Tarsonemus* spp. and the like can be mentioned.

In addition, as nematodes, *Meloidogyne incognita, Bursaphelenchus xylophilus, Aphelenchoides besseyi, Heterodera glycines, Pratylenchus* spp. and the like can be mentioned.

In veterinary medicine field, i.e., veterinary science, the active compounds of the present invention can be effectively used against various harmful animal parasites, particularly, ectoparasites or endoparasites. The term "endoparasites" include in particular worms (tapeworm, eelworm, trematode and the like) and *plasmodium* (coccidium and the like). The term "ectoparasites" include in general and preferably an arthropod, in particular insects (fly (a fly which can sting and suck), larva of parasitic fly, sucking lice, crab lice, bird lice, flea, and the like) or acaroid mites (ticks and the like, for example, hard tick and soft tick) or mites (itch mite, chigger mite, bird mite and the like).

These parasites are as follows:

from Anoplurida, for example, *Haematopinus* spp., *Linognathus* spp., *Pediculus* spp., *Phtirus* spp., *Solenopotes* spp.; particularly, for representative examples, *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis*, and *Solenopotes capillatus*; from Mallophagida and Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particularly, for representative examples, *Bovicola bovis, Bovicola ovis, Bovicola limbata, Damalina bovis, Trichodectes canis, Felicola subrostratus, Bovicola caprae, Lepikentron ovis*, and *Werneckiella equi;* from Diptera and Nematocerina and Brachycerina, for example, *Aedes* spp., *Anopheles* ssp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp, *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particularly, for representative examples, *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorrhoidalis, Gasterophilus interrnis, Gasterophilus nasalis, Gasterophilus nigricornis, Gasterophilus pecorum, Braula coeca;* from Siphonapterida, for example, *Pulex* spp., *Ctenocephalides* spp., *Tunga* spp., *Xenopsylla* spp., *Ceratophyllus* spp.; particularly, for representative examples, *Ctenocephalides canis, Ctenocephalides felis, Pulex irritans, Tunga penetrans*, and *Xenopsylla cheopis;* from Heteropterida, for example, *Cimex* spp., *Triatoma* spp., *Rhodnius* spp., and *Panstrongylus* spp.;

from Blattarida, for example, *Blatta orientalis, Periplaneta americana, Blattela germanica*, and *Supella* spp. (for example, *Suppella longipalpa*);

from Acari (Acarina), Metastigmata and Mesostigmata, for example, *Argas* spp., *Ornithodorus* spp., *Otobius* spp., *Ixodes* spp., *Amblyomma* spp., *Rhipicephalus* (Boophilus) spp., *Dermacentor* spp., *Haemophysalis* spp., *Hyalomma* spp., *Dermanyssus* spp., *Rhipicephalus* spp. (original genus of heteroxenous mites), *Ornithonyssus* spp., *Pneumonyssus* spp., *Raillietia* spp., *Pneumonyssus* spp., *Sternostoma* spp., *Varroa* spp., *Acarapis* spp.; particularly, for representative examples, *Argas persicus, Argas reflexus, Ornithodorus moubata, Otobius megnini, Rhipicephalus* (Boophilus) *microplus, Rhipicephalus* (Boophilus) *decoloratus, Rhipicephalus* (Boophilus) *annulatus, Rhipicephalus* (Boophilus) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum*, and *Varroa jacobsconi;* from Actinedida (Prostigmata) and Acaridida (Astigmata), for example, *Acarapis* spp., *Cheyletiella* spp., *Ornithocheyletia* spp., *Myobia* spp, *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particularly, for representative examples, *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleli, Neoschonegastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum*, and *Acarapis woodi.*

The active compounds of the present invention are also useful for removing an arthropod, a worm and a *plasmodium* which attacks an animal. Examples of the animal include an agricultural animals such as a cow, a sheep, a goat, a horse, a pig, a donkey, a camel, a buffalo, a rabbit, a chicken, a turkey, a duck, a goose, a cultured fish, a honey bee, etc. In addition, a pet which is also called as a companion animal, for example, a dog, a cat, a caged bird, an aquarium fish, and a laboratory animal (e.g., a hamster, a guinea pig, a rat, a mouse and the like) are also included.

With control of the arthropod, larvae, and/or *plasmodium* by using the active compound of the present invention, death ratio of a host animal can be reduced and productivity (for meat, milk, wool, leather, egg, and honey) and health of the animal can be improved. As a result, it is intended to achieve economically more favorable and simple animal breeding.

For example, it is preferable that sucking of host blood by a parasite is either prevented or inhibited (if possible). Parasite removal can be useful for preventing infection which is caused by inflammatory pathogens.

The term "removal" that is used in the present specification regarding a veterinary medicine field means that the active compounds are effective for reducing the occurrence ratio of each parasite in the animal infected with it to a harmless level. More specifically, the term "removal" that is used in the present specification means that the active compounds are effective for destroying parasites, inhibiting growth or propagation thereof.

In the present invention, substances having pesticidal effects against harmful pests encompassing all of such pests are referred to as pesticides.

When used as pesticides, the active compounds of the present invention can be prepared in the form of a common preparation. Such preparation form may include, for example, liquids, emulsions, wettable powders, granulated wettable powders, suspensions, powders, foams, pastes, tablets, granules, aerosols, natural or synthetic agents impregnated with the active compounds, microcapsules, coating agents for seeds, formulations equipped with a combustion device (the combustion device can be a smoke or fog cartridge, a can or a coil, etc.) and ULV [cold mist, warm mist], and the like.

These preparations can be produced by known methods per se. For example, they can be prepared by mixing the active compounds with extenders, namely, liquid diluents or carriers; liquefied gas diluents or carriers; solid diluents or carriers and, optionally, with surfactants, namely, emulsifiers and/or dispersants and/or foam formers and the like.

In case of using water as an extender, for example, organic solvents can be used as auxiliary solvents.

Liquid diluents or carriers may include, for example, aromatic hydrocarbons (e.g. xylene, toluene, alkyl naphthalene etc.), chlorinated aromatic or chlorinated aliphatic hydrocarbons (e.g. chlorobenzenes, ethylene chlorides, methylene chlorides etc.), aliphatic hydrocarbons (e.g. cyclohexanes or paraffins (e.g. mineral oil fractions)), alcohols (e.g. butanol, glycol and ethers or esters thereof, etc.), ketones (e.g. acetone, methyl ethyl ketone, methyl isobutyl ketone, cyclohexanone etc.), strong polar solvents (e.g. dimethyl formamide, dimethyl sulfoxide etc.), water and the like.

Liquefied gas diluent or carrier may include those presented as gas at atmospheric pressure and temperature, for example, bulan, propane, nitrogen gas, carbon dioxide, and aerosol propellant such as halogenated hydrocarbons.

Examples of the solid diluents may include ground natural minerals (for example, kaolins, clay, talc, chalk, quartz, attapulgite, montmorillonite or diatomaceous earth, etc.) and ground synthetic minerals (for example, highly dispersed silicic acid, alumina and silicate, etc.) and the like.

Examples of the solid carriers for granules may include crushed and fractionated rocks (for example, calcite, marble, pumice, sepiolite and dolomite, etc.), synthetic granules of inorganic or organic powders, and fine granules of organic materials (for example, sawdust, coconut shells, maize cobs and tobacco stalks, etc.) and the like.

Examples of the emulsifiers and/or foam formers may include nonionic and anionic emulsifiers [for example, polyoxyethylene fatty acid esters, polyoxyethylene fatty acid alcohol ethers (for example, alkylaryl polyglycol ether), alkyl sulfonates, alkyl sulfates and aryl sulfonates] and albumin hydrolyzates and the like.

The dispersants include lignin sulfite waste liquid and methyl cellulose.

Binders may also be used in the preparations (powders, granules and emulsion). Examples of the binders may include carboxymethyl cellulose, and natural or synthetic polymers (for example, gum Arabic, polyvinyl alcohol and polyvinyl acetate, etc).

Colorants may also be used. Examples of the colorants may include inorganic pigments (for example, iron oxide, titanium oxide and Prussian blue, etc.), organic dyes such as Alizarin dyes, azo dyes or metal phthalocyanine dyes, and further, trace elements such as salts of iron, manganese, boron, copper, cobalt, molybdenum or zinc.

The preparation may generally include the above active components in an amount from 0.1 to 95% by weight, preferably from 0.5 to 90% by weight.

The active compounds of the Formula (I) of the present invention can be provided as mixtures with other active compounds such as pesticides, poison baits, sterilizing agents, acaricidal agents, nematocides, fungicides, growth regulating agents, herbicides, and the like in the form of commercially useful preparation or a usage form prepared from such preparation. The pesticides may include, for example, organic phosphorous agents, carbamate agents, carboxylate agents, chlorinated hydrocarbon agents, neonicotinoid pesticides, and pesticidal substances produced by microorganisms, etc.

Further, the active compounds of the Formula (I) of the present invention can be provided as mixtures with synergists. Such preparation and usage form may include those that are commercially useful. The synergists are not necessarily active by themselves. Rather, they are the compounds which enhance the activity of the active compounds.

The amount of the active compounds of the Formula (I) of the present invention in a commercially useful form may vary over a broad range.

The concentration of the active compounds of the Formula (I) of the present invention for actual use can be, for example, in the range from 0.0000001 to 95% by weight, preferably from 0.00001 to 90% by weight.

The compounds of the Formula (I) of the present invention can be used according to any common methods that are appropriate for a usage form.

The active compounds of the present invention have stability that is effective for alkaline substances present in lime materials when the compounds are used against hygienic pests and storage pests. In addition, they exhibit excellent residual effectiveness in woods and soils.

Generally, when the active compounds of the present invention are used for the treatment of animals, they can be directly applied to the animal. Preferably, the compounds are applied in the form of pharmaceutical composition which may include a vehicle, an auxiliary agent, or both, that are known in the art and pharmaceutically acceptable.

For a veterinary medicine field and animal breeding, the active compounds can be applied (administered) according to various known ways, for example; intraintestinal administration with a tablet, a capsule, a drink, a drinkable medicine, granules, paste, and bolus administration, feed-through method, suppository; non-intraintestinal administration based on skin application such as injection (intramuscular, subcutaneous, intravenous, intraperitoneal, etc.), embedding, intranasal application, bathing or immersion, spray, pouring, dropping, washing and scattering, and by using a molding article containing the active compounds such as a necklace, an earmark, a tag, a leg brace, a halter, a marking device and the like. The active compounds of the present invention can be formulated into an appropriate formulation form that can be applied with a shampoo, aerosol, a non-pressurized spray, for example, a pump spray and a vaporizer spray, etc.

When used for livestock, fouls, pets and the like, the active compounds of the present invention can be used as a formulation which includes them in an amount from 1 to 80% by weight (for example, powders, wettable powders (WP), emulsion, emulsifiable concentrate (EC), fluid, homogeneous solution and suspension concentrate (SC)), and the formulation can be applied as it is or after dilution (for example, dilution of 100 to 10,000 times), or as a chemical bath as an alternative method.

When used in a veterinary medicine field, the active compounds of the present invention can be used in combination with appropriate synergistic agents or other active compounds, for example, acaricides, insecticides, parasticides, anti-plasmodium agents, etc.

The active compounds of the present invention have low toxicity, and therefore can be safely used for warm-blooded animals.

EXAMPLES

Hereinbelow, the present invention is described in greater detail with reference to the following examples. However, the present invention is not limited thereto.

Synthetic Example 1

Synthesis of N-{4-[5-(3,4,5-trichlorophenyl)-5-(trifluoromethyl)-1,3-oxazolidin-3-yl]-2-(trifluoromethyl)benzyl}propane amide (No. 1-17)

Step 1

Synthesis of N-[4-{[3,3,3-trifluoro-2-hydroxy-2-(3,4,5-trichlorophenyl)propyl]amino}-2-(trifluoromethyl)benzyl]propane amide

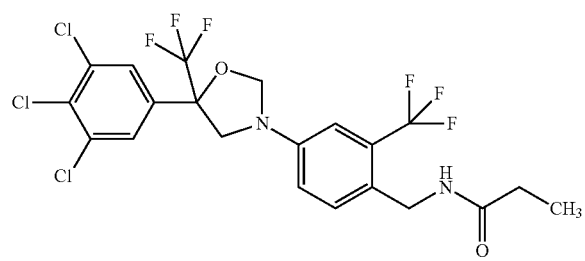 [SMILES: CCC(=O)NCc1ccc(N2COC(c3cc(Cl)c(Cl)c(Cl)c3)(C(F)(F)F)C2)cc1C(F)(F)F]

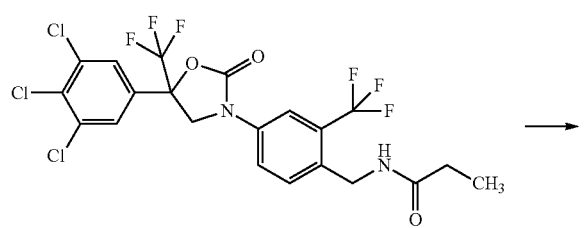

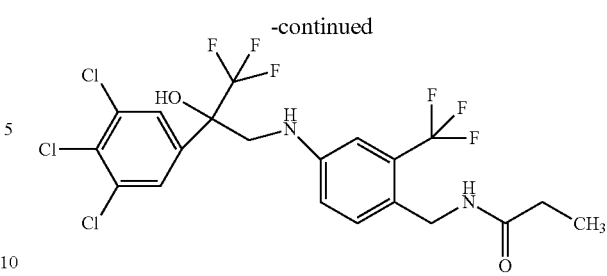

N-{4-[2-oxo-5-(3,4,5-trichlorophenyl)-5-(trifluoromethyl)-1,3-oxazolidin-3-yl]-2-(trifluoro-methyl)benzyl}propane amide (542 mg) was added to a solution of 1,4-dioxane (10 mL), water (10 mL) and potassium hydroxide (108 mg), and stirred at 70° C. for 1 hour. After the reaction, 1,4-dioxane was distilled off under reduced pressure, and conc. hydrochloric acid (70 mg) was added and stirred under ice cooling. The resultant was extracted with ethyl acetate, washed with water and saturated brine, and the organic layer is dried over anhydrous magnesium sulfate. The solvent was distilled off under reduced pressure and the residues were purified by silica-gel column chromatography to give N-[4-{[3,3,3-trifluoro-2-hydroxy-2-(3,4,5-trichlorophenyl)propyl]amino}-2-(trifluoromethyl)benzyl]propane amide (503 mg).

1H-NMR (CDCl$_3$) δ: 1.14 (3H, t), 2.21 (2H, q), 3.63-3.66 (1H, m), 3.88-3.93 (1H, m), 3.98-4.00 (1H, m), 4.40-4.43 (3H, m), 5.74 (1H, br s), 6.70-6.71 (1H, m), 6.86 (1H, s), 7.27-7.30 (1H, m), 7.64 (2H, s)

Step 2

Synthesis of N-{4-[5-(3,4,5-trichlorophenyl)-5-(trifluoromethyl)-1,3-oxazolidin-3-yl]-2-(trifluoromethyl)benzyl}propane amide

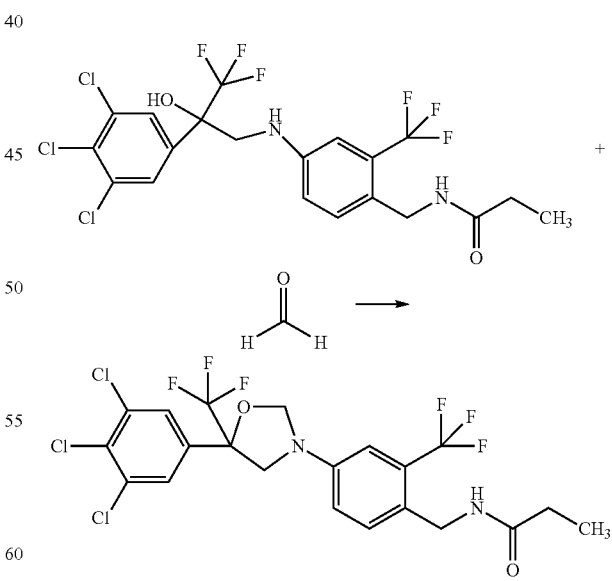

N-[4-{[3,3,3-Trifluoro-2-hydroxy-2-(3,4,5-trichlorophenyl)propyl]amino}-2-(trifluoromethyl)benzyl]propane amide (250 mg) and formaldehyde (70 mg) were added to toluene (20 mL), and stirred at 90° C. for 5 hours. After the reaction, the solvent was distilled off under reduced pressure and the residues were purified by silica-gel column chromatography to give N-{4-[5-(3,4,5-trichlorophenyl)-5-(trifluoromethyl)-1,3-oxazolidin-3-yl]-2-(trifluoromethyl)benzyl}propane amide (100 mg).

1H-NMR (CDCl₃) δ: 1.13-1.16 (3H, m), 2.18-2.23 (3H, m), 3.77-3.81 (1H, m), 4.12-4.15 (1H, m), 4.50 (2H, d), 5.20 (2H, d), 5.73 (1H, br s), 6.67 (1H, d), 6.77 (1H, d), 7.48 (1H, d), 7.59 (2H, s)

Synthetic Example 2

Synthesis of N-{4-[2-oxide-5-(3,4,5-trichlorophenyl)-5-(trifluoromethyl)-1,2,3-oxathiazolin-3-yl]-2-(trifluoromethyl)benzyl}propane amide (No. 3-17)

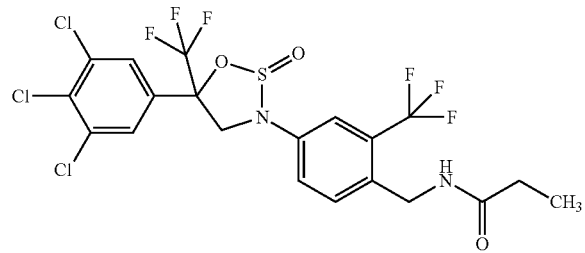 [SMILES: CCC(=O)NCc1ccc(N2CC(c3cc(Cl)c(Cl)c(Cl)c3)(C(F)(F)F)OS2=O)cc1C(F)(F)F]

N-[4-{[3,3,3-Trifluoro-2-hydroxy-2-(3,4,5-trichlorophenyl)propyl]amino}-2-(trifluoro-methyl)benzyl]propane amide (160 mg), triethylamine (130 mg), and N,N-dimethyl-4-aminopyridine (4 mg) were added to dichloromethane (10 mL), and under ice cooling, added dropwise with thionyl chloride (57 mg). After the dropwise addition, the mixture was stirred for 2.5 hours at room temperature. After the reaction, the solvent was distilled off under reduced pressure and the residues were purified by silica-gel column chromatography to give N-{4-[2-oxide-5-(3,4,5-trichlorophenyl)-5-(trifluoromethyl)-1,2,3-oxathiazolin-3-yl]-2-(trifluoromethyl)benzyl}propane amide (157 mg).

1H-NMR (CDCl₃) δ: 1H-NMR (CDCl₃) δ: 1.14-1.16 (3H, m), 2.17-2.27 (2H, m), 4.09-4.74 (4H, m), 5.80 (1H, br s), 7.22-7.65 (5H, m)

Synthetic Example 3

Synthesis of N-{4-[2,2-dioxide-5-(3,4,5-trichlorophenyl)-5-(trifluoromethyl)-1,2,3-oxathiazolin-3-yl]-2-(trifluoromethyl)benzyl}propane amide (No. 5-17)

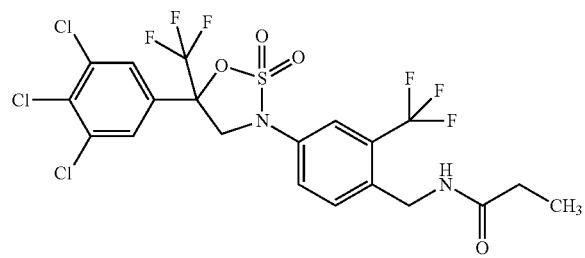

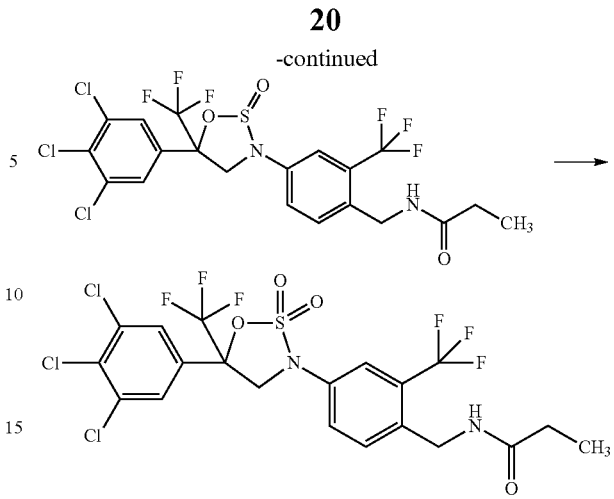

N-{4-[2-Oxide-5-(3,4,5-trichlorophenyl)-5-(trifluoromethyl)-1,2,3-oxathiazolin-3-yl]-2-(tri-fluoromethyl)benzyl}propane amide (190 mg) was dissolved in dichloromethane (1.5 mL) and acetonitrile (1.5 mL). Under ice cooling, ruthenium (III) chloride (5 mg) was added and stirred for 10 minutes. Subsequently, sodium periodate (111 mg) and phosphate buffer solution (pH 7, 1.5 mL) were added thereto and stirred for 2 hours under ice cooling. Temperature was raised to room temperature and the mixture was filtered using Celite. The organic layer was washed with water and dried over anhydrous magnesium sulfate. The solvent was distilled off under reduced pressure and the residues were purified by silica-gel column chromatography to give N-{4-[2,2-dioxide-5-(3,4,5-trichlorophenyl)-5-(trifluoromethyl)-1,2,3-oxathiazolin-3-yl]-2-(trifluoromethyl)benzyl}propane amide (157 mg).

1H-NMR (CDCl₃) δ: 7.68-7.47 (4H, m), 7.29 (1H, m), 5.87 (1H, m), 4.67-4.23 (4H, m), 2.28-2.18 (2H, m), 1.18-1.11 (3H, t)

Compounds having the Formula (I) of the present invention and novel intermediates that are obtained according to the methods similar to the Synthetic example above or the methods described in detail above are described in Tables 1 to 6 and Tables 7 to 11, respectively. Their NMR measurement data are described in the NMR table. Further, each compound obtained from the Synthetic examples above is also described in the corresponding table.

Abbreviated symbols in the tables are as follows.

Me: methyl, Et: ethyl, Pr: propyl, Bu: butyl, n-: normal, cyclo-: cyclo, tert-: tertiary.

Further, the compound given with "-a" in compound number indicates S form for the stereo configuration of the carbon atom to which $R^1$ and $R^2$ are bound. "-b" indicates R form.

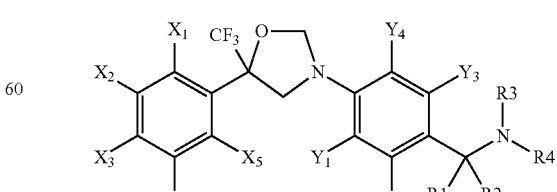

Wherein, $X^1, X^5, Y^1, Y^2, Y^4, R^2$ and $R^3$ represent hydrogen.

TABLE 1

| Compound No. | $X^2$ | $X^3$ | $X^4$ | $Y^3$ | $R^1$ | $R^4$ |
|---|---|---|---|---|---|---|
| 1-1 | Cl | H | Cl | $CF_3$ | H | H |
| 1-2 | Cl | H | Cl | $CF_3$ | H | MeCO |
| 1-3 | Cl | H | Cl | $CF_3$ | H | EtCO |
| 1-4 | Cl | H | Cl | $CF_3$ | H | n-PrCO |
| 1-5 | Cl | H | Cl | $CF_3$ | H | cyclo-PrCO |
| 1-6 | Cl | H | Cl | $CF_3$ | H | cyclo-PrCH$_2$CO |
| 1-7 | Cl | H | Cl | $CF_3$ | H | $CF_3CH_2CO$ |
| 1-8 | Cl | H | Cl | $CF_3$ | H | $CH_3SCH_2CO$ |
| 1-9 | Cl | H | Cl | $CF_3$ | H | $CH_3SOCH_2CO$ |
| 1-10 | Cl | H | Cl | $CF_3$ | H | $CH_3SO_2CH_2CO$ |
| 1-11 | Cl | H | Cl | $CF_3$ | H | $CH_3OCH_2CH_2CO$ |
| 1-12 | Cl | H | Cl | $CF_3$ | H | $CH_3OCH(Me)CH_2CO$ |
| 1-13 | Cl | H | Cl | $CF_3$ | H | EtNHCO |
| 1-14 | Cl | H | Cl | $CF_3$ | H | tert-BuOC(=O) |
| 1-15 | Cl | Cl | Cl | $CF_3$ | H | H |
| 1-16 | Cl | Cl | Cl | $CF_3$ | H | MeCO |
| 1-17 | Cl | Cl | Cl | $CF_3$ | H | EtCO |
| 1-18 | Cl | Cl | Cl | $CF_3$ | H | n-PrCO |
| 1-19 | Cl | Cl | Cl | $CF_3$ | H | cyclo-PrCO |
| 1-20 | Cl | Cl | Cl | $CF_3$ | H | cyclo-PrCH$_2$CO |
| 1-21 | Cl | Cl | Cl | $CF_3$ | H | $CF_3CH_2CO$ |
| 1-22 | Cl | Cl | Cl | $CF_3$ | H | $CH_3SCH_2CO$ |
| 1-23 | Cl | Cl | Cl | $CF_3$ | H | $CH_3SOCH_2CO$ |
| 1-24 | Cl | Cl | Cl | $CF_3$ | H | $CH_3SO_2CH_2CO$ |
| 1-25 | Cl | Cl | Cl | $CF_3$ | H | $CH_3OCH_2CH_2CO$ |
| 1-26 | Cl | Cl | Cl | $CF_3$ | H | $CH_3OCH(Me)CH_2CO$ |
| 1-27 | Cl | Cl | Cl | $CF_3$ | H | EtNHCO |
| 1-28 | Cl | Cl | Cl | $CF_3$ | H | tert-BuOC(=O) |
| 1-29 | Cl | Cl | Cl | Cl | H | H |
| 1-30 | Cl | Cl | Cl | Cl | H | MeCO |
| 1-31 | Cl | Cl | Cl | Cl | H | EtCO |
| 1-32 | Cl | Cl | Cl | Cl | H | n-PrCO |
| 1-33 | Cl | Cl | Cl | Cl | H | cyclo-PrCO |
| 1-34 | Cl | Cl | Cl | Cl | H | cyclo-PrCH$_2$CO |
| 1-35 | Cl | Cl | Cl | Cl | H | $CF_3CH_2CO$ |
| 1-36 | Cl | Cl | Cl | Cl | H | $CH_3SCH_2CO$ |
| 1-37 | Cl | Cl | Cl | Cl | H | $CH_3SOCH_2CO$ |
| 1-38 | Cl | Cl | Cl | Cl | H | $CH_3SO_2CH_2CO$ |
| 1-39 | Cl | Cl | Cl | Cl | H | $CH_3OCH_2CH_2CO$ |
| 1-40 | Cl | Cl | Cl | Cl | H | $CH_3OCH(Me)CH_2CO$ |
| 1-41 | Cl | Cl | Cl | Cl | H | EtNHCO |
| 1-42 | Cl | Cl | Cl | Cl | H | tert-BuOC(=O) |
| 1-43 | Cl | Cl | Cl | Me | H | H |
| 1-44 | Cl | Cl | Cl | Me | H | MeCO |
| 1-45 | Cl | Cl | Cl | Me | H | EtCO |
| 1-46 | Cl | Cl | Cl | Me | H | n-PrCO |
| 1-47 | Cl | Cl | Cl | Me | H | cyclo-PrCO |
| 1-48 | Cl | Cl | Cl | Me | H | cyclo-PrCH$_2$CO |
| 1-49 | Cl | Cl | Cl | Me | H | $CF_3CH_2CO$ |
| 1-50 | Cl | Cl | Cl | Me | H | $CH_3SCH_2CO$ |
| 1-51 | Cl | Cl | Cl | Me | H | $CH_3SOCH_2CO$ |
| 1-52 | Cl | Cl | Cl | Me | H | $CH_3SO_2CH_2CO$ |
| 1-53 | Cl | Cl | Cl | Me | H | $CH_3OCH_2CH_2CO$ |
| 1-54 | Cl | Cl | Cl | Me | H | $CH_3OCH(Me)CH_2CO$ |
| 1-55 | Cl | Cl | Cl | Me | H | EtNHCO |
| 1-56 | Cl | Cl | Cl | Me | H | tert-BuOC(=O) |
| 1-57 | Cl | Cl | Cl | H | H | H |
| 1-58 | Cl | Cl | Cl | H | H | MeCO |
| 1-59 | Cl | Cl | Cl | H | H | EtCO |
| 1-60 | Cl | Cl | Cl | H | H | n-PrCO |
| 1-61 | Cl | Cl | Cl | H | H | cyclo-PrCO |
| 1-62 | Cl | Cl | Cl | H | H | cyclo-PrCH$_2$CO |
| 1-63 | Cl | Cl | Cl | H | H | $CF_3CH_2CO$ |
| 1-64 | Cl | Cl | Cl | H | H | $CH_3SCH_2CO$ |
| 1-65 | Cl | Cl | Cl | H | H | $CH_3SOCH_2CO$ |
| 1-66 | Cl | Cl | Cl | H | H | $CH_3SO_2CH_2CO$ |
| 1-67 | Cl | Cl | Cl | H | H | $CH_3OCH_2CH_2CO$ |
| 1-68 | Cl | Cl | Cl | H | H | $CH_3OCH(Me)CH_2CO$ |
| 1-69 | Cl | Cl | Cl | H | H | EtNHCO |
| 1-70 | Cl | Cl | Cl | H | H | tert-BuOC(=O) |
| 1-71 | $CF_3$ | H | H | $CF_3$ | H | H |
| 1-72 | $CF_3$ | H | H | $CF_3$ | H | MeCO |
| 1-73 | $CF_3$ | H | H | $CF_3$ | H | EtCO |
| 1-74 | $CF_3$ | H | H | $CF_3$ | H | n-PrCO |
| 1-75 | $CF_3$ | H | H | $CF_3$ | H | cyclo-PrCO |
| 1-76 | $CF_3$ | H | H | $CF_3$ | H | cyclo-PrCH$_2$CO |
| 1-77 | $CF_3$ | H | H | $CF_3$ | H | $CF_3CH_2CO$ |
| 1-78 | $CF_3$ | H | H | $CF_3$ | H | $CH_3SCH_2CO$ |
| 1-79 | $CF_3$ | H | H | $CF_3$ | H | $CH_3SOCH_2CO$ |
| 1-80 | $CF_3$ | H | H | $CF_3$ | H | $CH_3SO_2CH_2CO$ |
| 1-81 | $CF_3$ | H | H | $CF_3$ | H | $CH_3OCH_2CH_2CO$ |
| 1-82 | $CF_3$ | H | H | $CF_3$ | H | $CH_3OCH(Me)CH_2CO$ |
| 1-83 | $CF_3$ | H | H | $CF_3$ | H | EtNHCO |
| 1-84 | $CF_3$ | H | H | $CF_3$ | H | tert-BuOC(=O) |
| 1-85 | $CF_3$ | H | H | Cl | H | H |
| 1-86 | $CF_3$ | H | H | Cl | H | MeCO |
| 1-87 | $CF_3$ | H | H | Cl | H | EtCO |
| 1-88 | $CF_3$ | H | H | Cl | H | n-PrCO |
| 1-89 | $CF_3$ | H | H | Cl | H | cyclo-PrCO |
| 1-90 | $CF_3$ | H | H | Cl | H | cyclo-PrCH$_2$CO |
| 1-91 | $CF_3$ | H | H | Cl | H | $CF_3CH_2CO$ |
| 1-92 | $CF_3$ | H | H | Cl | H | $CH_3SCH_2CO$ |
| 1-93 | $CF_3$ | H | H | Cl | H | $CH_3SOCH_2CO$ |
| 1-94 | $CF_3$ | H | H | Cl | H | $CH_3SO_2CH_2CO$ |
| 1-95 | $CF_3$ | H | H | Cl | H | $CH_3OCH_2CH_2CO$ |
| 1-96 | $CF_3$ | H | H | Cl | H | $CH_3OCH(Me)CH_2CO$ |
| 1-97 | $CF_3$ | H | H | Cl | H | EtNHCO |
| 1-98 | $CF_3$ | H | H | Cl | H | tert-BuOC(=O) |
| 1-99 | $CF_3$ | H | H | Me | H | H |
| 1-100 | $CF_3$ | H | H | Me | H | MeCO |
| 1-101 | $CF_3$ | H | H | Me | H | EtCO |
| 1-102 | $CF_3$ | H | H | Me | H | n-PrCO |
| 1-103 | $CF_3$ | H | H | Me | H | cyclo-PrCO |
| 1-104 | $CF_3$ | H | H | Me | H | cyclo-PrCH$_2$CO |
| 1-105 | $CF_3$ | H | H | Me | H | $CF_3CH_2CO$ |
| 1-106 | $CF_3$ | H | H | Me | H | $CH_3SCH_2CO$ |
| 1-107 | $CF_3$ | H | H | Me | H | $CH_3SOCH_2CO$ |
| 1-108 | $CF_3$ | H | H | Me | H | $CH_3SO_2CH_2CO$ |
| 1-109 | $CF_3$ | H | H | Me | H | $CH_3OCH_2CH_2CO$ |
| 1-110 | $CF_3$ | H | H | Me | H | $CH_3OCH(Me)CH_2CO$ |
| 1-111 | $CF_3$ | H | H | Me | H | EtNHCO |
| 1-112 | $CF_3$ | H | H | Me | H | tert-BuOC(=O) |
| 1-113 | $CF_3$ | H | H | H | H | H |
| 1-114 | $CF_3$ | H | H | H | H | MeCO |
| 1-115 | $CF_3$ | H | H | H | H | EtCO |
| 1-116 | $CF_3$ | H | H | H | H | n-PrCO |
| 1-117 | $CF_3$ | H | H | H | H | cyclo-PrCO |
| 1-118 | $CF_3$ | H | H | H | H | cyclo-PrCH$_2$CO |
| 1-119 | $CF_3$ | H | H | H | H | $CF_3CH_2CO$ |
| 1-120 | $CF_3$ | H | H | H | H | $CH_3SCH_2CO$ |
| 1-121 | $CF_3$ | H | H | H | H | $CH_3SOCH_2CO$ |
| 1-122 | $CF_3$ | H | H | H | H | $CH_3SO_2CH_2CO$ |
| 1-123 | $CF_3$ | H | H | H | H | $CH_3OCH_2CH_2CO$ |
| 1-124 | $CF_3$ | H | H | H | H | $CH_3OCH(Me)CH_2CO$ |
| 1-125 | $CF_3$ | H | H | H | H | EtNHCO |
| 1-126 | $CF_3$ | H | H | H | H | tert-BuOC(=O) |
| 1-127 | $CF_3$ | H | $CF_3$ | $CF_3$ | H | H |
| 1-128 | $CF_3$ | H | $CF_3$ | $CF_3$ | H | MeCO |
| 1-129 | $CF_3$ | H | $CF_3$ | $CF_3$ | H | EtCO |
| 1-130 | $CF_3$ | H | $CF_3$ | $CF_3$ | H | n-PrCO |
| 1-131 | $CF_3$ | H | $CF_3$ | $CF_3$ | H | cyclo-PrCO |
| 1-132 | $CF_3$ | H | $CF_3$ | $CF_3$ | H | cyclo-PrCH$_2$CO |
| 1-133 | $CF_3$ | H | $CF_3$ | $CF_3$ | H | $CF_3CH_2CO$ |
| 1-134 | $CF_3$ | H | $CF_3$ | $CF_3$ | H | $CH_3SCH_2CO$ |
| 1-135 | $CF_3$ | H | $CF_3$ | $CF_3$ | H | $CH_3SOCH_2CO$ |
| 1-136 | $CF_3$ | H | $CF_3$ | $CF_3$ | H | $CH_3SO_2CH_2CO$ |
| 1-137 | $CF_3$ | H | $CF_3$ | $CF_3$ | H | $CH_3OCH_2CH_2CO$ |
| 1-138 | $CF_3$ | H | $CF_3$ | $CF_3$ | H | $CH_3OCH(Me)CH_2CO$ |
| 1-139 | $CF_3$ | H | $CF_3$ | $CF_3$ | H | EtNHCO |
| 1-140 | $CF_3$ | H | $CF_3$ | $CF_3$ | H | tert-BuOC(=O) |
| 1-141 | $CF_3$ | H | $CF_3$ | Cl | H | H |
| 1-142 | $CF_3$ | H | $CF_3$ | Cl | H | MeCO |
| 1-143 | $CF_3$ | H | $CF_3$ | Cl | H | EtCO |
| 1-144 | $CF_3$ | H | $CF_3$ | Cl | H | n-PrCO |
| 1-145 | $CF_3$ | H | $CF_3$ | Cl | H | cyclo-PrCO |
| 1-146 | $CF_3$ | H | $CF_3$ | Cl | H | cyclo-PrCH$_2$CO |
| 1-147 | $CF_3$ | H | $CF_3$ | Cl | H | $CF_3CH_2CO$ |
| 1-148 | $CF_3$ | H | $CF_3$ | Cl | H | $CH_3SCH_2CO$ |
| 1-149 | $CF_3$ | H | $CF_3$ | Cl | H | $CH_3SOCH_2CO$ |
| 1-150 | $CF_3$ | H | $CF_3$ | Cl | H | $CH_3SO_2CH_2CO$ |
| 1-151 | $CF_3$ | H | $CF_3$ | Cl | H | $CH_3OCH_2CH_2CO$ |
| 1-152 | $CF_3$ | H | $CF_3$ | Cl | H | $CH_3OCH(Me)CH_2CO$ |
| 1-153 | $CF_3$ | H | $CF_3$ | Cl | H | EtNHCO |
| 1-154 | $CF_3$ | H | $CF_3$ | Cl | H | tert-BuOC(=O) |
| 1-155 | $CF_3$ | H | $CF_3$ | Me | H | H |
| 1-156 | $CF_3$ | H | $CF_3$ | Me | H | MeCO |

TABLE 1-continued

| Compound No. | $X^2$ | $X^3$ | $X^4$ | $Y^3$ | $R^1$ | $R^4$ |
|---|---|---|---|---|---|---|
| 1-157 | $CF_3$ | H | $CF_3$ | Me | H | EtCO |
| 1-158 | $CF_3$ | H | $CF_3$ | Me | H | n-PrCO |
| 1-159 | $CF_3$ | H | $CF_3$ | Me | H | cyclo-PrCO |
| 1-160 | $CF_3$ | H | $CF_3$ | Me | H | cyclo-PrCH$_2$CO |
| 1-161 | $CF_3$ | H | $CF_3$ | Me | H | CF$_3$CH$_2$CO |
| 1-162 | $CF_3$ | H | $CF_3$ | Me | H | CH$_3$SCH$_2$CO |
| 1-163 | $CF_3$ | H | $CF_3$ | Me | H | CH$_3$SOCH$_2$CO |
| 1-164 | $CF_3$ | H | $CF_3$ | Me | H | CH$_3$SO$_2$CH$_2$CO |
| 1-165 | $CF_3$ | H | $CF_3$ | Me | H | CH$_3$OCH$_2$CH$_2$CO |
| 1-166 | $CF_3$ | H | $CF_3$ | Me | H | CH$_3$OCH(Me)CH$_2$CO |
| 1-167 | $CF_3$ | H | $CF_3$ | Me | H | EtNHCO |
| 1-168 | $CF_3$ | H | $CF_3$ | Me | H | tert-BuOC(=O) |
| 1-169 | $CF_3$ | H | $CF_3$ | H | H | H |
| 1-170 | $CF_3$ | H | $CF_3$ | H | H | MeCO |
| 1-171 | $CF_3$ | H | $CF_3$ | H | H | EtCO |
| 1-172 | $CF_3$ | H | $CF_3$ | H | H | n-PrCO |
| 1-173 | $CF_3$ | H | $CF_3$ | H | H | cyclo-PrCO |
| 1-174 | $CF_3$ | H | $CF_3$ | H | H | cyclo-PrCH$_2$CO |
| 1-175 | $CF_3$ | H | $CF_3$ | H | H | CF$_3$CH$_2$CO |
| 1-176 | $CF_3$ | H | $CF_3$ | H | H | CH$_3$SCH$_2$CO |
| 1-177 | $CF_3$ | H | $CF_3$ | H | H | CH$_3$SOCH$_2$CO |
| 1-178 | $CF_3$ | H | $CF_3$ | H | H | CH$_3$SO$_2$CH$_2$CO |
| 1-179 | $CF_3$ | H | $CF_3$ | H | H | CH$_3$OCH$_2$CH$_2$CO |
| 1-180 | $CF_3$ | H | $CF_3$ | H | H | CH$_3$OCH(Me)CH$_2$CO |
| 1-181 | $CF_3$ | H | $CF_3$ | H | H | EtNHCO |
| 1-182 | $CF_3$ | H | $CF_3$ | H | H | tert-BuOC(=O) |
| 1-183 | Cl | Cl | $CF_3$ | $CF_3$ | H | H |
| 1-184 | Cl | Cl | $CF_3$ | $CF_3$ | H | MeCO |
| 1-185 | Cl | Cl | $CF_3$ | $CF_3$ | H | EtCO |
| 1-186 | Cl | Cl | $CF_3$ | $CF_3$ | H | cyclo-PrCO |
| 1-187 | Cl | Cl | $CF_3$ | $CF_3$ | H | CH$_3$SCH$_2$CO |
| 1-188 | Cl | Cl | $CF_3$ | $CF_3$ | H | CF$_3$CH$_2$CO |
| 1-189 | Cl | Cl | $CF_3$ | $CF_3$ | H | EtNHCO |
| 1-190 | Cl | Cl | $CF_3$ | $CF_3$ | H | tert-BuOC(=O) |
| 1-191 | Cl | H | $CF_3$ | $CF_3$ | H | H |
| 1-192 | Cl | H | $CF_3$ | $CF_3$ | H | MeCO |
| 1-193 | Cl | H | $CF_3$ | $CF_3$ | H | EtCO |
| 1-194 | Cl | H | $CF_3$ | $CF_3$ | H | cyclo-PrCO |
| 1-195 | Cl | H | $CF_3$ | $CF_3$ | H | CH$_3$SCH$_2$CO |
| 1-196 | Cl | H | $CF_3$ | $CF_3$ | H | CF$_3$CH$_2$CO |
| 1-197 | Cl | H | $CF_3$ | $CF_3$ | H | EtNHCO |
| 1-198 | Cl | H | $CF_3$ | $CF_3$ | H | tert-BuOC(=O) |
| 1-199 | F | H | $CF_3$ | $CF_3$ | H | H |
| 1-200 | F | H | $CF_3$ | $CF_3$ | H | MeCO |
| 1-201 | F | H | $CF_3$ | $CF_3$ | H | EtCO |
| 1-202 | F | H | $CF_3$ | $CF_3$ | H | cyclo-PrCO |
| 1-203 | F | H | $CF_3$ | $CF_3$ | H | CH$_3$SCH$_2$CO |
| 1-204 | F | H | $CF_3$ | $CF_3$ | H | CF$_3$CH$_2$CO |
| 1-205 | F | H | $CF_3$ | $CF_3$ | H | EtNHCO |
| 1-206 | F | H | $CF_3$ | $CF_3$ | H | tert-BuOC(=O) |
| 1-207 | H | F | $CF_3$ | $CF_3$ | H | H |
| 1-208 | H | F | $CF_3$ | $CF_3$ | H | MeCO |
| 1-209 | H | F | $CF_3$ | $CF_3$ | H | EtCO |
| 1-210 | H | F | $CF_3$ | $CF_3$ | H | cyclo-PrCO |
| 1-211 | H | F | $CF_3$ | $CF_3$ | H | CH$_3$SCH$_2$CO |
| 1-212 | H | F | $CF_3$ | $CF_3$ | H | CF$_3$CH$_2$CO |
| 1-213 | H | F | $CF_3$ | $CF_3$ | H | EtNHCO |
| 1-214 | H | F | $CF_3$ | $CF_3$ | H | tert-BuOC(=O) |
| 1-215 | Cl | H | Cl | Br | H | H |
| 1-216 | Cl | H | Cl | Br | H | MeCO |
| 1-217 | Cl | H | Cl | Br | H | EtCO |
| 1-218 | Cl | H | Cl | Br | H | n-PrCO |
| 1-219 | Cl | H | Cl | Br | H | cyclo-PrCO |
| 1-220 | Cl | H | Cl | Br | H | cyclo-PrCH$_2$CO |
| 1-221 | Cl | H | Cl | Br | H | CF$_3$CH$_2$CO |
| 1-222 | Cl | H | Cl | Br | H | CH$_3$SCH$_2$CO |
| 1-223 | Cl | H | Cl | Br | H | CH$_3$SOCH$_2$CO |
| 1-224 | Cl | H | Cl | Br | H | CH$_3$SO$_2$CH$_2$CO |
| 1-225 | Cl | H | Cl | Br | H | CH$_3$OCH$_2$CH$_2$CO |
| 1-226 | Cl | H | Cl | Br | H | CH$_3$OCH(Me)CH$_2$CO |
| 1-227 | Cl | H | Cl | Br | H | EtNHCO |
| 1-228 | Cl | H | Cl | Br | H | tert-BuOC(=O) |
| 1-229 | Cl | Cl | Cl | Br | H | H |
| 1-230 | Cl | Cl | Cl | Br | H | MeCO |
| 1-231 | Cl | Cl | Cl | Br | H | EtCO |
| 1-232 | Cl | Cl | Cl | Br | H | n-PrCO |
| 1-233 | Cl | Cl | Cl | Br | H | cyclo-PrCO |
| 1-234 | Cl | Cl | Cl | Br | H | cyclo-PrCH$_2$CO |
| 1-235 | Cl | Cl | Cl | Br | H | CF$_3$CH$_2$CO |
| 1-236 | Cl | Cl | Cl | Br | H | CH$_3$SCH$_2$CO |
| 1-237 | Cl | Cl | Cl | Br | H | CH$_3$SOCH$_2$CO |
| 1-238 | Cl | Cl | Cl | Br | H | CH$_3$SO$_2$CH$_2$CO |
| 1-239 | Cl | Cl | Cl | Br | H | CH$_3$OCH$_2$CH$_2$CO |
| 1-240 | Cl | Cl | Cl | Br | H | CH$_3$OCH(Me)CH$_2$CO |
| 1-241 | Cl | Cl | Cl | Br | H | EtNHCO |
| 1-242 | Cl | Cl | Cl | Br | H | tert-BuOC(=O) |
| 1-243 | $CF_3$ | H | H | Br | H | H |
| 1-244 | $CF_3$ | H | H | Br | H | MeCO |
| 1-245 | $CF_3$ | H | H | Br | H | EtCO |
| 1-246 | $CF_3$ | H | H | Br | H | n-PrCO |
| 1-247 | $CF_3$ | H | H | Br | H | cyclo-PrCO |
| 1-248 | $CF_3$ | H | H | Br | H | cyclo-PrCH$_2$CO |
| 1-249 | $CF_3$ | H | H | Br | H | CF$_3$CH$_2$CO |
| 1-250 | $CF_3$ | H | H | Br | H | CH$_3$SCH$_2$CO |
| 1-251 | $CF_3$ | H | H | Br | H | CH$_3$SOCH$_2$CO |
| 1-252 | $CF_3$ | H | H | Br | H | CH$_3$SO$_2$CH$_2$CO |
| 1-253 | $CF_3$ | H | H | Br | H | CH$_3$OCH$_2$CH$_2$CO |
| 1-254 | $CF_3$ | H | H | Br | H | CH$_3$OCH(Me)CH$_2$CO |
| 1-255 | $CF_3$ | H | H | Br | H | EtNHCO |
| 1-256 | $CF_3$ | H | H | Br | H | tert-BuOC(=O) |
| 1-257 | $CF_3$ | H | $CF_3$ | Br | H | H |
| 1-258 | $CF_3$ | H | $CF_3$ | Br | H | MeCO |
| 1-259 | $CF_3$ | H | $CF_3$ | Br | H | EtCO |
| 1-260 | $CF_3$ | H | $CF_3$ | Br | H | n-PrCO |
| 1-261 | $CF_3$ | H | $CF_3$ | Br | H | cyclo-PrCO |
| 1-262 | $CF_3$ | H | $CF_3$ | Br | H | cyclo-PrCH$_2$CO |
| 1-263 | $CF_3$ | H | $CF_3$ | Br | H | CF$_3$CH$_2$CO |
| 1-264 | $CF_3$ | H | $CF_3$ | Br | H | CH$_3$SCH$_2$CO |
| 1-265 | $CF_3$ | H | $CF_3$ | Br | H | CH$_3$SOCH$_2$CO |
| 1-266 | $CF_3$ | H | $CF_3$ | Br | H | CH$_3$SO$_2$CH$_2$CO |
| 1-267 | $CF_3$ | H | $CF_3$ | Br | H | CH$_3$OCH$_2$CH$_2$CO |
| 1-268 | $CF_3$ | H | $CF_3$ | Br | H | CH$_3$OCH(Me)CH$_2$CO |
| 1-269 | $CF_3$ | H | $CF_3$ | Br | H | EtNHCO |
| 1-270 | $CF_3$ | H | $CF_3$ | Br | H | tert-BuOC(=O) |
| 1-271 | Br | H | Br | $CF_3$ | H | H |
| 1-272 | Br | H | Br | $CF_3$ | H | MeCO |
| 1-273 | Br | H | Br | $CF_3$ | H | EtCO |
| 1-274 | Br | H | Br | $CF_3$ | H | n-PrCO |
| 1-275 | Br | H | Br | $CF_3$ | H | cyclo-PrCO |
| 1-276 | Br | H | Br | $CF_3$ | H | cyclo-PrCH$_2$CO |
| 1-277 | Br | H | Br | $CF_3$ | H | CF$_3$CH$_2$CO |
| 1-278 | Br | H | Br | $CF_3$ | H | CH$_3$SCH$_2$CO |
| 1-279 | Br | H | Br | $CF_3$ | H | CH$_3$SOCH$_2$CO |
| 1-280 | Br | H | Br | $CF_3$ | H | CH$_3$SO$_2$CH$_2$CO |
| 1-281 | Br | H | Br | $CF_3$ | H | CH$_3$OCH$_2$CH$_2$CO |
| 1-282 | Br | H | Br | $CF_3$ | H | CH$_3$OCH(Me)CH$_2$CO |
| 1-283 | Br | H | Br | $CF_3$ | H | EtNHCO |
| 1-284 | Br | H | Br | $CF_3$ | H | tert-BuOC(=O) |
| 1-285 | Br | H | Br | Cl | H | H |
| 1-286 | Br | H | Br | Cl | H | MeCO |
| 1-287 | Br | H | Br | Cl | H | EtCO |
| 1-288 | Br | H | Br | Cl | H | n-PrCO |
| 1-289 | Br | H | Br | Cl | H | cyclo-PrCO |
| 1-290 | Br | H | Br | Cl | H | cyclo-PrCH$_2$CO |
| 1-291 | Br | H | Br | Cl | H | CF$_3$CH$_2$CO |
| 1-292 | Br | H | Br | Cl | H | CH$_3$SCH$_2$CO |
| 1-293 | Br | H | Br | Cl | H | CH$_3$SOCH$_2$CO |
| 1-294 | Br | H | Br | Cl | H | CH$_3$SO$_2$CH$_2$CO |
| 1-295 | Br | H | Br | Cl | H | CH$_3$OCH$_2$CH$_2$CO |
| 1-296 | Br | H | Br | Cl | H | CH$_3$OCH(Me)CH$_2$CO |
| 1-297 | Br | H | Br | Cl | H | EtNHCO |
| 1-298 | Br | H | Br | Cl | H | tert-BuOC(=O) |
| 1-299 | Br | H | Br | Br | H | H |
| 1-300 | Br | H | Br | Br | H | MeCO |
| 1-301 | Br | H | Br | Br | H | EtCO |
| 1-302 | Br | H | Br | Br | H | n-PrCO |
| 1-303 | Br | H | Br | Br | H | cyclo-PrCO |
| 1-304 | Br | H | Br | Br | H | cyclo-PrCH$_2$CO |
| 1-305 | Br | H | Br | Br | H | CF$_3$CH$_2$CO |
| 1-306 | Br | H | Br | Br | H | CH$_3$SCH$_2$CO |
| 1-307 | Br | H | Br | Br | H | CH$_3$SOCH$_2$CO |
| 1-308 | Br | H | Br | Br | H | CH$_3$SO$_2$CH$_2$CO |
| 1-309 | Br | H | Br | Br | H | CH$_3$OCH$_2$CH$_2$CO |
| 1-310 | Br | H | Br | Br | H | CH$_3$OCH(Me)CH$_2$CO |
| 1-311 | Br | H | Br | Br | H | EtNHCO |
| 1-312 | Br | H | Br | Br | H | tert-BuOC(=O) |

TABLE 1-continued

| Compound No. | X² | X³ | X⁴ | Y³ | R¹ | R⁴ |
|---|---|---|---|---|---|---|
| 1-313 | Br | H | Br | Me | H | H |
| 1-314 | Br | H | Br | Me | H | MeCO |
| 1-315 | Br | H | Br | Me | H | EtCO |
| 1-316 | Br | H | Br | Me | H | n-PrCO |
| 1-317 | Br | H | Br | Me | H | cyclo-PrCO |
| 1-318 | Br | H | Br | Me | H | cyclo-PrCH₂CO |
| 1-319 | Br | H | Br | Me | H | CF₃CH₂CO |
| 1-320 | Br | H | Br | Me | H | CH₃SCH₂CO |
| 1-321 | Br | H | Br | Me | H | CH₃SOCH₂CO |
| 1-322 | Br | H | Br | Me | H | CH₃SO₂CH₂CO |
| 1-323 | Br | H | Br | Me | H | CH₃OCH₂CH₂CO |
| 1-324 | Br | H | Br | Me | H | CH₃OCH(Me)CH₂CO |
| 1-325 | Br | H | Br | Me | H | EtNHCO |
| 1-326 | Br | H | Br | Me | H | tert-BuOC(=O) |
| 1-327 | Br | H | Br | H | H | H |
| 1-328 | Br | H | Br | H | H | MeCO |
| 1-329 | Br | H | Br | H | H | EtCO |
| 1-330 | Br | H | Br | H | H | n-PrCO |
| 1-331 | Br | H | Br | H | H | cyclo-PrCO |
| 1-332 | Br | H | Br | H | H | cyclo-PrCH₂CO |
| 1-333 | Br | H | Br | H | H | CF₃CH₂CO |
| 1-334 | Br | H | Br | H | H | CH₃SCH₂CO |
| 1-335 | Br | H | Br | H | H | CH₃SOCH₂CO |
| 1-336 | Br | H | Br | H | H | CH₃SO₂CH₂CO |
| 1-337 | Br | H | Br | H | H | CH₃OCH₂CH₂CO |
| 1-338 | Br | H | Br | H | H | CH₃OCH(Me)CH₂CO |
| 1-339 | Br | H | Br | H | H | EtNHCO |
| 1-340 | Br | H | Br | H | H | tert-BuOC(=O) |
| 1-341 | Cl | H | Cl | H | Me | H |
| 1-342 | Cl | H | Cl | H | Me | MeCO |
| 1-343 | Cl | H | Cl | H | Me | EtCO |
| 1-344 | Cl | H | Cl | H | Me | n-PrCO |
| 1-345 | Cl | H | Cl | H | Me | cyclo-PrCO |
| 1-345-a | Cl | H | Cl | H | Me | cyclo-PrCO |
| 1-346 | Cl | H | Cl | H | Me | cyclo-PrCH₂CO |
| 1-347 | Cl | H | Cl | H | Me | CF₃CH₂CO |
| 1-348 | Cl | H | Cl | H | Me | CH₃SCH₂CO |
| 1-349 | Cl | H | Cl | H | Me | CH₃SOCH₂CO |
| 1-350 | Cl | H | Cl | H | Me | CH₃SO₂CH₂CO |
| 1-351 | Cl | H | Cl | H | Me | CH₃OCH₂CH₂CO |
| 1-352 | Cl | H | Cl | H | Me | CH₃OCH(Me)CH₂CO |
| 1-353 | Cl | H | Cl | H | Me | EtNHCO |
| 1-354 | Cl | H | Cl | H | Me | tert-BuOC(=O) |
| 1-355 | Br | H | Br | H | Me | H |
| 1-356 | Br | H | Br | H | Me | MeCO |
| 1-357 | Br | H | Br | H | Me | EtCO |
| 1-358 | Br | H | Br | H | Me | n-PrCO |
| 1-359 | Br | H | Br | H | Me | cyclo-PrCO |
| 1-360 | Br | H | Br | H | Me | cyclo-PrCH₂CO |
| 1-361 | Br | H | Br | H | Me | CF₃CH₂CO |
| 1-362 | Br | H | Br | H | Me | CH₃SCH₂CO |
| 1-363 | Br | H | Br | H | Me | CH₃SOCH₂CO |
| 1-364 | Br | H | Br | H | Me | CH₃SO₂CH₂CO |
| 1-365 | Br | H | Br | H | Me | CH₃OCH₂CH₂CO |
| 1-366 | Br | H | Br | H | Me | CH₃OCH(Me)CH₂CO |
| 1-367 | Br | H | Br | H | Me | EtNHCO |
| 1-368 | Br | H | Br | H | Me | tert-BuOC(=O) |
| 1-369 | Cl | Cl | Cl | H | Me | H |
| 1-370 | Cl | Cl | Cl | H | Me | MeCO |
| 1-370-a | Cl | Cl | Cl | H | Me | MeCO |
| 1-371 | Cl | Cl | Cl | H | Me | EtCO |
| 1-371-a | Cl | Cl | Cl | H | Me | EtCO |
| 1-371-b | Cl | Cl | Cl | H | Me | EtCO |
| 1-372 | Cl | Cl | Cl | H | Me | n-PrCO |
| 1-373 | Cl | Cl | Cl | H | Me | cyclo-PrCO |
| 1-373-a | Cl | Cl | Cl | H | Me | cyclo-PrCO |
| 1-374 | Cl | Cl | Cl | H | Me | cyclo-PrCH₂CO |
| 1-374-a | Cl | Cl | Cl | H | Me | cyclo-PrCH₂CO |
| 1-375 | Cl | Cl | Cl | H | Me | CF₃CH₂CO |
| 1-375-a | Cl | Cl | Cl | H | Me | CF₃CH₂CO |
| 1-376 | Cl | Cl | Cl | H | Me | CH₃SCH₂CO |
| 1-377 | Cl | Cl | Cl | H | Me | CH₃SOCH₂CO |
| 1-378 | Cl | Cl | Cl | H | Me | CH₃SO₂CH₂CO |
| 1-379 | Cl | Cl | Cl | H | Me | CH₃OCH₂CH₂CO |
| 1-379-a | Cl | Cl | Cl | H | Me | CH₃OCH₂CH₂CO |
| 1-380 | Cl | Cl | Cl | H | Me | CH₃OCH(Me)CH₂CO |
| 1-381 | Cl | Cl | Cl | H | Me | EtNHCO |
| 1-382 | Cl | Cl | Cl | H | Me | tert-BuOC(=O) |
| 1-383 | CF₃ | H | H | H | Me | H |
| 1-384 | CF₃ | H | H | H | Me | MeCO |
| 1-385 | CF₃ | H | H | H | Me | EtCO |
| 1-386 | CF₃ | H | H | H | Me | n-PrCO |
| 1-387 | CF₃ | H | H | H | Me | cyclo-PrCO |
| 1-388 | CF₃ | H | H | H | Me | cyclo-PrCH₂CO |
| 1-389 | CF₃ | H | H | H | Me | CF₃CH₂CO |
| 1-390 | CF₃ | H | H | H | Me | CH₃SCH₂CO |
| 1-391 | CF₃ | H | H | H | Me | CH₃SOCH₂CO |
| 1-392 | CF₃ | H | H | H | Me | CH₃SO₂CH₂CO |
| 1-393 | CF₃ | H | H | H | Me | CH₃OCH₂CH₂CO |
| 1-394 | CF₃ | H | H | H | Me | CH₃OCH(Me)CH₂CO |
| 1-395 | CF₃ | H | H | H | Me | EtNHCO |
| 1-396 | CF₃ | H | H | H | Me | tert-BuOC(=O) |
| 1-397 | CF₃ | H | CF₃ | H | Me | H |
| 1-398 | CF₃ | H | CF₃ | H | Me | MeCO |
| 1-398-a | CF₃ | H | CF₃ | H | Me | MeCO |
| 1-399 | CF₃ | H | CF₃ | H | Me | EtCO |
| 1-399-a | CF₃ | H | CF₃ | H | Me | EtCO |
| 1-399-b | CF₃ | H | CF₃ | H | Me | EtCO |
| 1-400 | CF₃ | H | CF₃ | H | Me | n-PrCO |
| 1-401 | CF₃ | H | CF₃ | H | Me | cyclo-PrCO |
| 1-401-a | CF₃ | H | CF₃ | H | Me | cyclo-PrCO |
| 1-402 | CF₃ | H | CF₃ | H | Me | cyclo-PrCH₂CO |
| 1-402-a | CF₃ | H | CF₃ | H | Me | cyclo-PrCH₂CO |
| 1-403 | CF₃ | H | CF₃ | H | Me | CF₃CH₂CO |
| 1-403-a | CF₃ | H | CF₃ | H | Me | CF₃CH₂CO |
| 1-404 | CF₃ | H | CF₃ | H | Me | CH₃SCH₂CO |
| 1-405 | CF₃ | H | CF₃ | H | Me | CH₃SOCH₂CO |
| 1-406 | CF₃ | H | CF₃ | H | Me | CH₃SO₂CH₂CO |
| 1-407 | CF₃ | H | CF₃ | H | Me | CH₃OCH₂CH₂CO |
| 1-407-a | CF₃ | H | CF₃ | H | Me | CH₃OCH₂CH₂CO |
| 1-408 | CF₃ | H | CF₃ | H | Me | CH₃OCH(Me)CH₂CO |
| 1-409 | CF₃ | H | CF₃ | H | Me | EtNHCO |
| 1-410 | CF₃ | H | CF₃ | H | Me | tert-BuOC(=O) |
| 1-411 | Cl | Cl | CF₃ | H | Me | H |
| 1-412 | Cl | Cl | CF₃ | H | Me | MeCO |
| 1-413 | Cl | Cl | CF₃ | H | Me | EtCO |
| 1-414 | Cl | Cl | CF₃ | H | Me | cyclo-PrCO |
| 1-415 | Cl | Cl | CF₃ | H | Me | CH₃SCH₂CO |
| 1-416 | Cl | Cl | CF₃ | H | Me | CF₃CH₂CO |
| 1-417 | Cl | Cl | CF₃ | H | Me | EtNHCO |
| 1-418 | Cl | Cl | CF₃ | H | Me | tert-BuOC(=O) |
| 1-419 | Cl | H | CF₃ | H | Me | H |
| 1-420 | Cl | H | CF₃ | H | Me | MeCO |
| 1-421 | Cl | H | CF₃ | H | Me | EtCO |
| 1-422 | Cl | H | CF₃ | H | Me | cyclo-PrCO |
| 1-423 | Cl | H | CF₃ | H | Me | CH₃SCH₂CO |
| 1-424 | Cl | H | CF₃ | H | Me | CF₃CH₂CO |
| 1-425 | Cl | H | CF₃ | H | Me | EtNHCO |
| 1-426 | Cl | H | CF₃ | H | Me | tert-BuOC(=O) |
| 1-427 | F | H | CF₃ | H | Me | H |
| 1-428 | F | H | CF₃ | H | Me | MeCO |
| 1-429 | F | H | CF₃ | H | Me | EtCO |
| 1-430 | F | H | CF₃ | H | Me | cyclo-PrCO |
| 1-431 | F | H | CF₃ | H | Me | CH₃SCH₂CO |
| 1-432 | F | H | CF₃ | H | Me | CF₃CH₂CO |
| 1-433 | F | H | CF₃ | H | Me | EtNHCO |
| 1-434 | F | H | CF₃ | H | Me | tert-BuOC(=O) |
| 1-435 | H | F | CF₃ | H | Me | H |
| 1-436 | H | F | CF₃ | H | Me | MeCO |
| 1-437 | H | F | CF₃ | H | Me | EtCO |
| 1-438 | H | F | CF₃ | H | Me | cyclo-PrCO |
| 1-439 | H | F | CF₃ | H | Me | CH₃SCH₂CO |
| 1-440 | H | F | CF₃ | H | Me | CF₃CH₂CO |
| 1-441 | H | F | CF₃ | H | Me | EtNHCO |
| 1-442 | H | F | CF₃ | H | Me | tert-BuOC(=O) |
| 1-443 | OCF₃ | H | H | CF₃ | H | EtCO |
| 1-444 | SCF₃ | H | H | CF₃ | H | EtCO |
| 1-445 | SOCF₃ | H | H | CF₃ | H | EtCO |
| 1-446 | SO₂CF₃ | H | H | CF₃ | H | EtCO |

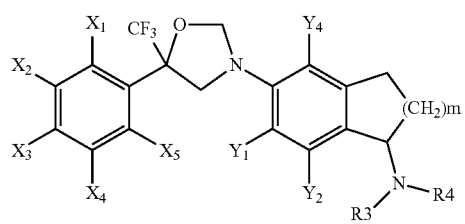

Wherein, $X^1$, $X^5$, $Y^1$, $Y^2$, $Y^4$ and $R^3$ represent hydrogen.

TABLE 2

| Compound No. | $X^2$ | $X^3$ | $X^4$ | $R^4$ | m |
|---|---|---|---|---|---|
| 2-1 | Cl | H | Cl | H | 1 |
| 2-2 | Cl | H | Cl | MeCO | 1 |
| 2-3 | Cl | H | Cl | EtCO | 1 |
| 2-4 | Cl | H | Cl | n-PrCO | 1 |
| 2-5 | Cl | H | Cl | cyclo-PrCO | 1 |
| 2-6 | Cl | H | Cl | cyclo-PrCH$_2$CO | 1 |
| 2-7 | Cl | H | Cl | CF$_3$CH$_2$CO | 1 |
| 2-8 | Cl | H | Cl | CH$_3$SCH$_2$CO | 1 |
| 2-9 | Cl | H | Cl | CH$_3$SOCH$_2$CO | 1 |
| 2-10 | Cl | H | Cl | CH$_3$SO$_2$CH$_2$CO | 1 |
| 2-11 | Cl | H | Cl | CH$_3$OCH$_2$CH$_2$CO | 1 |
| 2-12 | Cl | H | Cl | CH$_3$OCH(Me)CH$_2$CO | 1 |
| 2-13 | Cl | H | Cl | EtNHCO | 1 |
| 2-14 | Cl | H | Cl | tert-BuOC(=O) | 1 |
| 2-15 | Br | H | Br | H | 1 |
| 2-16 | Br | H | Br | MeCO | 1 |
| 2-17 | Br | H | Br | EtCO | 1 |
| 2-18 | Br | H | Br | n-PrCO | 1 |
| 2-19 | Br | H | Br | cyclo-PrCO | 1 |
| 2-20 | Br | H | Br | cyclo-PrCH$_2$CO | 1 |
| 2-21 | Br | H | Br | CF$_3$CH$_2$CO | 1 |
| 2-22 | Br | H | Br | CH$_3$SCH$_2$CO | 1 |
| 2-23 | Br | H | Br | CH$_3$SOCH$_2$CO | 1 |
| 2-24 | Br | H | Br | CH$_3$SO$_2$CH$_2$CO | 1 |
| 2-25 | Br | H | Br | CH$_3$OCH$_2$CH$_2$CO | 1 |
| 2-26 | Br | H | Br | CH$_3$OCH(Me)CH$_2$CO | 1 |
| 2-27 | Br | H | Br | EtNHCO | 1 |
| 2-28 | Br | H | Br | tert-BuOC(=O) | 1 |
| 2-29 | Cl | Cl | Cl | H | 1 |
| 2-30 | Cl | Cl | Cl | MeCO | 1 |
| 2-31 | Cl | Cl | Cl | EtCO | 1 |
| 2-32 | Cl | Cl | Cl | n-PrCO | 1 |
| 2-33 | Cl | Cl | Cl | cyclo-PrCO | 1 |
| 2-34 | Cl | Cl | Cl | cyclo-PrCH$_2$CO | 1 |
| 2-35 | Cl | Cl | Cl | CF$_3$CH$_2$CO | 1 |
| 2-36 | Cl | Cl | Cl | CH$_3$SCH$_2$CO | 1 |
| 2-37 | Cl | Cl | Cl | CH$_3$SOCH$_2$CO | 1 |
| 2-38 | Cl | Cl | Cl | CH$_3$SO$_2$CH$_2$CO | 1 |
| 2-39 | Cl | Cl | Cl | CH$_3$OCH$_2$CH$_2$CO | 1 |
| 2-40 | Cl | Cl | Cl | CH$_3$OCH(Me)CH$_2$CO | 1 |
| 2-41 | Cl | Cl | Cl | EtNHCO | 1 |
| 2-42 | Cl | Cl | Cl | tert-BuOC(=O) | 1 |
| 2-43 | CF$_3$ | H | H | H | 1 |
| 2-44 | CF$_3$ | H | H | MeCO | 1 |
| 2-45 | CF$_3$ | H | H | EtCO | 1 |
| 2-46 | CF$_3$ | H | H | n-PrCO | 1 |
| 2-47 | CF$_3$ | H | H | cyclo-PrCO | 1 |
| 2-48 | CF$_3$ | H | H | cyclo-PrCH$_2$CO | 1 |
| 2-49 | CF$_3$ | H | H | CF$_3$CH$_2$CO | 1 |
| 2-50 | CF$_3$ | H | H | CH$_3$SCH$_2$CO | 1 |
| 2-51 | CF$_3$ | H | H | CH$_3$SOCH$_2$CO | 1 |
| 2-52 | CF$_3$ | H | H | CH$_3$SO$_2$CH$_2$CO | 1 |
| 2-53 | CF$_3$ | H | H | CH$_3$OCH$_2$CH$_2$CO | 1 |
| 2-54 | CF$_3$ | H | H | CH$_3$OCH(Me)CH$_2$CO | 1 |
| 2-55 | CF$_3$ | H | H | EtNHCO | 1 |
| 2-56 | CF$_3$ | H | H | tert-BuOC(=O) | 1 |
| 2-57 | CF$_3$ | H | CF$_3$ | H | 1 |
| 2-58 | CF$_3$ | H | CF$_3$ | MeCO | 1 |
| 2-59 | CF$_3$ | H | CF$_3$ | EtCO | 1 |
| 2-60 | CF$_3$ | H | CF$_3$ | n-PrCO | 1 |
| 2-61 | CF$_3$ | H | CF$_3$ | cyclo-PrCO | 1 |
| 2-62 | CF$_3$ | H | CF$_3$ | cyclo-PrCH$_2$CO | 1 |
| 2-63 | CF$_3$ | H | CF$_3$ | CF$_3$CH$_2$CO | 1 |
| 2-64 | CF$_3$ | H | CF$_3$ | CH$_3$SCH$_2$CO | 1 |
| 2-65 | CF$_3$ | H | CF$_3$ | CH$_3$SOCH$_2$CO | 1 |
| 2-66 | CF$_3$ | H | CF$_3$ | CH$_3$SO$_2$CH$_2$CO | 1 |
| 2-67 | CF$_3$ | H | CF$_3$ | CH$_3$OCH$_2$CH$_2$CO | 1 |
| 2-68 | CF$_3$ | H | CF$_3$ | CH$_3$OCH(Me)CH$_2$CO | 1 |
| 2-69 | CF$_3$ | H | CF$_3$ | EtNHCO | 1 |
| 2-70 | CF$_3$ | H | CF$_3$ | tert-BuOC(=O) | 1 |
| 2-71 | Cl | Cl | CF$_3$ | H | 1 |
| 2-72 | Cl | Cl | CF$_3$ | MeCO | 1 |
| 2-73 | Cl | Cl | CF$_3$ | EtCO | 1 |
| 2-74 | Cl | Cl | CF$_3$ | cyclo-PrCO | 1 |
| 2-75 | Cl | Cl | CF$_3$ | CH$_3$SCH$_2$CO | 1 |
| 2-76 | Cl | Cl | CF$_3$ | CF$_3$CH$_2$CO | 1 |
| 2-77 | Cl | Cl | CF$_3$ | EtNHCO | 1 |
| 2-78 | Cl | Cl | CF$_3$ | tert-BuOC(=O) | 1 |
| 2-79 | Cl | H | CF$_3$ | H | 1 |
| 2-80 | Cl | H | CF$_3$ | MeCO | 1 |
| 2-81 | Cl | H | CF$_3$ | EtCO | 1 |
| 2-82 | Cl | H | CF$_3$ | cyclo-PrCO | 1 |
| 2-83 | Cl | H | CF$_3$ | CH$_3$SCH$_2$CO | 1 |
| 2-84 | Cl | H | CF$_3$ | CF$_3$CH$_2$CO | 1 |
| 2-85 | Cl | H | CF$_3$ | EtNHCO | 1 |
| 2-86 | Cl | H | CF$_3$ | tert-BuOC(=O) | 1 |
| 2-87 | F | H | CF$_3$ | H | 1 |
| 2-88 | F | H | CF$_3$ | MeCO | 1 |
| 2-89 | F | H | CF$_3$ | EtCO | 1 |
| 2-90 | F | H | CF$_3$ | cyclo-PrCO | 1 |
| 2-91 | F | H | CF$_3$ | CH$_3$SCH$_2$CO | 1 |
| 2-92 | F | H | CF$_3$ | CF$_3$CH$_2$CO | 1 |
| 2-93 | F | H | CF$_3$ | EtNHCO | 1 |
| 2-94 | F | H | CF$_3$ | tert-BuOC(=O) | 1 |
| 2-95 | H | F | CF$_3$ | H | 1 |
| 2-96 | H | F | CF$_3$ | MeCO | 1 |
| 2-97 | H | F | CF$_3$ | EtCO | 1 |
| 2-98 | H | F | CF$_3$ | cyclo-PrCO | 1 |
| 2-99 | H | F | CF$_3$ | CH$_3$SCH$_2$CO | 1 |
| 2-100 | H | F | CF$_3$ | CF$_3$CH$_2$CO | 1 |
| 2-101 | H | F | CF$_3$ | EtNHCO | 1 |
| 2-102 | H | F | CF$_3$ | tert-BuOC(=O) | 1 |
| 2-103 | Cl | H | Cl | H | 2 |
| 2-104 | Cl | H | Cl | MeCO | 2 |
| 2-105 | Cl | H | Cl | EtCO | 2 |
| 2-106 | Cl | H | Cl | n-PrCO | 2 |
| 2-107 | Cl | H | Cl | cyclo-PrCO | 2 |
| 2-108 | Cl | H | Cl | cyclo-PrCH$_2$CO | 2 |
| 2-109 | Cl | H | Cl | CF$_3$CH$_2$CO | 2 |
| 2-110 | Cl | H | Cl | CH$_3$SCH$_2$CO | 2 |
| 2-111 | Cl | H | Cl | CH$_3$SOCH$_2$CO | 2 |
| 2-112 | Cl | H | Cl | CH$_3$SO$_2$CH$_2$CO | 2 |
| 2-113 | Cl | H | Cl | CH$_3$OCH$_2$CH$_2$CO | 2 |
| 2-114 | Cl | H | Cl | CH$_3$OCH(Me)CH$_2$CO | 2 |
| 2-115 | Cl | H | Cl | EtNHCO | 2 |
| 2-116 | Cl | H | Cl | tert-BuOC(=O) | 2 |
| 2-117 | Br | H | Br | H | 2 |
| 2-118 | Br | H | Br | MeCO | 2 |
| 2-119 | Br | H | Br | EtCO | 2 |
| 2-120 | Br | H | Br | n-PrCO | 2 |
| 2-121 | Br | H | Br | cyclo-PrCO | 2 |
| 2-122 | Br | H | Br | cyclo-PrCH$_2$CO | 2 |
| 2-123 | Br | H | Br | CF$_3$CH$_2$CO | 2 |
| 2-124 | Br | H | Br | CH$_3$SCH$_2$CO | 2 |
| 2-125 | Br | H | Br | CH$_3$SOCH$_2$CO | 2 |
| 2-126 | Br | H | Br | CH$_3$SO$_2$CH$_2$CO | 2 |
| 2-127 | Br | H | Br | CH$_3$OCH$_2$CH$_2$CO | 2 |
| 2-128 | Br | H | Br | CH$_3$OCH(Me)CH$_2$CO | 2 |
| 2-129 | Br | H | Br | EtNHCO | 2 |
| 2-130 | Br | H | Br | tert-BuOC(=O) | 2 |
| 2-131 | Cl | Cl | Cl | H | 2 |
| 2-132 | Cl | Cl | Cl | MeCO | 2 |
| 2-133 | Cl | Cl | Cl | EtCO | 2 |
| 2-134 | Cl | Cl | Cl | n-PrCO | 2 |
| 2-135 | Cl | Cl | Cl | cyclo-PrCO | 2 |
| 2-136 | Cl | Cl | Cl | cyclo-PrCH$_2$CO | 2 |
| 2-137 | Cl | Cl | Cl | CF$_3$CH$_2$CO | 2 |
| 2-138 | Cl | Cl | Cl | CH$_3$SCH$_2$CO | 2 |
| 2-139 | Cl | Cl | Cl | CH$_3$SOCH$_2$CO | 2 |
| 2-140 | Cl | Cl | Cl | CH$_3$SO$_2$CH$_2$CO | 2 |

TABLE 2-continued

| Compound No. | X² | X³ | X⁴ | R⁴ | m |
|---|---|---|---|---|---|
| 2-141 | Cl | Cl | Cl | CH₃OCH₂CH₂CO | 2 |
| 2-142 | Cl | Cl | Cl | CH₃OCH(Me)CH₂CO | 2 |
| 2-143 | Cl | Cl | Cl | EtNHCO | 2 |
| 2-144 | Cl | Cl | Cl | tert-BuOC(=O) | 2 |
| 2-145 | CF₃ | H | H | H | 2 |
| 2-146 | CF₃ | H | H | MeCO | 2 |
| 2-147 | CF₃ | H | H | EtCO | 2 |
| 2-148 | CF₃ | H | H | n-PrCO | 2 |
| 2-149 | CF₃ | H | H | cyclo-PrCO | 2 |
| 2-150 | CF₃ | H | H | cyclo-PrCH₂CO | 2 |
| 2-151 | CF₃ | H | H | CF₃CH₂CO | 2 |
| 2-152 | CF₃ | H | H | CH₃SCH₂CO | 2 |
| 2-153 | CF₃ | H | H | CH₃SOCH₂CO | 2 |
| 2-154 | CF₃ | H | H | CH₃SO₂CH₂CO | 2 |
| 2-155 | CF₃ | H | H | CH₃OCH₂CH₂CO | 2 |
| 2-156 | CF₃ | H | H | CH₃OCH(Me)CH₂CO | 2 |
| 2-157 | CF₃ | H | H | EtNHCO | 2 |
| 2-158 | CF₃ | H | H | tert-BuOC(=O) | 2 |
| 2-159 | CF₃ | H | CF₃ | H | 2 |
| 2-160 | CF₃ | H | CF₃ | MeCO | 2 |
| 2-161 | CF₃ | H | CF₃ | EtCO | 2 |
| 2-162 | CF₃ | H | CF₃ | n-PrCO | 2 |
| 2-163 | CF₃ | H | CF₃ | cyclo-PrCO | 2 |
| 2-164 | CF₃ | H | CF₃ | cyclo-PrCH₂CO | 2 |
| 2-165 | CF₃ | H | CF₃ | CF₃CH₂CO | 2 |
| 2-166 | CF₃ | H | CF₃ | CH₃SCH₂CO | 2 |
| 2-167 | CF₃ | H | CF₃ | CH₃SOCH₂CO | 2 |
| 2-168 | CF₃ | H | CF₃ | CH₃SO₂CH₂CO | 2 |
| 2-169 | CF₃ | H | CF₃ | CH₃OCH₂CH₂CO | 2 |
| 2-170 | CF₃ | H | CF₃ | CH₃OCH(Me)CH₂CO | 2 |
| 2-171 | CF₃ | H | CF₃ | EtNHCO | 2 |
| 2-172 | CF₃ | H | CF₃ | tert-BuOC(=O) | 2 |
| 2-173 | Cl | Cl | CF₃ | H | 2 |
| 2-174 | Cl | Cl | CF₃ | MeCO | 2 |
| 2-175 | Cl | Cl | CF₃ | EtCO | 2 |
| 2-176 | Cl | Cl | CF₃ | cyclo-PrCO | 2 |
| 2-177 | Cl | Cl | CF₃ | CH₃SCH₂CO | 2 |
| 2-178 | Cl | Cl | CF₃ | CF₃CH₂CO | 2 |
| 2-179 | Cl | Cl | CF₃ | EtNHCO | 2 |
| 2-180 | Cl | Cl | CF₃ | tert-BuOC(=O) | 2 |
| 2-181 | Cl | H | CF₃ | H | 2 |
| 2-182 | Cl | H | CF₃ | MeCO | 2 |
| 2-183 | Cl | H | CF₃ | EtCO | 2 |
| 2-184 | Cl | H | CF₃ | cyclo-PrCO | 2 |
| 2-185 | Cl | H | CF₃ | CH₃SCH₂CO | 2 |
| 2-186 | Cl | H | CF₃ | CF₃CH₂CO | 2 |
| 2-187 | Cl | H | CF₃ | EtNHCO | 2 |
| 2-188 | Cl | H | CF₃ | tert-BuOC(=O) | 2 |
| 2-189 | F | H | CF₃ | H | 2 |
| 2-190 | F | H | CF₃ | MeCO | 2 |
| 2-191 | F | H | CF₃ | EtCO | 2 |
| 2-192 | F | H | CF₃ | cyclo-PrCO | 2 |
| 2-193 | F | H | CF₃ | CH₃SCH₂CO | 2 |
| 2-194 | F | H | CF₃ | CF₃CH₂CO | 2 |
| 2-195 | F | H | CF₃ | EtNHCO | 2 |
| 2-196 | F | H | CF₃ | tert-BuOC(=O) | 2 |
| 2-197 | H | F | CF₃ | H | 2 |
| 2-198 | H | F | CF₃ | MeCO | 2 |
| 2-199 | H | F | CF₃ | EtCO | 2 |
| 2-200 | H | F | CF₃ | cyclo-PrCO | 2 |
| 2-201 | H | F | CF₃ | CH₃SCH₂CO | 2 |
| 2-202 | H | F | CF₃ | CF₃CH₂CO | 2 |
| 2-203 | H | F | CF₃ | EtNHCO | 2 |
| 2-204 | H | F | CF₃ | tert-BuOC(=O) | 2 |
| 2-205 | OCF₃ | H | H | EtCO | 1 |
| 2-206 | SCF₃ | H | H | EtCO | 1 |
| 2-207 | SOCF₃ | H | H | EtCO | 1 |
| 2-208 | SO₂CF₃ | H | H | EtCO | 1 |

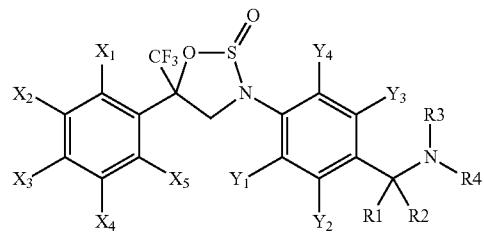

Wherein, X¹, X⁵, Y¹, Y², Y⁴, R² and R³ represent hydrogen.

TABLE 3

| Compound No. | X² | X³ | X⁴ | Y³ | R¹ | R⁴ |
|---|---|---|---|---|---|---|
| 3-1 | Cl | H | Cl | CF₃ | H | H |
| 3-2 | Cl | H | Cl | CF₃ | H | MeCO |
| 3-3 | Cl | H | Cl | CF₃ | H | EtCO |
| 3-4 | Cl | H | Cl | CF₃ | H | n-PrCO |
| 3-5 | Cl | H | Cl | CF₃ | H | cyclo-PrCO |
| 3-6 | Cl | H | Cl | CF₃ | H | cyclo-PrCH₂CO |
| 3-7 | Cl | H | Cl | CF₃ | H | CF₃CH₂CO |
| 3-8 | Cl | H | Cl | CF₃ | H | CH₃SCH₂CO |
| 3-9 | Cl | H | Cl | CF₃ | H | CH₃SOCH₂CO |
| 3-10 | Cl | H | Cl | CF₃ | H | CH₃SO₂CH₂CO |
| 3-11 | Cl | H | Cl | CF₃ | H | CH₃OCH₂CH₂CO |
| 3-12 | Cl | H | Cl | CF₃ | H | CH₃OCH(Me)CH₂CO |
| 3-13 | Cl | H | Cl | CF₃ | H | EtNHCO |
| 3-14 | Cl | H | Cl | CF₃ | H | tert-BuOC(=O) |
| 3-15 | Cl | Cl | Cl | CF₃ | H | H |
| 3-16 | Cl | Cl | Cl | CF₃ | H | MeCO |
| 3-17 | Cl | Cl | Cl | CF₃ | H | EtCO |
| 3-18 | Cl | Cl | Cl | CF₃ | H | n-PrCO |
| 3-19 | Cl | Cl | Cl | CF₃ | H | cyclo-PrCO |
| 3-20 | Cl | Cl | Cl | CF₃ | H | cyclo-PrCH₂CO |
| 3-21 | Cl | Cl | Cl | CF₃ | H | CF₃CH₂CO |
| 3-22 | Cl | Cl | Cl | CF₃ | H | CH₃SCH₂CO |
| 3-23 | Cl | Cl | Cl | CF₃ | H | CH₃SOCH₂CO |
| 3-24 | Cl | Cl | Cl | CF₃ | H | CH₃SO₂CH₂CO |
| 3-25 | Cl | Cl | Cl | CF₃ | H | CH₃OCH₂CH₂CO |
| 3-26 | Cl | Cl | Cl | CF₃ | H | CH₃OCH(Me)CH₂CO |
| 3-27 | Cl | Cl | Cl | CF₃ | H | EtNHCO |
| 3-28 | Cl | Cl | Cl | CF₃ | H | tert-BuOC(=O) |
| 3-29 | Cl | Cl | Cl | Cl | H | H |
| 3-30 | Cl | Cl | Cl | Cl | H | MeCO |
| 3-31 | Cl | Cl | Cl | Cl | H | EtCO |
| 3-32 | Cl | Cl | Cl | Cl | H | n-PrCO |
| 3-33 | Cl | Cl | Cl | Cl | H | cyclo-PrCO |
| 3-34 | Cl | Cl | Cl | Cl | H | cyclo-PrCH₂CO |
| 3-35 | Cl | Cl | Cl | Cl | H | CF₃CH₂CO |
| 3-36 | Cl | Cl | Cl | Cl | H | CH₃SCH₂CO |
| 3-37 | Cl | Cl | Cl | Cl | H | CH₃SOCH₂CO |
| 3-38 | Cl | Cl | Cl | Cl | H | CH₃SO₂CH₂CO |
| 3-39 | Cl | Cl | Cl | Cl | H | CH₃OCH₂CH₂CO |
| 3-40 | Cl | Cl | Cl | Cl | H | CH₃OCH(Me)CH₂CO |
| 3-41 | Cl | Cl | Cl | Cl | H | EtNHCO |
| 3-42 | Cl | Cl | Cl | Cl | H | tert-BuOC(=O) |
| 3-43 | Cl | Cl | Cl | Me | H | H |
| 3-44 | Cl | Cl | Cl | Me | H | MeCO |
| 3-45 | Cl | Cl | Cl | Me | H | EtCO |
| 3-46 | Cl | Cl | Cl | Me | H | n-PrCO |
| 3-47 | Cl | Cl | Cl | Me | H | cyclo-PrCO |
| 3-48 | Cl | Cl | Cl | Me | H | cyclo-PrCH₂CO |
| 3-49 | Cl | Cl | Cl | Me | H | CF₃CH₂CO |
| 3-50 | Cl | Cl | Cl | Me | H | CH₃SCH₂CO |
| 3-51 | Cl | Cl | Cl | Me | H | CH₃SOCH₂CO |
| 3-52 | Cl | Cl | Cl | Me | H | CH₃SO₂CH₂CO |
| 3-53 | Cl | Cl | Cl | Me | H | CH₃OCH₂CH₂CO |
| 3-54 | Cl | Cl | Cl | Me | H | CH₃OCH(Me)CH₂CO |
| 3-55 | Cl | Cl | Cl | Me | H | EtNHCO |
| 3-56 | Cl | Cl | Cl | Me | H | tert-BuOC(=O) |
| 3-57 | Cl | Cl | Cl | H | H | H |
| 3-58 | Cl | Cl | Cl | H | H | MeCO |
| 3-59 | Cl | Cl | Cl | H | H | EtCO |
| 3-60 | Cl | Cl | Cl | H | H | n-PrCO |
| 3-61 | Cl | Cl | Cl | H | H | cyclo-PrCO |

TABLE 3-continued

| Compound No. | $X^2$ | $X^3$ | $X^4$ | $Y^3$ | $R^1$ | $R^4$ |
|---|---|---|---|---|---|---|
| 3-62 | Cl | Cl | Cl | H | H | cyclo-PrCH$_2$CO |
| 3-63 | Cl | Cl | Cl | H | H | CF$_3$CH$_2$CO |
| 3-64 | Cl | Cl | Cl | H | H | CH$_3$SCH$_2$CO |
| 3-65 | Cl | Cl | Cl | H | H | CH$_3$SOCH$_2$CO |
| 3-66 | Cl | Cl | Cl | H | H | CH$_3$SO$_2$CH$_2$CO |
| 3-67 | Cl | Cl | Cl | H | H | CH$_3$OCH$_2$CH$_2$CO |
| 3-68 | Cl | Cl | Cl | H | H | CH$_3$OCH(Me)CH$_2$CO |
| 3-69 | Cl | Cl | Cl | H | H | EtNHCO |
| 3-70 | Cl | Cl | Cl | H | H | tert-BuOC(=O) |
| 3-71 | CF$_3$ | H | H | CF$_3$ | H | H |
| 3-72 | CF$_3$ | H | H | CF$_3$ | H | MeCO |
| 3-73 | CF$_3$ | H | H | CF$_3$ | H | EtCO |
| 3-74 | CF$_3$ | H | H | CF$_3$ | H | n-PrCO |
| 3-75 | CF$_3$ | H | H | CF$_3$ | H | cyclo-PrCO |
| 3-76 | CF$_3$ | H | H | CF$_3$ | H | cyclo-PrCH$_2$CO |
| 3-77 | CF$_3$ | H | H | CF$_3$ | H | CF$_3$CH$_2$CO |
| 3-78 | CF$_3$ | H | H | CF$_3$ | H | CH$_3$SCH$_2$CO |
| 3-79 | CF$_3$ | H | H | CF$_3$ | H | CH$_3$SOCH$_2$CO |
| 3-80 | CF$_3$ | H | H | CF$_3$ | H | CH$_3$SO$_2$CH$_2$CO |
| 3-81 | CF$_3$ | H | H | CF$_3$ | H | CH$_3$OCH$_2$CH$_2$CO |
| 3-82 | CF$_3$ | H | H | CF$_3$ | H | CH$_3$OCH(Me)CH$_2$CO |
| 3-83 | CF$_3$ | H | H | CF$_3$ | H | EtNHCO |
| 3-84 | CF$_3$ | H | H | CF$_3$ | H | tert-BuOC(=O) |
| 3-85 | CF$_3$ | H | H | Cl | H | H |
| 3-86 | CF$_3$ | H | H | Cl | H | MeCO |
| 3-87 | CF$_3$ | H | H | Cl | H | EtCO |
| 3-88 | CF$_3$ | H | H | Cl | H | n-PrCO |
| 3-89 | CF$_3$ | H | H | Cl | H | cyclo-PrCO |
| 3-90 | CF$_3$ | H | H | Cl | H | cyclo-PrCH$_2$CO |
| 3-91 | CF$_3$ | H | H | Cl | H | CF$_3$CH$_2$CO |
| 3-92 | CF$_3$ | H | H | Cl | H | CH$_3$SCH$_2$CO |
| 3-93 | CF$_3$ | H | H | Cl | H | CH$_3$SOCH$_2$CO |
| 3-94 | CF$_3$ | H | H | Cl | H | CH$_3$SO$_2$CH$_2$CO |
| 3-95 | CF$_3$ | H | H | Cl | H | CH$_3$OCH$_2$CH$_2$CO |
| 3-96 | CF$_3$ | H | H | Cl | H | CH$_3$OCH(Me)CH$_2$CO |
| 3-97 | CF$_3$ | H | H | Cl | H | EtNHCO |
| 3-98 | CF$_3$ | H | H | Cl | H | tert-BuOC(=O) |
| 3-99 | CF$_3$ | H | H | Me | H | H |
| 3-100 | CF$_3$ | H | H | Me | H | MeCO |
| 3-101 | CF$_3$ | H | H | Me | H | EtCO |
| 3-102 | CF$_3$ | H | H | Me | H | n-PrCO |
| 3-103 | CF$_3$ | H | H | Me | H | cyclo-PrCO |
| 3-104 | CF$_3$ | H | H | Me | H | cyclo-PrCH$_2$CO |
| 3-105 | CF$_3$ | H | H | Me | H | CF$_3$CH$_2$CO |
| 3-106 | CF$_3$ | H | H | Me | H | CH$_3$SCH$_2$CO |
| 3-107 | CF$_3$ | H | H | Me | H | CH$_3$SOCH$_2$CO |
| 3-108 | CF$_3$ | H | H | Me | H | CH$_3$SO$_2$CH$_2$CO |
| 3-109 | CF$_3$ | H | H | Me | H | CH$_3$OCH$_2$CH$_2$CO |
| 3-110 | CF$_3$ | H | H | Me | H | CH$_3$OCH(Me)CH$_2$CO |
| 3-111 | CF$_3$ | H | H | Me | H | EtNHCO |
| 3-112 | CF$_3$ | H | H | Me | H | tert-BuOC(=O) |
| 3-113 | CF$_3$ | H | H | H | H | H |
| 3-114 | CF$_3$ | H | H | H | H | MeCO |
| 3-115 | CF$_3$ | H | H | H | H | EtCO |
| 3-116 | CF$_3$ | H | H | H | H | n-PrCO |
| 3-117 | CF$_3$ | H | H | H | H | cyclo-PrCO |
| 3-118 | CF$_3$ | H | H | H | H | cyclo-PrCH$_2$CO |
| 3-119 | CF$_3$ | H | H | H | H | CF$_3$CH$_2$CO |
| 3-120 | CF$_3$ | H | H | H | H | CH$_3$SCH$_2$CO |
| 3-121 | CF$_3$ | H | H | H | H | CH$_3$SOCH$_2$CO |
| 3-122 | CF$_3$ | H | H | H | H | CH$_3$SO$_2$CH$_2$CO |
| 3-123 | CF$_3$ | H | H | H | H | CH$_3$OCH$_2$CH$_2$CO |
| 3-124 | CF$_3$ | H | H | H | H | CH$_3$OCH(Me)CH$_2$CO |
| 3-125 | CF$_3$ | H | H | H | H | EtNHCO |
| 3-126 | CF$_3$ | H | H | H | H | tert-BuOC(=O) |
| 3-127 | CF$_3$ | H | CF$_3$ | CF$_3$ | H | H |
| 3-128 | CF$_3$ | H | CF$_3$ | CF$_3$ | H | MeCO |
| 3-129 | CF$_3$ | H | CF$_3$ | CF$_3$ | H | EtCO |
| 3-130 | CF$_3$ | H | CF$_3$ | CF$_3$ | H | n-PrCO |
| 3-131 | CF$_3$ | H | CF$_3$ | CF$_3$ | H | cyclo-PrCO |
| 3-132 | CF$_3$ | H | CF$_3$ | CF$_3$ | H | cyclo-PrCH$_2$CO |
| 3-133 | CF$_3$ | H | CF$_3$ | CF$_3$ | H | CF$_3$CH$_2$CO |
| 3-134 | CF$_3$ | H | CF$_3$ | CF$_3$ | H | CH$_3$SCH$_2$CO |
| 3-135 | CF$_3$ | H | CF$_3$ | CF$_3$ | H | CH$_3$SOCH$_2$CO |
| 3-136 | CF$_3$ | H | CF$_3$ | CF$_3$ | H | CH$_3$SO$_2$CH$_2$CO |
| 3-137 | CF$_3$ | H | CF$_3$ | CF$_3$ | H | CH$_3$OCH$_2$CH$_2$CO |
| 3-138 | CF$_3$ | H | CF$_3$ | CF$_3$ | H | CH$_3$OCH(Me)CH$_2$CO |
| 3-139 | CF$_3$ | H | CF$_3$ | CF$_3$ | H | EtNHCO |
| 3-140 | CF$_3$ | H | CF$_3$ | CF$_3$ | H | tert-BuOC(=O) |
| 3-141 | CF$_3$ | H | CF$_3$ | Cl | H | H |
| 3-142 | CF$_3$ | H | CF$_3$ | Cl | H | MeCO |
| 3-143 | CF$_3$ | H | CF$_3$ | Cl | H | EtCO |
| 3-144 | CF$_3$ | H | CF$_3$ | Cl | H | n-PrCO |
| 3-145 | CF$_3$ | H | CF$_3$ | Cl | H | cyclo-PrCO |
| 3-146 | CF$_3$ | H | CF$_3$ | Cl | H | cyclo-PrCH$_2$CO |
| 3-147 | CF$_3$ | H | CF$_3$ | Cl | H | CF$_3$CH$_2$CO |
| 3-148 | CF$_3$ | H | CF$_3$ | Cl | H | CH$_3$SCH$_2$CO |
| 3-149 | CF$_3$ | H | CF$_3$ | Cl | H | CH$_3$SOCH$_2$CO |
| 3-150 | CF$_3$ | H | CF$_3$ | Cl | H | CH$_3$SO$_2$CH$_2$CO |
| 3-151 | CF$_3$ | H | CF$_3$ | Cl | H | CH$_3$OCH$_2$CH$_2$CO |
| 3-152 | CF$_3$ | H | CF$_3$ | Cl | H | CH$_3$OCH(Me)CH$_2$CO |
| 3-153 | CF$_3$ | H | CF$_3$ | Cl | H | EtNHCO |
| 3-154 | CF$_3$ | H | CF$_3$ | Cl | H | tert-BuOC(=O) |
| 3-155 | CF$_3$ | H | CF$_3$ | Me | H | H |
| 3-156 | CF$_3$ | H | CF$_3$ | Me | H | MeCO |
| 3-157 | CF$_3$ | H | CF$_3$ | Me | H | EtCO |
| 3-158 | CF$_3$ | H | CF$_3$ | Me | H | n-PrCO |
| 3-159 | CF$_3$ | H | CF$_3$ | Me | H | cyclo-PrCO |
| 3-160 | CF$_3$ | H | CF$_3$ | Me | H | cyclo-PrCH$_2$CO |
| 3-161 | CF$_3$ | H | CF$_3$ | Me | H | CF$_3$CH$_2$CO |
| 3-162 | CF$_3$ | H | CF$_3$ | Me | H | CH$_3$SCH$_2$CO |
| 3-163 | CF$_3$ | H | CF$_3$ | Me | H | CH$_3$SOCH$_2$CO |
| 3-164 | CF$_3$ | H | CF$_3$ | Me | H | CH$_3$SO$_2$CH$_2$CO |
| 3-165 | CF$_3$ | H | CF$_3$ | Me | H | CH$_3$OCH$_2$CH$_2$CO |
| 3-166 | CF$_3$ | H | CF$_3$ | Me | H | CH$_3$OCH(Me)CH$_2$CO |
| 3-167 | CF$_3$ | H | CF$_3$ | Me | H | EtNHCO |
| 3-168 | CF$_3$ | H | CF$_3$ | Me | H | tert-BuOC(=O) |
| 3-169 | CF$_3$ | H | CF$_3$ | H | H | H |
| 3-170 | CF$_3$ | H | CF$_3$ | H | H | MeCO |
| 3-171 | CF$_3$ | H | CF$_3$ | H | H | EtCO |
| 3-172 | CF$_3$ | H | CF$_3$ | H | H | n-PrCO |
| 3-173 | CF$_3$ | H | CF$_3$ | H | H | cyclo-PrCO |
| 3-174 | CF$_3$ | H | CF$_3$ | H | H | cyclo-PrCH$_2$CO |
| 3-175 | CF$_3$ | H | CF$_3$ | H | H | CF$_3$CH$_2$CO |
| 3-176 | CF$_3$ | H | CF$_3$ | H | H | CH$_3$SCH$_2$CO |
| 3-177 | CF$_3$ | H | CF$_3$ | H | H | CH$_3$SOCH$_2$CO |
| 3-178 | CF$_3$ | H | CF$_3$ | H | H | CH$_3$SO$_2$CH$_2$CO |
| 3-179 | CF$_3$ | H | CF$_3$ | H | H | CH$_3$OCH$_2$CH$_2$CO |
| 3-180 | CF$_3$ | H | CF$_3$ | H | H | CH$_3$OCH(Me)CH$_2$CO |
| 3-181 | CF$_3$ | H | CF$_3$ | H | H | EtNHCO |
| 3-182 | CF$_3$ | H | CF$_3$ | H | H | tert-BuOC(=O) |
| 3-183 | Cl | Cl | CF$_3$ | CF$_3$ | H | H |
| 3-184 | Cl | Cl | CF$_3$ | CF$_3$ | H | MeCO |
| 3-185 | Cl | Cl | CF$_3$ | CF$_3$ | H | EtCO |
| 3-186 | Cl | Cl | CF$_3$ | CF$_3$ | H | cyclo-PrCO |
| 3-187 | Cl | Cl | CF$_3$ | CF$_3$ | H | CH$_3$SCH$_2$CO |
| 3-188 | Cl | Cl | CF$_3$ | CF$_3$ | H | CF$_3$CH$_2$CO |
| 3-189 | Cl | Cl | CF$_3$ | CF$_3$ | H | EtNHCO |
| 3-190 | Cl | Cl | CF$_3$ | CF$_3$ | H | tert-BuOC(=O) |
| 3-191 | Cl | H | CF$_3$ | CF$_3$ | H | H |
| 3-192 | Cl | H | CF$_3$ | CF$_3$ | H | MeCO |
| 3-193 | Cl | H | CF$_3$ | CF$_3$ | H | EtCO |
| 3-194 | Cl | H | CF$_3$ | CF$_3$ | H | cyclo-PrCO |
| 3-195 | Cl | H | CF$_3$ | CF$_3$ | H | CH$_3$SCH$_2$CO |
| 3-196 | Cl | H | CF$_3$ | CF$_3$ | H | CF$_3$CH$_2$CO |
| 3-197 | Cl | H | CF$_3$ | CF$_3$ | H | EtNHCO |
| 3-198 | Cl | H | CF$_3$ | CF$_3$ | H | tert-BuOC(=O) |
| 3-199 | F | H | CF$_3$ | CF$_3$ | H | H |
| 3-200 | F | H | CF$_3$ | CF$_3$ | H | MeCO |
| 3-201 | F | H | CF$_3$ | CF$_3$ | H | EtCO |
| 3-202 | F | H | CF$_3$ | CF$_3$ | H | cyclo-PrCO |
| 3-203 | F | H | CF$_3$ | CF$_3$ | H | CH$_3$SCH$_2$CO |
| 3-204 | F | H | CF$_3$ | CF$_3$ | H | CF$_3$CH$_2$CO |
| 3-205 | F | H | CF$_3$ | CF$_3$ | H | EtNHCO |
| 3-206 | F | H | CF$_3$ | CF$_3$ | H | tert-BuOC(=O) |
| 3-207 | H | F | CF$_3$ | CF$_3$ | H | H |
| 3-208 | H | F | CF$_3$ | CF$_3$ | H | MeCO |
| 3-209 | H | F | CF$_3$ | CF$_3$ | H | EtCO |
| 3-210 | H | F | CF$_3$ | CF$_3$ | H | cyclo-PrCO |
| 3-211 | H | F | CF$_3$ | CF$_3$ | H | CH$_3$SCH$_2$CO |
| 3-212 | H | F | CF$_3$ | CF$_3$ | H | CF$_3$CH$_2$CO |
| 3-213 | H | F | CF$_3$ | CF$_3$ | H | EtNHCO |
| 3-214 | H | F | CF$_3$ | CF$_3$ | H | tert-BuOC(=O) |
| 3-215 | Cl | H | Cl | Br | H | H |
| 3-216 | Cl | H | Cl | Br | H | MeCO |
| 3-217 | Cl | H | Cl | Br | H | EtCO |

TABLE 3-continued

| Compound No. | X² | X³ | X⁴ | Y³ | R¹ | R⁴ |
|---|---|---|---|---|---|---|
| 3-218 | Cl | H | Cl | Br | H | n-PrCO |
| 3-219 | Cl | H | Cl | Br | H | cyclo-PrCO |
| 3-220 | Cl | H | Cl | Br | H | cyclo-PrCH₂CO |
| 3-221 | Cl | H | Cl | Br | H | CF₃CH₂CO |
| 3-222 | Cl | H | Cl | Br | H | CH₃SCH₂CO |
| 3-223 | Cl | H | Cl | Br | H | CH₃SOCH₂CO |
| 3-224 | Cl | H | Cl | Br | H | CH₃SO₂CH₂CO |
| 3-225 | Cl | H | Cl | Br | H | CH₃OCH₂CH₂CO |
| 3-226 | Cl | H | Cl | Br | H | CH₃OCH(Me)CH₂CO |
| 3-227 | Cl | H | Cl | Br | H | EtNHCO |
| 3-228 | Cl | H | Cl | Br | H | tert-BuOC(=O) |
| 3-229 | Cl | Cl | Cl | Br | H | H |
| 3-230 | Cl | Cl | Cl | Br | H | MeCO |
| 3-231 | Cl | Cl | Cl | Br | H | EtCO |
| 3-232 | Cl | Cl | Cl | Br | H | n-PrCO |
| 3-233 | Cl | Cl | Cl | Br | H | cyclo-PrCO |
| 3-234 | Cl | Cl | Cl | Br | H | cyclo-PrCH₂CO |
| 3-235 | Cl | Cl | Cl | Br | H | CF₃CH₂CO |
| 3-236 | Cl | Cl | Cl | Br | H | CH₃SCH₂CO |
| 3-237 | Cl | Cl | Cl | Br | H | CH₃SOCH₂CO |
| 3-238 | Cl | Cl | Cl | Br | H | CH₃SO₂CH₂CO |
| 3-239 | Cl | Cl | Cl | Br | H | CH₃OCH₂CH₂CO |
| 3-240 | Cl | Cl | Cl | Br | H | CH₃OCH(Me)CH₂CO |
| 3-241 | Cl | Cl | Cl | Br | H | EtNHCO |
| 3-242 | Cl | Cl | Cl | Br | H | tert-BuOC(=O) |
| 3-243 | CF₃ | H | H | Br | H | H |
| 3-244 | CF₃ | H | H | Br | H | MeCO |
| 3-245 | CF₃ | H | H | Br | H | EtCO |
| 3-246 | CF₃ | H | H | Br | H | n-PrCO |
| 3-247 | CF₃ | H | H | Br | H | cyclo-PrCO |
| 3-248 | CF₃ | H | H | Br | H | cyclo-PrCH₂CO |
| 3-249 | CF₃ | H | H | Br | H | CF₃CH₂CO |
| 3-250 | CF₃ | H | H | Br | H | CH₃SCH₂CO |
| 3-251 | CF₃ | H | H | Br | H | CH₃SOCH₂CO |
| 3-252 | CF₃ | H | H | Br | H | CH₃SO₂CH₂CO |
| 3-253 | CF₃ | H | H | Br | H | CH₃OCH₂CH₂CO |
| 3-254 | CF₃ | H | H | Br | H | CH₃OCH(Me)CH₂CO |
| 3-255 | CF₃ | H | H | Br | H | EtNHCO |
| 3-256 | CF₃ | H | H | Br | H | tert-BuOC(=O) |
| 3-257 | CF₃ | H | CF₃ | Br | H | H |
| 3-258 | CF₃ | H | CF₃ | Br | H | MeCO |
| 3-259 | CF₃ | H | CF₃ | Br | H | EtCO |
| 3-260 | CF₃ | H | CF₃ | Br | H | n-PrCO |
| 3-261 | CF₃ | H | CF₃ | Br | H | cyclo-PrCO |
| 3-262 | CF₃ | H | CF₃ | Br | H | cyclo-PrCH₂CO |
| 3-263 | CF₃ | H | CF₃ | Br | H | CF₃CH₂CO |
| 3-264 | CF₃ | H | CF₃ | Br | H | CH₃SCH₂CO |
| 3-265 | CF₃ | H | CF₃ | Br | H | CH₃SOCH₂CO |
| 3-266 | CF₃ | H | CF₃ | Br | H | CH₃SO₂CH₂CO |
| 3-267 | CF₃ | H | CF₃ | Br | H | CH₃OCH₂CH₂CO |
| 3-268 | CF₃ | H | CF₃ | Br | H | CH₃OCH(Me)CH₂CO |
| 3-269 | CF₃ | H | CF₃ | Br | H | EtNHCO |
| 3-270 | CF₃ | H | CF₃ | Br | H | tert-BuOC(=O) |
| 3-271 | Br | H | Br | CF₃ | H | H |
| 3-272 | Br | H | Br | CF₃ | H | MeCO |
| 3-273 | Br | H | Br | CF₃ | H | EtCO |
| 3-274 | Br | H | Br | CF₃ | H | n-PrCO |
| 3-275 | Br | H | Br | CF₃ | H | cyclo-PrCO |
| 3-276 | Br | H | Br | CF₃ | H | cyclo-PrCH₂CO |
| 3-277 | Br | H | Br | CF₃ | H | CF₃CH₂CO |
| 3-278 | Br | H | Br | CF₃ | H | CH₃SCH₂CO |
| 3-279 | Br | H | Br | CF₃ | H | CH₃SOCH₂CO |
| 3-280 | Br | H | Br | CF₃ | H | CH₃SO₂CH₂CO |
| 3-281 | Br | H | Br | CF₃ | H | CH₃OCH₂CH₂CO |
| 3-282 | Br | H | Br | CF₃ | H | CH₃OCH(Me)CH₂CO |
| 3-283 | Br | H | Br | CF₃ | H | EtNHCO |
| 3-284 | Br | H | Br | CF₃ | H | tert-BuOC(=O) |
| 3-285 | Br | H | Br | Cl | H | H |
| 3-286 | Br | H | Br | Cl | H | MeCO |
| 3-287 | Br | H | Br | Cl | H | EtCO |
| 3-288 | Br | H | Br | Cl | H | n-PrCO |
| 3-289 | Br | H | Br | Cl | H | cyclo-PrCO |
| 3-290 | Br | H | Br | Cl | H | cyclo-PrCH₂CO |
| 3-291 | Br | H | Br | Cl | H | CF₃CH₂CO |
| 3-292 | Br | H | Br | Cl | H | CH₃SCH₂CO |
| 3-293 | Br | H | Br | Cl | H | CH₃SOCH₂CO |
| 3-294 | Br | H | Br | Cl | H | CH₃SO₂CH₂CO |
| 3-295 | Br | H | Br | Cl | H | CH₃OCH₂CH₂CO |
| 3-296 | Br | H | Br | Cl | H | CH₃OCH(Me)CH₂CO |
| 3-297 | Br | H | Br | Cl | H | EtNHCO |
| 3-298 | Br | H | Br | Cl | H | tert-BuOC(=O) |
| 3-299 | Br | H | Br | Br | H | H |
| 3-300 | Br | H | Br | Br | H | MeCO |
| 3-301 | Br | H | Br | Br | H | EtCO |
| 3-302 | Br | H | Br | Br | H | n-PrCO |
| 3-303 | Br | H | Br | Br | H | cyclo-PrCO |
| 3-304 | Br | H | Br | Br | H | cyclo-PrCH₂CO |
| 3-305 | Br | H | Br | Br | H | CF₃CH₂CO |
| 3-306 | Br | H | Br | Br | H | CH₃SCH₂CO |
| 3-307 | Br | H | Br | Br | H | CH₃SOCH₂CO |
| 3-308 | Br | H | Br | Br | H | CH₃SO₂CH₂CO |
| 3-309 | Br | H | Br | Br | H | CH₃OCH₂CH₂CO |
| 3-310 | Br | H | Br | Br | H | CH₃OCH(Me)CH₂CO |
| 3-311 | Br | H | Br | Br | H | EtNHCO |
| 3-312 | Br | H | Br | Br | H | tert-BuOC(=O) |
| 3-313 | Br | H | Br | Me | H | H |
| 3-314 | Br | H | Br | Me | H | MeCO |
| 3-315 | Br | H | Br | Me | H | EtCO |
| 3-316 | Br | H | Br | Me | H | n-PrCO |
| 3-317 | Br | H | Br | Me | H | cyclo-PrCO |
| 3-318 | Br | H | Br | Me | H | cyclo-PrCH₂CO |
| 3-319 | Br | H | Br | Me | H | CF₃CH₂CO |
| 3-320 | Br | H | Br | Me | H | CH₃SCH₂CO |
| 3-321 | Br | H | Br | Me | H | CH₃SOCH₂CO |
| 3-322 | Br | H | Br | Me | H | CH₃SO₂CH₂CO |
| 3-323 | Br | H | Br | Me | H | CH₃OCH₂CH₂CO |
| 3-324 | Br | H | Br | Me | H | CH₃OCH(Me)CH₂CO |
| 3-325 | Br | H | Br | Me | H | EtNHCO |
| 3-326 | Br | H | Br | Me | H | tert-BuOC(=O) |
| 3-327 | Br | H | Br | H | H | H |
| 3-328 | Br | H | Br | H | H | MeCO |
| 3-329 | Br | H | Br | H | H | EtCO |
| 3-330 | Br | H | Br | H | H | n-PrCO |
| 3-331 | Br | H | Br | H | H | cyclo-PrCO |
| 3-332 | Br | H | Br | H | H | cyclo-PrCH₂CO |
| 3-333 | Br | H | Br | H | H | CF₃CH₂CO |
| 3-334 | Br | H | Br | H | H | CH₃SCH₂CO |
| 3-335 | Br | H | Br | H | H | CH₃SOCH₂CO |
| 3-336 | Br | H | Br | H | H | CH₃SO₂CH₂CO |
| 3-337 | Br | H | Br | H | H | CH₃OCH₂CH₂CO |
| 3-338 | Br | H | Br | H | H | CH₃OCH(Me)CH₂CO |
| 3-339 | Br | H | Br | H | H | EtNHCO |
| 3-340 | Br | H | Br | H | H | tert-BuOC(=O) |
| 3-341 | Cl | H | Cl | H | Me | H |
| 3-342 | Cl | H | Cl | H | Me | MeCO |
| 3-343 | Cl | H | Cl | H | Me | EtCO |
| 3-344 | Cl | H | Cl | H | Me | n-PrCO |
| 3-345 | Cl | H | Cl | H | Me | cyclo-PrCO |
| 3-345-a | Cl | H | Cl | H | Me | cyclo-PrCO |
| 3-346 | Cl | H | Cl | H | Me | cyclo-PrCH₂CO |
| 3-347 | Cl | H | Cl | H | Me | CF₃CH₂CO |
| 3-348 | Cl | H | Cl | H | Me | CH₃SCH₂CO |
| 3-349 | Cl | H | Cl | H | Me | CH₃SOCH₂CO |
| 3-350 | Cl | H | Cl | H | Me | CH₃SO₂CH₂CO |
| 3-351 | Cl | H | Cl | H | Me | CH₃OCH₂CH₂CO |
| 3-352 | Cl | H | Cl | H | Me | CH₃OCH(Me)CH₂CO |
| 3-353 | Cl | H | Cl | H | Me | EtNHCO |
| 3-354 | Cl | H | Cl | H | Me | tert-BuOC(=O) |
| 3-355 | Br | H | Br | H | Me | H |
| 3-356 | Br | H | Br | H | Me | MeCO |
| 3-357 | Br | H | Br | H | Me | EtCO |
| 3-358 | Br | H | Br | H | Me | n-PrCO |
| 3-359 | Br | H | Br | H | Me | cyclo-PrCO |
| 3-360 | Br | H | Br | H | Me | cyclo-PrCH₂CO |
| 3-361 | Br | H | Br | H | Me | CF₃CH₂CO |
| 3-362 | Br | H | Br | H | Me | CH₃SCH₂CO |
| 3-363 | Br | H | Br | H | Me | CH₃SOCH₂CO |
| 3-364 | Br | H | Br | H | Me | CH₃SO₂CH₂CO |
| 3-365 | Br | H | Br | H | Me | CH₃OCH₂CH₂CO |
| 3-366 | Br | H | Br | H | Me | CH₃OCH(Me)CH₂CO |
| 3-367 | Br | H | Br | H | Me | EtNHCO |
| 3-368 | Br | H | Br | H | Me | tert-BuOC(=O) |
| 3-369 | Cl | Cl | Cl | H | Me | H |
| 3-370 | Cl | Cl | Cl | H | Me | MeCO |
| 3-370-a | Cl | Cl | Cl | H | Me | MeCO |
| 3-371 | Cl | Cl | Cl | H | Me | EtCO |

TABLE 3-continued

| Compound No. | X² | X³ | X⁴ | Y³ | R¹ | R⁴ |
|---|---|---|---|---|---|---|
| 3-371-a | Cl | Cl | Cl | H | Me | EtCO |
| 3-371-b | Cl | Cl | Cl | H | Me | EtCO |
| 3-372 | Cl | Cl | Cl | H | Me | n-PrCO |
| 3-373 | Cl | Cl | Cl | H | Me | cyclo-PrCO |
| 3-373-a | Cl | Cl | Cl | H | Me | cyclo-PrCO |
| 3-374 | Cl | Cl | Cl | H | Me | cyclo-PrCH₂CO |
| 3-374-a | Cl | Cl | Cl | H | Me | cyclo-PrCH₂CO |
| 3-375 | Cl | Cl | Cl | H | Me | CF₃CH₂CO |
| 3-375-a | Cl | Cl | Cl | H | Me | CF₃CH₂CO |
| 3-376 | Cl | Cl | Cl | H | Me | CH₃SCH₂CO |
| 3-377 | Cl | Cl | Cl | H | Me | CH₃SOCH₂CO |
| 3-378 | Cl | Cl | Cl | H | Me | CH₃SO₂CH₂CO |
| 3-379 | Cl | Cl | Cl | H | Me | CH₃OCH₂CH₂CO |
| 3-379-a | Cl | Cl | Cl | H | Me | CH₃OCH₂CH₂CO |
| 3-380 | Cl | Cl | Cl | H | Me | CH₃OCH(Me)CH₂CO |
| 3-381 | Cl | Cl | Cl | H | Me | EtNHCO |
| 3-382 | Cl | Cl | Cl | H | Me | tert-BuOC(=O) |
| 3-383 | CF₃ | H | H | H | Me | H |
| 3-384 | CF₃ | H | H | H | Me | MeCO |
| 3-385 | CF₃ | H | H | H | Me | EtCO |
| 3-386 | CF₃ | H | H | H | Me | n-PrCO |
| 3-387 | CF₃ | H | H | H | Me | cyclo-PrCO |
| 3-388 | CF₃ | H | H | H | Me | cyclo-PrCH₂CO |
| 3-389 | CF₃ | H | H | H | Me | CF₃CH₂CO |
| 3-390 | CF₃ | H | H | H | Me | CH₃SCH₂CO |
| 3-391 | CF₃ | H | H | H | Me | CH₃SOCH₂CO |
| 3-392 | CF₃ | H | H | H | Me | CH₃SO₂CH₂CO |
| 3-393 | CF₃ | H | H | H | Me | CH₃OCH₂CH₂CO |
| 3-394 | CF₃ | H | H | H | Me | CH₃OCH(Me)CH₂CO |
| 3-395 | CF₃ | H | H | H | Me | EtNHCO |
| 3-396 | CF₃ | H | H | H | Me | tert-BuOC(=O) |
| 3-397 | CF₃ | H | CF₃ | H | Me | H |
| 3-398 | CF₃ | H | CF₃ | H | Me | MeCO |
| 3-398-a | CF₃ | H | CF₃ | H | Me | MeCO |
| 3-399 | CF₃ | H | CF₃ | H | Me | EtCO |
| 3-399-a | CF₃ | H | CF₃ | H | Me | EtCO |
| 3-399-b | CF₃ | H | CF₃ | H | Me | EtCO |
| 3-400 | CF₃ | H | CF₃ | H | Me | n-PrCO |
| 3-401 | CF₃ | H | CF₃ | H | Me | cyclo-PrCO |
| 3-401-a | CF₃ | H | CF₃ | H | Me | cyclo-PrCO |
| 3-402 | CF₃ | H | CF₃ | H | Me | cyclo-PrCH₂CO |
| 3-402-a | CF₃ | H | CF₃ | H | Me | cyclo-PrCH₂CO |
| 3-403 | CF₃ | H | CF₃ | H | Me | CF₃CH₂CO |
| 3-403-a | CF₃ | H | CF₃ | H | Me | CF₃CH₂CO |
| 3-404 | CF₃ | H | CF₃ | H | Me | CH₃SCH₂CO |
| 3-405 | CF₃ | H | CF₃ | H | Me | CH₃SOCH₂CO |
| 3-406 | CF₃ | H | CF₃ | H | Me | CH₃SO₂CH₂CO |
| 3-407 | CF₃ | H | CF₃ | H | Me | CH₃OCH₂CH₂CO |
| 3-407-a | CF₃ | H | CF₃ | H | Me | CH₃OCH₂CH₂CO |
| 3-408 | CF₃ | H | CF₃ | H | Me | CH₃OCH(Me)CH₂CO |
| 3-409 | CF₃ | H | CF₃ | H | Me | EtNHCO |
| 3-410 | CF₃ | H | CF₃ | H | Me | tert-BuOC(=O) |
| 3-411 | Cl | Cl | CF₃ | H | Me | H |
| 3-412 | Cl | Cl | CF₃ | H | Me | MeCO |
| 3-413 | Cl | Cl | CF₃ | H | Me | EtCO |
| 3-414 | Cl | Cl | CF₃ | H | Me | cyclo-PrCO |
| 3-415 | Cl | Cl | CF₃ | H | Me | CH₃SCH₂CO |
| 3-416 | Cl | Cl | CF₃ | H | Me | CF₃CH₂CO |
| 3-417 | Cl | Cl | CF₃ | H | Me | EtNHCO |
| 3-418 | Cl | Cl | CF₃ | H | Me | tert-BuOC(=O) |
| 3-419 | Cl | H | CF₃ | H | Me | H |
| 3-420 | Cl | H | CF₃ | H | Me | MeCO |
| 3-421 | Cl | H | CF₃ | H | Me | EtCO |
| 3-422 | Cl | H | CF₃ | H | Me | cyclo-PrCO |
| 3-423 | Cl | H | CF₃ | H | Me | CH₃SCH₂CO |
| 3-424 | Cl | H | CF₃ | H | Me | CF₃CH₂CO |
| 3-425 | Cl | H | CF₃ | H | Me | EtNHCO |
| 3-426 | Cl | H | CF₃ | H | Me | tert-BuOC(=O) |
| 3-427 | F | H | CF₃ | H | Me | H |
| 3-428 | F | H | CF₃ | H | Me | MeCO |
| 3-429 | F | H | CF₃ | H | Me | EtCO |
| 3-430 | F | H | CF₃ | H | Me | cyclo-PrCO |
| 3-431 | F | H | CF₃ | H | Me | CH₃SCH₂CO |
| 3-432 | F | H | CF₃ | H | Me | CF₃CH₂CO |
| 3-433 | F | H | CF₃ | H | Me | EtNHCO |
| 3-434 | F | H | CF₃ | H | Me | tert-BuOC(=O) |
| 3-435 | H | F | CF₃ | H | Me | H |
| 3-436 | H | F | CF₃ | H | Me | MeCO |
| 3-437 | H | F | CF₃ | H | Me | EtCO |
| 3-438 | H | F | CF₃ | H | Me | cyclo-PrCO |
| 3-439 | H | F | CF₃ | H | Me | CH₃SCH₂CO |
| 3-440 | H | F | CF₃ | H | Me | CF₃CH₂CO |
| 3-441 | H | F | CF₃ | H | Me | EtNHCO |
| 3-442 | H | F | CF₃ | H | Me | tert-BuOC(=O) |
| 3-443 | OCF₃ | H | H | CF₃ | H | EtCO |
| 3-444 | SCF₃ | H | H | CF₃ | H | EtCO |
| 3-445 | SOCF₃ | H | H | CF₃ | H | EtCO |
| 3-446 | SO₂CF₃ | H | H | CF₃ | H | EtCO |

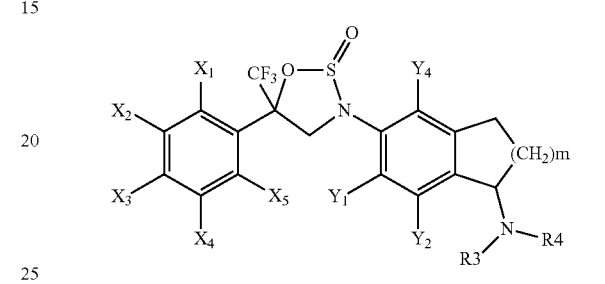

Wherein $X^1$, $X^5$, $Y^1$, $Y^2$, $Y^4$ and $R^3$ represent hydrogen.

TABLE 4

| Compound No. | X² | X³ | X⁴ | R⁴ | m |
|---|---|---|---|---|---|
| 4-1 | Cl | H | Cl | H | 1 |
| 4-2 | Cl | H | Cl | MeCO | 1 |
| 4-3 | Cl | H | Cl | EtCO | 1 |
| 4-4 | Cl | H | Cl | n-PrCO | 1 |
| 4-5 | Cl | H | Cl | cyclo-PrCO | 1 |
| 4-6 | Cl | H | Cl | cyclo-PrCH₂CO | 1 |
| 4-7 | Cl | H | Cl | CF₃CH₂CO | 1 |
| 4-8 | Cl | H | Cl | CH₃SCH₂CO | 1 |
| 4-9 | Cl | H | Cl | CH₃SOCH₂CO | 1 |
| 4-10 | Cl | H | Cl | CH₃SO₂CH₂CO | 1 |
| 4-11 | Cl | H | Cl | CH₃OCH₂CH₂CO | 1 |
| 4-12 | Cl | H | Cl | CH₃OCH(Me)CH₂CO | 1 |
| 4-13 | Cl | H | Cl | EtNHCO | 1 |
| 4-14 | Cl | H | Cl | tert-BuOC(=O) | 1 |
| 4-15 | Br | H | Br | H | 1 |
| 4-16 | Br | H | Br | MeCO | 1 |
| 4-17 | Br | H | Br | EtCO | 1 |
| 4-18 | Br | H | Br | n-PrCO | 1 |
| 4-19 | Br | H | Br | cyclo-PrCO | 1 |
| 4-20 | Br | H | Br | cyclo-PrCH₂CO | 1 |
| 4-21 | Br | H | Br | CF₃CH₂CO | 1 |
| 4-22 | Br | H | Br | CH₃SCH₂CO | 1 |
| 4-23 | Br | H | Br | CH₃SOCH₂CO | 1 |
| 4-24 | Br | H | Br | CH₃SO₂CH₂CO | 1 |
| 4-25 | Br | H | Br | CH₃OCH₂CH₂CO | 1 |
| 4-26 | Br | H | Br | CH₃OCH(Me)CH₂CO | 1 |
| 4-27 | Br | H | Br | EtNHCO | 1 |
| 4-28 | Br | H | Br | tert-BuOC(=O) | 1 |
| 4-29 | Cl | Cl | Cl | H | 1 |
| 4-30 | Cl | Cl | Cl | MeCO | 1 |
| 4-31 | Cl | Cl | Cl | EtCO | 1 |
| 4-32 | Cl | Cl | Cl | n-PrCO | 1 |
| 4-33 | Cl | Cl | Cl | cyclo-PrCO | 1 |
| 4-34 | Cl | Cl | Cl | cyclo-PrCH₂CO | 1 |
| 4-35 | Cl | Cl | Cl | CF₃CH₂CO | 1 |
| 4-36 | Cl | Cl | Cl | CH₃SCH₂CO | 1 |
| 4-37 | Cl | Cl | Cl | CH₃SOCH₂CO | 1 |
| 4-38 | Cl | Cl | Cl | CH₃SO₂CH₂CO | 1 |
| 4-39 | Cl | Cl | Cl | CH₃OCH₂CH₂CO | 1 |
| 4-40 | Cl | Cl | Cl | CH₃OCH(Me)CH₂CO | 1 |
| 4-41 | Cl | Cl | Cl | EtNHCO | 1 |
| 4-42 | Cl | Cl | Cl | tert-BuOC(=O) | 1 |
| 4-43 | CF₃ | H | H | H | 1 |

TABLE 4-continued

| Compound No. | $X^2$ | $X^3$ | $X^4$ | $R^4$ | m |
|---|---|---|---|---|---|
| 4-44 | $CF_3$ | H | H | MeCO | 1 |
| 4-45 | $CF_3$ | H | H | EtCO | 1 |
| 4-46 | $CF_3$ | H | H | n-PrCO | 1 |
| 4-47 | $CF_3$ | H | H | cyclo-PrCO | 1 |
| 4-48 | $CF_3$ | H | H | cyclo-PrCH$_2$CO | 1 |
| 4-49 | $CF_3$ | H | H | CF$_3$CH$_2$CO | 1 |
| 4-50 | $CF_3$ | H | H | CH$_3$SCH$_2$CO | 1 |
| 4-51 | $CF_3$ | H | H | CH$_3$SOCH$_2$CO | 1 |
| 4-52 | $CF_3$ | H | H | CH$_3$SO$_2$CH$_2$CO | 1 |
| 4-53 | $CF_3$ | H | H | CH$_3$OCH$_2$CH$_2$CO | 1 |
| 4-54 | $CF_3$ | H | H | CH$_3$OCH(Me)CH$_2$CO | 1 |
| 4-55 | $CF_3$ | H | H | EtNHCO | 1 |
| 4-56 | $CF_3$ | H | H | tert-BuOC(=O) | 1 |
| 4-57 | $CF_3$ | H | $CF_3$ | H | 1 |
| 4-58 | $CF_3$ | H | $CF_3$ | MeCO | 1 |
| 4-59 | $CF_3$ | H | $CF_3$ | EtCO | 1 |
| 4-60 | $CF_3$ | H | $CF_3$ | n-PrCO | 1 |
| 4-61 | $CF_3$ | H | $CF_3$ | cyclo-PrCO | 1 |
| 4-62 | $CF_3$ | H | $CF_3$ | cyclo-PrCH$_2$CO | 1 |
| 4-63 | $CF_3$ | H | $CF_3$ | CF$_3$CH$_2$CO | 1 |
| 4-64 | $CF_3$ | H | $CF_3$ | CH$_3$SCH$_2$CO | 1 |
| 4-65 | $CF_3$ | H | $CF_3$ | CH$_3$SOCH$_2$CO | 1 |
| 4-66 | $CF_3$ | H | $CF_3$ | CH$_3$SO$_2$CH$_2$CO | 1 |
| 4-67 | $CF_3$ | H | $CF_3$ | CH$_3$OCH$_2$CH$_2$CO | 1 |
| 4-68 | $CF_3$ | H | $CF_3$ | CH$_3$OCH(Me)CH$_2$CO | 1 |
| 4-69 | $CF_3$ | H | $CF_3$ | EtNHCO | 1 |
| 4-70 | $CF_3$ | H | $CF_3$ | tert-BuOC(=O) | 1 |
| 4-71 | Cl | Cl | $CF_3$ | H | 1 |
| 4-72 | Cl | Cl | $CF_3$ | MeCO | 1 |
| 4-73 | Cl | Cl | $CF_3$ | EtCO | 1 |
| 4-74 | Cl | Cl | $CF_3$ | cyclo-PrCO | 1 |
| 4-75 | Cl | Cl | $CF_3$ | CH$_3$SCH$_2$CO | 1 |
| 4-76 | Cl | Cl | $CF_3$ | CF$_3$CH$_2$CO | 1 |
| 4-77 | Cl | Cl | $CF_3$ | EtNHCO | 1 |
| 4-78 | Cl | Cl | $CF_3$ | tert-BuOC(=O) | 1 |
| 4-79 | Cl | H | $CF_3$ | H | 1 |
| 4-80 | Cl | H | $CF_3$ | MeCO | 1 |
| 4-81 | Cl | H | $CF_3$ | EtCO | 1 |
| 4-82 | Cl | H | $CF_3$ | cyclo-PrCO | 1 |
| 4-83 | Cl | H | $CF_3$ | CH$_3$SCH$_2$CO | 1 |
| 4-84 | Cl | H | $CF_3$ | CF$_3$CH$_2$CO | 1 |
| 4-85 | Cl | H | $CF_3$ | EtNHCO | 1 |
| 4-86 | Cl | H | $CF_3$ | tert-BuOC(=O) | 1 |
| 4-87 | F | H | $CF_3$ | H | 1 |
| 4-88 | F | H | $CF_3$ | MeCO | 1 |
| 4-89 | F | H | $CF_3$ | EtCO | 1 |
| 4-90 | F | H | $CF_3$ | cyclo-PrCO | 1 |
| 4-91 | F | H | $CF_3$ | CH$_3$SCH$_2$CO | 1 |
| 4-92 | F | H | $CF_3$ | CF$_3$CH$_2$CO | 1 |
| 4-93 | F | H | $CF_3$ | EtNHCO | 1 |
| 4-94 | F | H | $CF_3$ | tert-BuOC(=O) | 1 |
| 4-95 | H | F | $CF_3$ | H | 1 |
| 4-96 | H | F | $CF_3$ | MeCO | 1 |
| 4-97 | H | F | $CF_3$ | EtCO | 1 |
| 4-98 | H | F | $CF_3$ | cyclo-PrCO | 1 |
| 4-99 | H | F | $CF_3$ | CH$_3$SCH$_2$CO | 1 |
| 4-100 | H | F | $CF_3$ | CF$_3$CH$_2$CO | 1 |
| 4-101 | H | F | $CF_3$ | EtNHCO | 1 |
| 4-102 | H | F | $CF_3$ | tert-BuOC(=O) | 1 |
| 4-103 | Cl | H | Cl | H | 2 |
| 4-104 | Cl | H | Cl | MeCO | 2 |
| 4-105 | Cl | H | Cl | EtCO | 2 |
| 4-106 | Cl | H | Cl | n-PrCO | 2 |
| 4-107 | Cl | H | Cl | cyclo-PrCO | 2 |
| 4-108 | Cl | H | Cl | cyclo-PrCH$_2$CO | 2 |
| 4-109 | Cl | H | Cl | CF$_3$CH$_2$CO | 2 |
| 4-110 | Cl | H | Cl | CH$_3$SCH$_2$CO | 2 |
| 4-111 | Cl | H | Cl | CH$_3$SOCH$_2$CO | 2 |
| 4-112 | Cl | H | Cl | CH$_3$SO$_2$CH$_2$CO | 2 |
| 4-113 | Cl | H | Cl | CH$_3$OCH$_2$CH$_2$CO | 2 |
| 4-114 | Cl | H | Cl | CH$_3$OCH(Me)CH$_2$CO | 2 |
| 4-115 | Cl | H | Cl | EtNHCO | 2 |
| 4-116 | Cl | H | Cl | tert-BuOC(=O) | 2 |
| 4-117 | Br | H | Br | H | 2 |
| 4-118 | Br | H | Br | MeCO | 2 |
| 4-119 | Br | H | Br | EtCO | 2 |
| 4-120 | Br | H | Br | n-PrCO | 2 |
| 4-121 | Br | H | Br | cyclo-PrCO | 2 |
| 4-122 | Br | H | Br | cyclo-PrCH$_2$CO | 2 |
| 4-123 | Br | H | Br | CF$_3$CH$_2$CO | 2 |
| 4-124 | Br | H | Br | CH$_3$SCH$_2$CO | 2 |
| 4-125 | Br | H | Br | CH$_3$SOCH$_2$CO | 2 |
| 4-126 | Br | H | Br | CH$_3$SO$_2$CH$_2$CO | 2 |
| 4-127 | Br | H | Br | CH$_3$OCH$_2$CH$_2$CO | 2 |
| 4-128 | Br | H | Br | CH$_3$OCH(Me)CH$_2$CO | 2 |
| 4-129 | Br | H | Br | EtNHCO | 2 |
| 4-130 | Br | H | Br | tert-BuOC(=O) | 2 |
| 4-131 | Cl | Cl | Cl | H | 2 |
| 4-132 | Cl | Cl | Cl | MeCO | 2 |
| 4-133 | Cl | Cl | Cl | EtCO | 2 |
| 4-134 | Cl | Cl | Cl | n-PrCO | 2 |
| 4-135 | Cl | Cl | Cl | cyclo-PrCO | 2 |
| 4-136 | Cl | Cl | Cl | cyclo-PrCH$_2$CO | 2 |
| 4-137 | Cl | Cl | Cl | CF$_3$CH$_2$CO | 2 |
| 4-138 | Cl | Cl | Cl | CH$_3$SCH$_2$CO | 2 |
| 4-139 | Cl | Cl | Cl | CH$_3$SOCH$_2$CO | 2 |
| 4-140 | Cl | Cl | Cl | CH$_3$SO$_2$CH$_2$CO | 2 |
| 4-141 | Cl | Cl | Cl | CH$_3$OCH$_2$CH$_2$CO | 2 |
| 4-142 | Cl | Cl | Cl | CH$_3$OCH(Me)CH$_2$CO | 2 |
| 4-143 | Cl | Cl | Cl | EtNHCO | 2 |
| 4-144 | Cl | Cl | Cl | tert-BuOC(=O) | 2 |
| 4-145 | $CF_3$ | H | H | H | 2 |
| 4-146 | $CF_3$ | H | H | MeCO | 2 |
| 4-147 | $CF_3$ | H | H | EtCO | 2 |
| 4-148 | $CF_3$ | H | H | n-PrCO | 2 |
| 4-149 | $CF_3$ | H | H | cyclo-PrCO | 2 |
| 4-150 | $CF_3$ | H | H | cyclo-PrCH$_2$CO | 2 |
| 4-151 | $CF_3$ | H | H | CF$_3$CH$_2$CO | 2 |
| 4-152 | $CF_3$ | H | H | CH$_3$SCH$_2$CO | 2 |
| 4-153 | $CF_3$ | H | H | CH$_3$SOCH$_2$CO | 2 |
| 4-154 | $CF_3$ | H | H | CH$_3$SO$_2$CH$_2$CO | 2 |
| 4-155 | $CF_3$ | H | H | CH$_3$OCH$_2$CH$_2$CO | 2 |
| 4-156 | $CF_3$ | H | H | CH$_3$OCH(Me)CH$_2$CO | 2 |
| 4-157 | $CF_3$ | H | H | EtNHCO | 2 |
| 4-158 | $CF_3$ | H | H | tert-BuOC(=O) | 2 |
| 4-159 | $CF_3$ | H | $CF_3$ | H | 2 |
| 4-160 | $CF_3$ | H | $CF_3$ | MeCO | 2 |
| 4-161 | $CF_3$ | H | $CF_3$ | EtCO | 2 |
| 4-162 | $CF_3$ | H | $CF_3$ | n-PrCO | 2 |
| 4-163 | $CF_3$ | H | $CF_3$ | cyclo-PrCO | 2 |
| 4-164 | $CF_3$ | H | $CF_3$ | cyclo-PrCH$_2$CO | 2 |
| 4-165 | $CF_3$ | H | $CF_3$ | CF$_3$CH$_2$CO | 2 |
| 4-166 | $CF_3$ | H | $CF_3$ | CH$_3$SCH$_2$CO | 2 |
| 4-167 | $CF_3$ | H | $CF_3$ | CH$_3$SOCH$_2$CO | 2 |
| 4-168 | $CF_3$ | H | $CF_3$ | CH$_3$SO$_2$CH$_2$CO | 2 |
| 4-169 | $CF_3$ | H | $CF_3$ | CH$_3$OCH$_2$CH$_2$CO | 2 |
| 4-170 | $CF_3$ | H | $CF_3$ | CH$_3$OCH(Me)CH$_2$CO | 2 |
| 4-171 | $CF_3$ | H | $CF_3$ | EtNHCO | 2 |
| 4-172 | $CF_3$ | H | $CF_3$ | tert-BuOC(=O) | 2 |
| 4-173 | Cl | Cl | $CF_3$ | H | 2 |
| 4-174 | Cl | Cl | $CF_3$ | MeCO | 2 |
| 4-175 | Cl | Cl | $CF_3$ | EtCO | 2 |
| 4-176 | Cl | Cl | $CF_3$ | cyclo-PrCO | 2 |
| 4-177 | Cl | Cl | $CF_3$ | CH$_3$SCH$_2$CO | 2 |
| 4-178 | Cl | Cl | $CF_3$ | CF$_3$CH$_2$CO | 2 |
| 4-179 | Cl | Cl | $CF_3$ | EtNHCO | 2 |
| 4-180 | Cl | Cl | $CF_3$ | tert-BuOC(=O) | 2 |
| 4-181 | Cl | H | $CF_3$ | H | 2 |
| 4-182 | Cl | H | $CF_3$ | MeCO | 2 |
| 4-183 | Cl | H | $CF_3$ | EtCO | 2 |
| 4-184 | Cl | H | $CF_3$ | cyclo-PrCO | 2 |
| 4-185 | Cl | H | $CF_3$ | CH$_3$SCH$_2$CO | 2 |
| 4-186 | Cl | H | $CF_3$ | CF$_3$CH$_2$CO | 2 |
| 4-187 | Cl | H | $CF_3$ | EtNHCO | 2 |
| 4-188 | Cl | H | $CF_3$ | tert-BuOC(=O) | 2 |
| 4-189 | F | H | $CF_3$ | H | 2 |
| 4-190 | F | H | $CF_3$ | MeCO | 2 |
| 4-191 | F | H | $CF_3$ | EtCO | 2 |
| 4-192 | F | H | $CF_3$ | cyclo-PrCO | 2 |
| 4-193 | F | H | $CF_3$ | CH$_3$SCH$_2$CO | 2 |
| 4-194 | F | H | $CF_3$ | CF$_3$CH$_2$CO | 2 |
| 4-195 | F | H | $CF_3$ | EtNHCO | 2 |
| 4-196 | F | H | $CF_3$ | tert-BuOC(=O) | 2 |
| 4-197 | H | F | $CF_3$ | H | 2 |
| 4-198 | H | F | $CF_3$ | MeCO | 2 |
| 4-199 | H | F | $CF_3$ | EtCO | 2 |

TABLE 4-continued

| Compound No. | X² | X³ | X⁴ | R⁴ | m |
|---|---|---|---|---|---|
| 4-200 | H | F | CF₃ | cyclo-PrCO | 2 |
| 4-201 | H | F | CF₃ | CH₃SCH₂CO | 2 |
| 4-202 | H | F | CF₃ | CF₃CH₂CO | 2 |
| 4-203 | H | F | CF₃ | EtNHCO | 2 |
| 4-204 | H | F | CF₃ | tert-BuOC(=O) | 2 |
| 4-205 | OCF₃ | H | H | EtCO | 1 |
| 4-206 | SCF₃ | H | H | EtCO | 1 |
| 4-207 | SOCF₃ | H | H | EtCO | 1 |
| 4-208 | SO₂CF₃ | H | H | EtCO | 1 |

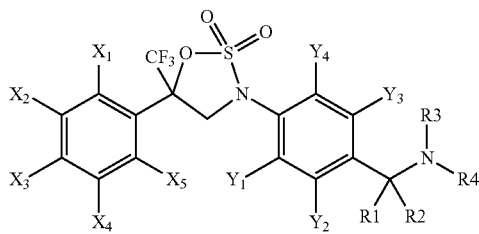

Wherein, X¹, X⁵, Y¹, Y², Y⁴, R² and R³ represent hydrogen.

TABLE 5

| Compound No. | X² | X³ | X⁴ | Y³ | R¹ | R⁴ |
|---|---|---|---|---|---|---|
| 5-1 | Cl | H | Cl | CF₃ | H | H |
| 5-2 | Cl | H | Cl | CF₃ | H | MeCO |
| 5-3 | Cl | H | Cl | CF₃ | H | EtCO |
| 5-4 | Cl | H | Cl | CF₃ | H | n-PrCO |
| 5-5 | Cl | H | Cl | CF₃ | H | cyclo-PrCO |
| 5-6 | Cl | H | Cl | CF₃ | H | cyclo-PrCH₂CO |
| 5-7 | Cl | H | Cl | CF₃ | H | CF₃CH₂CO |
| 5-8 | Cl | H | Cl | CF₃ | H | CH₃SCH₂CO |
| 5-9 | Cl | H | Cl | CF₃ | H | CH₃SOCH₂CO |
| 5-10 | Cl | H | Cl | CF₃ | H | CH₃SO₂CH₂CO |
| 5-11 | Cl | H | Cl | CF₃ | H | CH₃OCH₂CH₂CO |
| 5-12 | Cl | H | Cl | CF₃ | H | CH₃OCH(Me)CH₂CO |
| 5-13 | Cl | H | Cl | CF₃ | H | EtNHCO |
| 5-14 | Cl | H | Cl | CF₃ | H | tert-BuOC(=O) |
| 5-15 | Cl | Cl | Cl | CF₃ | H | H |
| 5-16 | Cl | Cl | Cl | CF₃ | H | MeCO |
| 5-17 | Cl | Cl | Cl | CF₃ | H | EtCO |
| 5-18 | Cl | Cl | Cl | CF₃ | H | n-PrCO |
| 5-19 | Cl | Cl | Cl | CF₃ | H | cyclo-PrCO |
| 5-20 | Cl | Cl | Cl | CF₃ | H | cyclo-PrCH₂CO |
| 5-21 | Cl | Cl | Cl | CF₃ | H | CF₃CH₂CO |
| 5-22 | Cl | Cl | Cl | CF₃ | H | CH₃SCH₂CO |
| 5-23 | Cl | Cl | Cl | CF₃ | H | CH₃SOCH₂CO |
| 5-24 | Cl | Cl | Cl | CF₃ | H | CH₃SO₂CH₂CO |
| 5-25 | Cl | Cl | Cl | CF₃ | H | CH₃OCH₂CH₂CO |
| 5-26 | Cl | Cl | Cl | CF₃ | H | CH₃OCH(Me)CH₂CO |
| 5-27 | Cl | Cl | Cl | CF₃ | H | EtNHCO |
| 5-28 | Cl | Cl | Cl | CF₃ | H | tert-BuOC(=O) |
| 5-29 | Cl | Cl | Cl | Cl | H | H |
| 5-30 | Cl | Cl | Cl | Cl | H | MeCO |
| 5-31 | Cl | Cl | Cl | Cl | H | EtCO |
| 5-32 | Cl | Cl | Cl | Cl | H | n-PrCO |
| 5-33 | Cl | Cl | Cl | Cl | H | cyclo-PrCO |
| 5-34 | Cl | Cl | Cl | Cl | H | cyclo-PrCH₂CO |
| 5-35 | Cl | Cl | Cl | Cl | H | CF₃CH₂CO |
| 5-36 | Cl | Cl | Cl | Cl | H | CH₃SCH₂CO |
| 5-37 | Cl | Cl | Cl | Cl | H | CH₃SOCH₂CO |
| 5-38 | Cl | Cl | Cl | Cl | H | CH₃SO₂CH₂CO |
| 5-39 | Cl | Cl | Cl | Cl | H | CH₃OCH₂CH₂CO |
| 5-40 | Cl | Cl | Cl | Cl | H | CH₃OCH(Me)CH₂CO |
| 5-41 | Cl | Cl | Cl | Cl | H | EtNHCO |
| 5-42 | Cl | Cl | Cl | Cl | H | tert-BuOC(=O) |
| 5-43 | Cl | Cl | Cl | Me | H | H |
| 5-44 | Cl | Cl | Cl | Me | H | MeCO |
| 5-45 | Cl | Cl | Cl | Me | H | EtCO |

TABLE 5-continued

| Compound No. | X² | X³ | X⁴ | Y³ | R¹ | R⁴ |
|---|---|---|---|---|---|---|
| 5-46 | Cl | Cl | Cl | Me | H | n-PrCO |
| 5-47 | Cl | Cl | Cl | Me | H | cyclo-PrCO |
| 5-48 | Cl | Cl | Cl | Me | H | cyclo-PrCH₂CO |
| 5-49 | Cl | Cl | Cl | Me | H | CF₃CH₂CO |
| 5-50 | Cl | Cl | Cl | Me | H | CH₃SCH₂CO |
| 5-51 | Cl | Cl | Cl | Me | H | CH₃SOCH₂CO |
| 5-52 | Cl | Cl | Cl | Me | H | CH₃SO₂CH₂CO |
| 5-53 | Cl | Cl | Cl | Me | H | CH₃OCH₂CH₂CO |
| 5-54 | Cl | Cl | Cl | Me | H | CH₃OCH(Me)CH₂CO |
| 5-55 | Cl | Cl | Cl | Me | H | EtNHCO |
| 5-56 | Cl | Cl | Cl | Me | H | tert-BuOC(=O) |
| 5-57 | Cl | Cl | Cl | H | H | H |
| 5-58 | Cl | Cl | Cl | H | H | MeCO |
| 5-59 | Cl | Cl | Cl | H | H | EtCO |
| 5-60 | Cl | Cl | Cl | H | H | n-PrCO |
| 5-61 | Cl | Cl | Cl | H | H | cyclo-PrCO |
| 5-62 | Cl | Cl | Cl | H | H | cyclo-PrCH₂CO |
| 5-63 | Cl | Cl | Cl | H | H | CF₃CH₂CO |
| 5-64 | Cl | Cl | Cl | H | H | CH₃SCH₂CO |
| 5-65 | Cl | Cl | Cl | H | H | CH₃SOCH₂CO |
| 5-66 | Cl | Cl | Cl | H | H | CH₃SO₂CH₂CO |
| 5-67 | Cl | Cl | Cl | H | H | CH₃OCH₂CH₂CO |
| 5-68 | Cl | Cl | Cl | H | H | CH₃OCH(Me)CH₂CO |
| 5-69 | Cl | Cl | Cl | H | H | EtNHCO |
| 5-70 | Cl | Cl | Cl | H | H | tert-BuOC(=O) |
| 5-71 | CF₃ | H | H | CF₃ | H | H |
| 5-72 | CF₃ | H | H | CF₃ | H | MeCO |
| 5-73 | CF₃ | H | H | CF₃ | H | EtCO |
| 5-74 | CF₃ | H | H | CF₃ | H | n-PrCO |
| 5-75 | CF₃ | H | H | CF₃ | H | cyclo-PrCO |
| 5-76 | CF₃ | H | H | CF₃ | H | cyclo-PrCH₂CO |
| 5-77 | CF₃ | H | H | CF₃ | H | CF₃CH₂CO |
| 5-78 | CF₃ | H | H | CF₃ | H | CH₃SCH₂CO |
| 5-79 | CF₃ | H | H | CF₃ | H | CH₃SOCH₂CO |
| 5-80 | CF₃ | H | H | CF₃ | H | CH₃SO₂CH₂CO |
| 5-81 | CF₃ | H | H | CF₃ | H | CH₃OCH₂CH₂CO |
| 5-82 | CF₃ | H | H | CF₃ | H | CH₃OCH(Me)CH₂CO |
| 5-83 | CF₃ | H | H | CF₃ | H | EtNHCO |
| 5-84 | CF₃ | H | H | CF₃ | H | tert-BuOC(=O) |
| 5-85 | CF₃ | H | H | Cl | H | H |
| 5-86 | CF₃ | H | H | Cl | H | MeCO |
| 5-87 | CF₃ | H | H | Cl | H | EtCO |
| 5-88 | CF₃ | H | H | Cl | H | n-PrCO |
| 5-89 | CF₃ | H | H | Cl | H | cyclo-PrCO |
| 5-90 | CF₃ | H | H | Cl | H | cyclo-PrCH₂CO |
| 5-91 | CF₃ | H | H | Cl | H | CF₃CH₂CO |
| 5-92 | CF₃ | H | H | Cl | H | CH₃SCH₂CO |
| 5-93 | CF₃ | H | H | Cl | H | CH₃SOCH₂CO |
| 5-94 | CF₃ | H | H | Cl | H | CH₃SO₂CH₂CO |
| 5-95 | CF₃ | H | H | Cl | H | CH₃OCH₂CH₂CO |
| 5-96 | CF₃ | H | H | Cl | H | CH₃OCH(Me)CH₂CO |
| 5-97 | CF₃ | H | H | Cl | H | EtNHCO |
| 5-98 | CF₃ | H | H | Cl | H | tert-BuOC(=O) |
| 5-99 | CF₃ | H | H | Me | H | H |
| 5-100 | CF₃ | H | H | Me | H | MeCO |
| 5-101 | CF₃ | H | H | Me | H | EtCO |
| 5-102 | CF₃ | H | H | Me | H | n-PrCO |
| 5-103 | CF₃ | H | H | Me | H | cyclo-PrCO |
| 5-104 | CF₃ | H | H | Me | H | cyclo-PrCH₂CO |
| 5-105 | CF₃ | H | H | Me | H | CF₃CH₂CO |
| 5-106 | CF₃ | H | H | Me | H | CH₃SCH₂CO |
| 5-107 | CF₃ | H | H | Me | H | CH₃SOCH₂CO |
| 5-108 | CF₃ | H | H | Me | H | CH₃SO₂CH₂CO |
| 5-109 | CF₃ | H | H | Me | H | CH₃OCH₂CH₂CO |
| 5-110 | CF₃ | H | H | Me | H | CH₃OCH(Me)CH₂CO |
| 5-111 | CF₃ | H | H | Me | H | EtNHCO |
| 5-112 | CF₃ | H | H | Me | H | tert-BuOC(=O) |
| 5-113 | CF₃ | H | H | H | H | H |
| 5-114 | CF₃ | H | H | H | H | MeCO |
| 5-115 | CF₃ | H | H | H | H | EtCO |
| 5-116 | CF₃ | H | H | H | H | n-PrCO |
| 5-117 | CF₃ | H | H | H | H | cyclo-PrCO |
| 5-118 | CF₃ | H | H | H | H | cyclo-PrCH₂CO |
| 5-119 | CF₃ | H | H | H | H | CF₃CH₂CO |
| 5-120 | CF₃ | H | H | H | H | CH₃SCH₂CO |
| 5-121 | CF₃ | H | H | H | H | CH₃SOCH₂CO |
| 5-122 | CF₃ | H | H | H | H | CH₃SO₂CH₂CO |
| 5-123 | CF₃ | H | H | H | H | CH₃OCH₂CH₂CO |

TABLE 5-continued

| Compound No. | X² | X³ | X⁴ | Y³ | R¹ | R⁴ |
|---|---|---|---|---|---|---|
| 5-124 | CF₃ | H | H | H | H | CH₃OCH(Me)CH₂CO |
| 5-125 | CF₃ | H | H | H | H | EtNHCO |
| 5-126 | CF₃ | H | H | H | H | tert-BuOC(=O) |
| 5-127 | CF₃ | H | CF₃ | CF₃ | H | H |
| 5-128 | CF₃ | H | CF₃ | CF₃ | H | MeCO |
| 5-129 | CF₃ | H | CF₃ | CF₃ | H | EtCO |
| 5-130 | CF₃ | H | CF₃ | CF₃ | H | n-PrCO |
| 5-131 | CF₃ | H | CF₃ | CF₃ | H | cyclo-PrCO |
| 5-132 | CF₃ | H | CF₃ | CF₃ | H | cyclo-PrCH₂CO |
| 5-133 | CF₃ | H | CF₃ | CF₃ | H | CF₃CH₂CO |
| 5-134 | CF₃ | H | CF₃ | CF₃ | H | CH₃SCH₂CO |
| 5-135 | CF₃ | H | CF₃ | CF₃ | H | CH₃SOCH₂CO |
| 5-136 | CF₃ | H | CF₃ | CF₃ | H | CH₃SO₂CH₂CO |
| 5-137 | CF₃ | H | CF₃ | CF₃ | H | CH₃OCH₂CH₂CO |
| 5-138 | CF₃ | H | CF₃ | CF₃ | H | CH₃OCH(Me)CH₂CO |
| 5-139 | CF₃ | H | CF₃ | CF₃ | H | EtNHCO |
| 5-140 | CF₃ | H | CF₃ | CF₃ | H | tert-BuOC(=O) |
| 5-141 | CF₃ | H | CF₃ | Cl | H | H |
| 5-142 | CF₃ | H | CF₃ | Cl | H | MeCO |
| 5-143 | CF₃ | H | CF₃ | Cl | H | EtCO |
| 5-144 | CF₃ | H | CF₃ | Cl | H | n-PrCO |
| 5-145 | CF₃ | H | CF₃ | Cl | H | cyclo-PrCO |
| 5-146 | CF₃ | H | CF₃ | Cl | H | cyclo-PrCH₂CO |
| 5-147 | CF₃ | H | CF₃ | Cl | H | CF₃CH₂CO |
| 5-148 | CF₃ | H | CF₃ | Cl | H | CH₃SCH₂CO |
| 5-149 | CF₃ | H | CF₃ | Cl | H | CH₃SOCH₂CO |
| 5-150 | CF₃ | H | CF₃ | Cl | H | CH₃SO₂CH₂CO |
| 5-151 | CF₃ | H | CF₃ | Cl | H | CH₃OCH₂CH₂CO |
| 5-152 | CF₃ | H | CF₃ | Cl | H | CH₃OCH(Me)CH₂CO |
| 5-153 | CF₃ | H | CF₃ | Cl | H | EtNHCO |
| 5-154 | CF₃ | H | CF₃ | Cl | H | tert-BuOC(=O) |
| 5-155 | CF₃ | H | CF₃ | Me | H | H |
| 5-156 | CF₃ | H | CF₃ | Me | H | MeCO |
| 5-157 | CF₃ | H | CF₃ | Me | H | EtCO |
| 5-158 | CF₃ | H | CF₃ | Me | H | n-PrCO |
| 5-159 | CF₃ | H | CF₃ | Me | H | cyclo-PrCO |
| 5-160 | CF₃ | H | CF₃ | Me | H | cyclo-PrCH₂CO |
| 5-161 | CF₃ | H | CF₃ | Me | H | CF₃CH₂CO |
| 5-162 | CF₃ | H | CF₃ | Me | H | CH₃SCH₂CO |
| 5-163 | CF₃ | H | CF₃ | Me | H | CH₃SOCH₂CO |
| 5-164 | CF₃ | H | CF₃ | Me | H | CH₃SO₂CH₂CO |
| 5-165 | CF₃ | H | CF₃ | Me | H | CH₃OCH₂CH₂CO |
| 5-166 | CF₃ | H | CF₃ | Me | H | CH₃OCH(Me)CH₂CO |
| 5-167 | CF₃ | H | CF₃ | Me | H | EtNHCO |
| 5-168 | CF₃ | H | CF₃ | Me | H | tert-BuOC(=O) |
| 5-169 | CF₃ | H | CF₃ | H | H | H |
| 5-170 | CF₃ | H | CF₃ | H | H | MeCO |
| 5-171 | CF₃ | H | CF₃ | H | H | EtCO |
| 5-172 | CF₃ | H | CF₃ | H | H | n-PrCO |
| 5-173 | CF₃ | H | CF₃ | H | H | cyclo-PrCO |
| 5-174 | CF₃ | H | CF₃ | H | H | cyclo-PrCH₂CO |
| 5-175 | CF₃ | H | CF₃ | H | H | CF₃CH₂CO |
| 5-176 | CF₃ | H | CF₃ | H | H | CH₃SCH₂CO |
| 5-177 | CF₃ | H | CF₃ | H | H | CH₃SOCH₂CO |
| 5-178 | CF₃ | H | CF₃ | H | H | CH₃SO₂CH₂CO |
| 5-179 | CF₃ | H | CF₃ | H | H | CH₃OCH₂CH₂CO |
| 5-180 | CF₃ | H | CF₃ | H | H | CH₃OCH(Me)CH₂CO |
| 5-181 | CF₃ | H | CF₃ | H | H | EtNHCO |
| 5-182 | CF₃ | H | CF₃ | H | H | tert-BuOC(=O) |
| 5-183 | Cl | Cl | CF₃ | CF₃ | H | H |
| 5-184 | Cl | Cl | CF₃ | CF₃ | H | MeCO |
| 5-185 | Cl | Cl | CF₃ | CF₃ | H | EtCO |
| 5-186 | Cl | Cl | CF₃ | CF₃ | H | cyclo-PrCO |
| 5-187 | Cl | Cl | CF₃ | CF₃ | H | CH₃SCH₂CO |
| 5-188 | Cl | Cl | CF₃ | CF₃ | H | CF₃CH₂CO |
| 5-189 | Cl | Cl | CF₃ | CF₃ | H | EtNHCO |
| 5-190 | Cl | Cl | CF₃ | CF₃ | H | tert-BuOC(=O) |
| 5-191 | Cl | H | CF₃ | CF₃ | H | H |
| 5-192 | Cl | H | CF₃ | CF₃ | H | MeCO |
| 5-193 | Cl | H | CF₃ | CF₃ | H | EtCO |
| 5-194 | Cl | H | CF₃ | CF₃ | H | cyclo-PrCO |
| 5-195 | Cl | H | CF₃ | CF₃ | H | CH₃SCH₂CO |
| 5-196 | Cl | H | CF₃ | CF₃ | H | CF₃CH₂CO |
| 5-197 | Cl | H | CF₃ | CF₃ | H | EtNHCO |
| 5-198 | Cl | H | CF₃ | CF₃ | H | tert-BuOC(=O) |
| 5-199 | F | H | CF₃ | CF₃ | H | H |
| 5-200 | F | H | CF₃ | CF₃ | H | MeCO |
| 5-201 | F | H | CF₃ | CF₃ | H | EtCO |
| 5-202 | F | H | CF₃ | CF₃ | H | cyclo-PrCO |
| 5-203 | F | H | CF₃ | CF₃ | H | CH₃SCH₂CO |
| 5-204 | F | H | CF₃ | CF₃ | H | CF₃CH₂CO |
| 5-205 | F | H | CF₃ | CF₃ | H | EtNHCO |
| 5-206 | F | H | CF₃ | CF₃ | H | tert-BuOC(=O) |
| 5-207 | H | F | CF₃ | CF₃ | H | H |
| 5-208 | H | F | CF₃ | CF₃ | H | MeCO |
| 5-209 | H | F | CF₃ | CF₃ | H | EtCO |
| 5-210 | H | F | CF₃ | CF₃ | H | cyclo-PrCO |
| 5-211 | H | F | CF₃ | CF₃ | H | CH₃SCH₂CO |
| 5-212 | H | F | CF₃ | CF₃ | H | CF₃CH₂CO |
| 5-213 | H | F | CF₃ | CF₃ | H | EtNHCO |
| 5-214 | H | F | CF₃ | CF₃ | H | tert-BuOC(=O) |
| 5-215 | Cl | H | Cl | Br | H | H |
| 5-216 | Cl | H | Cl | Br | H | MeCO |
| 5-217 | Cl | H | Cl | Br | H | EtCO |
| 5-218 | Cl | H | Cl | Br | H | n-PrCO |
| 5-219 | Cl | H | Cl | Br | H | cyclo-PrCO |
| 5-220 | Cl | H | Cl | Br | H | cyclo-PrCH₂CO |
| 5-221 | Cl | H | Cl | Br | H | CF₃CH₂CO |
| 5-222 | Cl | H | Cl | Br | H | CH₃SCH₂CO |
| 5-223 | Cl | H | Cl | Br | H | CH₃SOCH₂CO |
| 5-224 | Cl | H | Cl | Br | H | CH₃SO₂CH₂CO |
| 5-225 | Cl | H | Cl | Br | H | CH₃OCH₂CH₂CO |
| 5-226 | Cl | H | Cl | Br | H | CH₃OCH(Me)CH₂CO |
| 5-227 | Cl | H | Cl | Br | H | EtNHCO |
| 5-228 | Cl | H | Cl | Br | H | tert-BuOC(=O) |
| 5-229 | Cl | Cl | Cl | Br | H | H |
| 5-230 | Cl | Cl | Cl | Br | H | MeCO |
| 5-231 | Cl | Cl | Cl | Br | H | EtCO |
| 5-232 | Cl | Cl | Cl | Br | H | n-PrCO |
| 5-233 | Cl | Cl | Cl | Br | H | cyclo-PrCO |
| 5-234 | Cl | Cl | Cl | Br | H | cyclo-PrCH₂CO |
| 5-235 | Cl | Cl | Cl | Br | H | CF₃CH₂CO |
| 5-236 | Cl | Cl | Cl | Br | H | CH₃SCH₂CO |
| 5-237 | Cl | Cl | Cl | Br | H | CH₃SOCH₂CO |
| 5-238 | Cl | Cl | Cl | Br | H | CH₃SO₂CH₂CO |
| 5-239 | Cl | Cl | Cl | Br | H | CH₃OCH₂CH₂CO |
| 5-240 | Cl | Cl | Cl | Br | H | CH₃OCH(Me)CH₂CO |
| 5-241 | Cl | Cl | Cl | Br | H | EtNHCO |
| 5-242 | Cl | Cl | Cl | Br | H | tert-BuOC(=O) |
| 5-243 | CF₃ | H | H | Br | H | H |
| 5-244 | CF₃ | H | H | Br | H | MeCO |
| 5-245 | CF₃ | H | H | Br | H | EtCO |
| 5-246 | CF₃ | H | H | Br | H | n-PrCO |
| 5-247 | CF₃ | H | H | Br | H | cyclo-PrCO |
| 5-248 | CF₃ | H | H | Br | H | cyclo-PrCH₂CO |
| 5-249 | CF₃ | H | H | Br | H | CF₃CH₂CO |
| 5-250 | CF₃ | H | H | Br | H | CH₃SCH₂CO |
| 5-251 | CF₃ | H | H | Br | H | CH₃SOCH₂CO |
| 5-252 | CF₃ | H | H | Br | H | CH₃SO₂CH₂CO |
| 5-253 | CF₃ | H | H | Br | H | CH₃OCH₂CH₂CO |
| 5-254 | CF₃ | H | H | Br | H | CH₃OCH(Me)CH₂CO |
| 5-255 | CF₃ | H | H | Br | H | EtNHCO |
| 5-256 | CF₃ | H | H | Br | H | tert-BuOC(=O) |
| 5-257 | CF₃ | H | CF₃ | Br | H | H |
| 5-258 | CF₃ | H | CF₃ | Br | H | MeCO |
| 5-259 | CF₃ | H | CF₃ | Br | H | EtCO |
| 5-260 | CF₃ | H | CF₃ | Br | H | n-PrCO |
| 5-261 | CF₃ | H | CF₃ | Br | H | cyclo-PrCO |
| 5-262 | CF₃ | H | CF₃ | Br | H | cyclo-PrCH₂CO |
| 5-263 | CF₃ | H | CF₃ | Br | H | CF₃CH₂CO |
| 5-264 | CF₃ | H | CF₃ | Br | H | CH₃SCH₂CO |
| 5-265 | CF₃ | H | CF₃ | Br | H | CH₃SOCH₂CO |
| 5-266 | CF₃ | H | CF₃ | Br | H | CH₃SO₂CH₂CO |
| 5-267 | CF₃ | H | CF₃ | Br | H | CH₃OCH₂CH₂CO |
| 5-268 | CF₃ | H | CF₃ | Br | H | CH₃OCH(Me)CH₂CO |
| 5-269 | CF₃ | H | CF₃ | Br | H | EtNHCO |
| 5-270 | CF₃ | H | CF₃ | Br | H | tert-BuOC(=O) |
| 5-271 | Br | H | Br | CF₃ | H | H |
| 5-272 | Br | H | Br | CF₃ | H | MeCO |
| 5-273 | Br | H | Br | CF₃ | H | EtCO |
| 5-274 | Br | H | Br | CF₃ | H | n-PrCO |
| 5-275 | Br | H | Br | CF₃ | H | cyclo-PrCO |
| 5-276 | Br | H | Br | CF₃ | H | cyclo-PrCH₂CO |
| 5-277 | Br | H | Br | CF₃ | H | CF₃CH₂CO |
| 5-278 | Br | H | Br | CF₃ | H | CH₃SCH₂CO |
| 5-279 | Br | H | Br | CF₃ | H | CH₃SOCH₂CO |

TABLE 5-continued

| Compound No. | X² | X³ | X⁴ | Y³ | R¹ | R⁴ |
|---|---|---|---|---|---|---|
| 5-280 | Br | H | Br | CF₃ | H | CH₃SO₂CH₂CO |
| 5-281 | Br | H | Br | CF₃ | H | CH₃OCH₂CH₂CO |
| 5-282 | Br | H | Br | CF₃ | H | CH₃OCH(Me)CH₂CO |
| 5-283 | Br | H | Br | CF₃ | H | EtNHCO |
| 5-284 | Br | H | Br | CF₃ | H | tert-BuOC(=O) |
| 5-285 | Br | H | Br | Cl | H | H |
| 5-286 | Br | H | Br | Cl | H | MeCO |
| 5-287 | Br | H | Br | Cl | H | EtCO |
| 5-288 | Br | H | Br | Cl | H | n-PrCO |
| 5-289 | Br | H | Br | Cl | H | cyclo-PrCO |
| 5-290 | Br | H | Br | Cl | H | cyclo-PrCH₂CO |
| 5-291 | Br | H | Br | Cl | H | CF₃CH₂CO |
| 5-292 | Br | H | Br | Cl | H | CH₃SCH₂CO |
| 5-293 | Br | H | Br | Cl | H | CH₃SOCH₂CO |
| 5-294 | Br | H | Br | Cl | H | CH₃SO₂CH₂CO |
| 5-295 | Br | H | Br | Cl | H | CH₃OCH₂CH₂CO |
| 5-296 | Br | H | Br | Cl | H | CH₃OCH(Me)CH₂CO |
| 5-297 | Br | H | Br | Cl | H | EtNHCO |
| 5-298 | Br | H | Br | Cl | H | tert-BuOC(=O) |
| 5-299 | Br | H | Br | Br | H | H |
| 5-300 | Br | H | Br | Br | H | MeCO |
| 5-301 | Br | H | Br | Br | H | EtCO |
| 5-302 | Br | H | Br | Br | H | n-PrCO |
| 5-303 | Br | H | Br | Br | H | cyclo-PrCO |
| 5-304 | Br | H | Br | Br | H | cyclo-PrCH₂CO |
| 5-305 | Br | H | Br | Br | H | CF₃CH₂CO |
| 5-306 | Br | H | Br | Br | H | CH₃SCH₂CO |
| 5-307 | Br | H | Br | Br | H | CH₃SOCH₂CO |
| 5-308 | Br | H | Br | Br | H | CH₃SO₂CH₂CO |
| 5-309 | Br | H | Br | Br | H | CH₃OCH₂CH₂CO |
| 5-310 | Br | H | Br | Br | H | CH₃OCH(Me)CH₂CO |
| 5-311 | Br | H | Br | Br | H | EtNHCO |
| 5-312 | Br | H | Br | Br | H | tert-BuOC(=O) |
| 5-313 | Br | H | Br | Me | H | H |
| 5-314 | Br | H | Br | Me | H | MeCO |
| 5-315 | Br | H | Br | Me | H | EtCO |
| 5-316 | Br | H | Br | Me | H | n-PrCO |
| 5-317 | Br | H | Br | Me | H | cyclo-PrCO |
| 5-318 | Br | H | Br | Me | H | cyclo-PrCH₂CO |
| 5-319 | Br | H | Br | Me | H | CF₃CH₂CO |
| 5-320 | Br | H | Br | Me | H | CH₃SCH₂CO |
| 5-321 | Br | H | Br | Me | H | CH₃SOCH₂CO |
| 5-322 | Br | H | Br | Me | H | CH₃SO₂CH₂CO |
| 5-323 | Br | H | Br | Me | H | CH₃OCH₂CH₂CO |
| 5-324 | Br | H | Br | Me | H | CH₃OCH(Me)CH₂CO |
| 5-325 | Br | H | Br | Me | H | EtNHCO |
| 5-326 | Br | H | Br | Me | H | tert-BuOC(=O) |
| 5-327 | Br | H | Br | H | H | H |
| 5-328 | Br | H | Br | H | H | MeCO |
| 5-329 | Br | H | Br | H | H | EtCO |
| 5-330 | Br | H | Br | H | H | n-PrCO |
| 5-331 | Br | H | Br | H | H | cyclo-PrCO |
| 5-332 | Br | H | Br | H | H | cyclo-PrCH₂CO |
| 5-333 | Br | H | Br | H | H | CF₃CH₂CO |
| 5-334 | Br | H | Br | H | H | CH₃SCH₂CO |
| 5-335 | Br | H | Br | H | H | CH₃SOCH₂CO |
| 5-336 | Br | H | Br | H | H | CH₃SO₂CH₂CO |
| 5-337 | Br | H | Br | H | H | CH₃OCH₂CH₂CO |
| 5-338 | Br | H | Br | H | H | CH₃OCH(Me)CH₂CO |
| 5-339 | Br | H | Br | H | H | EtNHCO |
| 5-340 | Br | H | Br | H | H | tert-BuOC(=O) |
| 5-341 | Cl | H | Cl | H | Me | H |
| 5-342 | Cl | H | Cl | H | Me | MeCO |
| 5-343 | Cl | H | Cl | H | Me | EtCO |
| 5-344 | Cl | H | Cl | H | Me | n-PrCO |
| 5-345 | Cl | H | Cl | H | Me | cyclo-PrCO |
| 5-345-a | Cl | H | Cl | H | Me | cyclo-PrCO |
| 5-346 | Cl | H | Cl | H | Me | cyclo-PrCH₂CO |
| 5-347 | Cl | H | Cl | H | Me | CF₃CH₂CO |
| 5-348 | Cl | H | Cl | H | Me | CH₃SCH₂CO |
| 5-349 | Cl | H | Cl | H | Me | CH₃SOCH₂CO |
| 5-350 | Cl | H | Cl | H | Me | CH₃SO₂CH₂CO |
| 5-351 | Cl | H | Cl | H | Me | CH₃OCH₂CH₂CO |
| 5-352 | Cl | H | Cl | H | Me | CH₃OCH(Me)CH₂CO |
| 5-353 | Cl | H | Cl | H | Me | EtNHCO |
| 5-354 | Cl | H | Cl | H | Me | tert-BuOC(=O) |
| 5-355 | Br | H | Br | H | Me | H |
| 5-356 | Br | H | Br | H | Me | MeCO |
| 5-357 | Br | H | Br | H | Me | EtCO |
| 5-358 | Br | H | Br | H | Me | n-PrCO |
| 5-359 | Br | H | Br | H | Me | cyclo-PrCO |
| 5-360 | Br | H | Br | H | Me | cyclo-PrCH₂CO |
| 5-361 | Br | H | Br | H | Me | CF₃CH₂CO |
| 5-362 | Br | H | Br | H | Me | CH₃SCH₂CO |
| 5-363 | Br | H | Br | H | Me | CH₃SOCH₂CO |
| 5-364 | Br | H | Br | H | Me | CH₃SO₂CH₂CO |
| 5-365 | Br | H | Br | H | Me | CH₃OCH₂CH₂CO |
| 5-366 | Br | H | Br | H | Me | CH₃OCH(Me)CH₂CO |
| 5-367 | Br | H | Br | H | Me | EtNHCO |
| 5-368 | Br | H | Br | H | Me | tert-BuOC(=O) |
| 5-369 | Cl | Cl | Cl | H | Me | H |
| 5-370 | Cl | Cl | Cl | H | Me | MeCO |
| 5-370-a | Cl | Cl | Cl | H | Me | MeCO |
| 5-371 | Cl | Cl | Cl | H | Me | EtCO |
| 5-371-a | Cl | Cl | Cl | H | Me | EtCO |
| 5-371-b | Cl | Cl | Cl | H | Me | EtCO |
| 5-372 | Cl | Cl | Cl | H | Me | n-PrCO |
| 5-373 | Cl | Cl | Cl | H | Me | cyclo-PrCO |
| 5-373-a | Cl | Cl | Cl | H | Me | cyclo-PrCO |
| 5-374 | Cl | Cl | Cl | H | Me | cyclo-PrCH₂CO |
| 5-374-a | Cl | Cl | Cl | H | Me | cyclo-PrCH₂CO |
| 5-375 | Cl | Cl | Cl | H | Me | CF₃CH₂CO |
| 5-375-a | Cl | Cl | Cl | H | Me | CF₃CH₂CO |
| 5-376 | Cl | Cl | Cl | H | Me | CH₃SCH₂CO |
| 5-377 | Cl | Cl | Cl | H | Me | CH₃SOCH₂CO |
| 5-378 | Cl | Cl | Cl | H | Me | CH₃SO₂CH₂CO |
| 5-379 | Cl | Cl | Cl | H | Me | CH₃OCH₂CH₂CO |
| 5-379-a | Cl | Cl | Cl | H | Me | CH₃OCH₂CH₂CO |
| 5-380 | Cl | Cl | Cl | H | Me | CH₃OCH(Me)CH₂CO |
| 5-381 | Cl | Cl | Cl | H | Me | EtNHCO |
| 5-382 | Cl | Cl | Cl | H | Me | tert-BuOC(=O) |
| 5-383 | CF₃ | H | H | H | Me | H |
| 5-384 | CF₃ | H | H | H | Me | MeCO |
| 5-385 | CF₃ | H | H | H | Me | EtCO |
| 5-386 | CF₃ | H | H | H | Me | n-PrCO |
| 5-387 | CF₃ | H | H | H | Me | cyclo-PrCO |
| 5-388 | CF₃ | H | H | H | Me | cyclo-PrCH₂CO |
| 5-389 | CF₃ | H | H | H | Me | CF₃CH₂CO |
| 5-390 | CF₃ | H | H | H | Me | CH₃SCH₂CO |
| 5-391 | CF₃ | H | H | H | Me | CH₃SOCH₂CO |
| 5-392 | CF₃ | H | H | H | Me | CH₃SO₂CH₂CO |
| 5-393 | CF₃ | H | H | H | Me | CH₃OCH₂CH₂CO |
| 5-394 | CF₃ | H | H | H | Me | CH₃OCH(Me)CH₂CO |
| 5-395 | CF₃ | H | H | H | Me | EtNHCO |
| 5-396 | CF₃ | H | H | H | Me | tert-BuOC(=O) |
| 5-397 | CF₃ | H | CF₃ | H | Me | H |
| 5-398 | CF₃ | H | CF₃ | H | Me | MeCO |
| 5-399 | CF₃ | H | CF₃ | H | Me | MeCO |
| 5-400 | CF₃ | H | CF₃ | H | Me | EtCO |
| 5-401 | CF₃ | H | CF₃ | H | Me | EtCO |
| 5-402 | CF₃ | H | CF₃ | H | Me | EtCO |
| 5-403 | CF₃ | H | CF₃ | H | Me | n-PrCO |
| 5-404 | CF₃ | H | CF₃ | H | Me | cyclo-PrCO |
| 5-405 | CF₃ | H | CF₃ | H | Me | cyclo-PrCO |
| 5-406 | CF₃ | H | CF₃ | H | Me | cyclo-PrCH₂CO |
| 5-407 | CF₃ | H | CF₃ | H | Me | cyclo-PrCH₂CO |
| 5-408 | CF₃ | H | CF₃ | H | Me | CF₃CH₂CO |
| 5-409 | CF₃ | H | CF₃ | H | Me | CF₃CH₂CO |
| 5-410 | CF₃ | H | CF₃ | H | Me | CH₃SCH₂CO |
| 5-411 | CF₃ | H | CF₃ | H | Me | CH₃SOCH₂CO |
| 5-412 | CF₃ | H | CF₃ | H | Me | CH₃SO₂CH₂CO |
| 5-413 | CF₃ | H | CF₃ | H | Me | CH₃OCH₂CH₂CO |
| 5-414 | CF₃ | H | CF₃ | H | Me | CH₃OCH₂CH₂CO |
| 5-415 | CF₃ | H | CF₃ | H | Me | CH₃OCH(Me)CH₂CO |
| 5-416 | CF₃ | H | CF₃ | H | Me | EtNHCO |
| 5-417 | CF₃ | H | CF₃ | H | Me | tert-BuOC(=O) |
| 5-418 | Cl | Cl | CF₃ | H | Me | H |
| 5-419 | Cl | Cl | CF₃ | H | Me | MeCO |
| 5-420 | Cl | Cl | CF₃ | H | Me | EtCO |
| 5-421 | Cl | Cl | CF₃ | H | Me | cyclo-PrCO |
| 5-422 | Cl | Cl | CF₃ | H | Me | CH₃SCH₂CO |
| 5-423 | Cl | Cl | CF₃ | H | Me | CF₃CH₂CO |
| 5-424 | Cl | Cl | CF₃ | H | Me | EtNHCO |
| 5-425 | Cl | Cl | CF₃ | H | Me | tert-BuOC(=O) |
| 5-426 | Cl | H | CF₃ | H | Me | H |
| 5-427 | Cl | H | CF₃ | H | Me | MeCO |

TABLE 5-continued

| Compound No. | X² | X³ | X⁴ | Y³ | R¹ | R⁴ |
|---|---|---|---|---|---|---|
| 5-428 | Cl | H | CF₃ | H | Me | EtCO |
| 5-429 | Cl | H | CF₃ | H | Me | cyclo-PrCO |
| 5-430 | Cl | H | CF₃ | H | Me | CH₃SCH₂CO |
| 5-431 | Cl | H | CF₃ | H | Me | CF₃CH₂CO |
| 5-432 | Cl | H | CF₃ | H | Me | EtNHCO |
| 5-433 | Cl | H | CF₃ | H | Me | tert-BuOC(=O) |
| 5-434 | F | H | CF₃ | H | Me | H |
| 5-435 | F | H | CF₃ | H | Me | MeCO |
| 5-436 | F | H | CF₃ | H | Me | EtCO |
| 5-437 | F | H | CF₃ | H | Me | cyclo-PrCO |
| 5-438 | F | H | CF₃ | H | Me | CH₃SCH₂CO |
| 5-439 | F | H | CF₃ | H | Me | CF₃CH₂CO |
| 5-440 | F | H | CF₃ | H | Me | EtNHCO |
| 5-441 | F | H | CF₃ | H | Me | tert-BuOC(=O) |
| 5-442 | H | F | CF₃ | H | Me | H |
| 5-443 | H | F | CF₃ | H | Me | MeCO |
| 5-444 | H | F | CF₃ | H | Me | EtCO |
| 5-445 | H | F | CF₃ | H | Me | cyclo-PrCO |
| 5-446 | H | F | CF₃ | H | Me | CH₃SCH₂CO |
| 5-447 | H | F | CF₃ | H | Me | CF₃CH₂CO |
| 5-448 | H | F | CF₃ | H | Me | EtNHCO |
| 5-449 | H | F | CF₃ | H | Me | tert-BuOC(=O) |
| 5-450 | OCF₃ | H | H | CF₃ | H | EtCO |
| 5-451 | SCF₃ | H | H | CF₃ | H | EtCO |
| 5-452 | SOCF₃ | H | H | CF₃ | H | EtCO |
| 5-453 | SO₂CF₃ | H | H | CF₃ | H | EtCO |

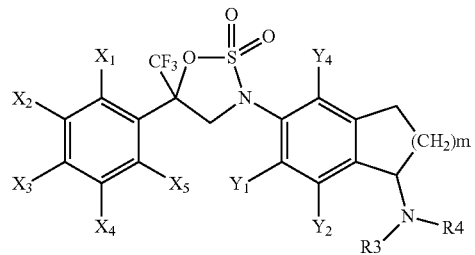

Wherein, $X^1$, $X^5$, $Y^1$, $Y^2$, $Y^4$ and $R^3$ represent hydrogen.

TABLE 6

| Compound No. | X² | X³ | X⁴ | R⁴ | m |
|---|---|---|---|---|---|
| 6-1 | Cl | H | Cl | H | 1 |
| 6-2 | Cl | H | Cl | MeCO | 1 |
| 6-3 | Cl | H | Cl | EtCO | 1 |
| 6-4 | Cl | H | Cl | n-PrCO | 1 |
| 6-5 | Cl | H | Cl | cyclo-PrCO | 1 |
| 6-6 | Cl | H | Cl | cyclo-PrCH₂CO | 1 |
| 6-7 | Cl | H | Cl | CF₃CH₂CO | 1 |
| 6-8 | Cl | H | Cl | CH₃SCH₂CO | 1 |
| 6-9 | Cl | H | Cl | CH₃SOCH₂CO | 1 |
| 6-10 | Cl | H | Cl | CH₃SO₂CH₂CO | 1 |
| 6-11 | Cl | H | Cl | CH₃OCH₂CH₂CO | 1 |
| 6-12 | Cl | H | Cl | CH₃OCH(Me)CH₂CO | 1 |
| 6-13 | Cl | H | Cl | EtNHCO | 1 |
| 6-14 | Cl | H | Cl | tert-BuOC(=O) | 1 |
| 6-15 | Br | H | Br | H | 1 |
| 6-16 | Br | H | Br | MeCO | 1 |
| 6-17 | Br | H | Br | EtCO | 1 |
| 6-18 | Br | H | Br | n-PrCO | 1 |
| 6-19 | Br | H | Br | cyclo-PrCO | 1 |
| 6-20 | Br | H | Br | cyclo-PrCH₂CO | 1 |
| 6-21 | Br | H | Br | CF₃CH₂CO | 1 |
| 6-22 | Br | H | Br | CH₃SCH₂CO | 1 |
| 6-23 | Br | H | Br | CH₃SOCH₂CO | 1 |
| 6-24 | Br | H | Br | CH₃SO₂CH₂CO | 1 |
| 6-25 | Br | H | Br | CH₃OCH₂CH₂CO | 1 |
| 6-26 | Br | H | Br | CH₃OCH(Me)CH₂CO | 1 |
| 6-27 | Br | H | Br | EtNHCO | 1 |
| 6-28 | Br | H | Br | tert-BuOC(=O) | 1 |
| 6-29 | Cl | Cl | Cl | H | 1 |
| 6-30 | Cl | Cl | Cl | MeCO | 1 |
| 6-31 | Cl | Cl | Cl | EtCO | 1 |
| 6-32 | Cl | Cl | Cl | n-PrCO | 1 |
| 6-33 | Cl | Cl | Cl | cyclo-PrCO | 1 |
| 6-34 | Cl | Cl | Cl | cyclo-PrCH₂CO | 1 |
| 6-35 | Cl | Cl | Cl | CF₃CH₂CO | 1 |
| 6-36 | Cl | Cl | Cl | CH₃SCH₂CO | 1 |
| 6-37 | Cl | Cl | Cl | CH₃SOCH₂CO | 1 |
| 6-38 | Cl | Cl | Cl | CH₃SO₂CH₂CO | 1 |
| 6-39 | Cl | Cl | Cl | CH₃OCH₂CH₂CO | 1 |
| 6-40 | Cl | Cl | Cl | CH₃OCH(Me)CH₂CO | 1 |
| 6-41 | Cl | Cl | Cl | EtNHCO | 1 |
| 6-42 | Cl | Cl | Cl | tert-BuOC(=O) | 1 |
| 6-43 | CF₃ | H | H | H | 1 |
| 6-44 | CF₃ | H | H | MeCO | 1 |
| 6-45 | CF₃ | H | H | EtCO | 1 |
| 6-46 | CF₃ | H | H | n-PrCO | 1 |
| 6-47 | CF₃ | H | H | cyclo-PrCO | 1 |
| 6-48 | CF₃ | H | H | cyclo-PrCH₂CO | 1 |
| 6-49 | CF₃ | H | H | CF₃CH₂CO | 1 |
| 6-50 | CF₃ | H | H | CH₃SCH₂CO | 1 |
| 6-51 | CF₃ | H | H | CH₃SOCH₂CO | 1 |
| 6-52 | CF₃ | H | H | CH₃SO₂CH₂CO | 1 |
| 6-53 | CF₃ | H | H | CH₃OCH₂CH₂CO | 1 |
| 6-54 | CF₃ | H | H | CH₃OCH(Me)CH₂CO | 1 |
| 6-55 | CF₃ | H | H | EtNHCO | 1 |
| 6-56 | CF₃ | H | H | tert-BuOC(=O) | 1 |
| 6-57 | CF₃ | H | CF₃ | H | 1 |
| 6-58 | CF₃ | H | CF₃ | MeCO | 1 |
| 6-59 | CF₃ | H | CF₃ | EtCO | 1 |
| 6-60 | CF₃ | H | CF₃ | n-PrCO | 1 |
| 6-61 | CF₃ | H | CF₃ | cyclo-PrCO | 1 |
| 6-62 | CF₃ | H | CF₃ | cyclo-PrCH₂CO | 1 |
| 6-63 | CF₃ | H | CF₃ | CF₃CH₂CO | 1 |
| 6-64 | CF₃ | H | CF₃ | CH₃SCH₂CO | 1 |
| 6-65 | CF₃ | H | CF₃ | CH₃SOCH₂CO | 1 |
| 6-66 | CF₃ | H | CF₃ | CH₃SO₂CH₂CO | 1 |
| 6-67 | CF₃ | H | CF₃ | CH₃OCH₂CH₂CO | 1 |
| 6-68 | CF₃ | H | CF₃ | CH₃OCH(Me)CH₂CO | 1 |
| 6-69 | CF₃ | H | CF₃ | EtNHCO | 1 |
| 6-70 | CF₃ | H | CF₃ | tert-BuOC(=O) | 1 |
| 6-71 | Cl | Cl | CF₃ | H | 1 |
| 6-72 | Cl | Cl | CF₃ | MeCO | 1 |
| 6-73 | Cl | Cl | CF₃ | EtCO | 1 |
| 6-74 | Cl | Cl | CF₃ | cyclo-PrCO | 1 |
| 6-75 | Cl | Cl | CF₃ | CH₃SCH₂CO | 1 |
| 6-76 | Cl | Cl | CF₃ | CF₃CH₂CO | 1 |
| 6-77 | Cl | Cl | CF₃ | EtNHCO | 1 |
| 6-78 | Cl | Cl | CF₃ | tert-BuOC(=O) | 1 |
| 6-79 | Cl | H | CF₃ | H | 1 |
| 6-80 | Cl | H | CF₃ | MeCO | 1 |
| 6-81 | Cl | H | CF₃ | EtCO | 1 |
| 6-82 | Cl | H | CF₃ | cyclo-PrCO | 1 |
| 6-83 | Cl | H | CF₃ | CH₃SCH₂CO | 1 |
| 6-84 | Cl | H | CF₃ | CF₃CH₂CO | 1 |
| 6-85 | Cl | H | CF₃ | EtNHCO | 1 |
| 6-86 | Cl | H | CF₃ | tert-BuOC(=O) | 1 |
| 6-87 | F | H | CF₃ | H | 1 |
| 6-88 | F | H | CF₃ | MeCO | 1 |
| 6-89 | F | H | CF₃ | EtCO | 1 |
| 6-90 | F | H | CF₃ | cyclo-PrCO | 1 |
| 6-91 | F | H | CF₃ | CH₃SCH₂CO | 1 |
| 6-92 | F | H | CF₃ | CF₃CH₂CO | 1 |
| 6-93 | F | H | CF₃ | EtNHCO | 1 |
| 6-94 | F | H | CF₃ | tert-BuOC(=O) | 1 |
| 6-95 | H | F | CF₃ | H | 1 |
| 6-96 | H | F | CF₃ | MeCO | 1 |
| 6-97 | H | F | CF₃ | EtCO | 1 |
| 6-98 | H | F | CF₃ | cyclo-PrCO | 1 |
| 6-99 | H | F | CF₃ | CH₃SCH₂CO | 1 |
| 6-100 | H | F | CF₃ | CF₃CH₂CO | 1 |
| 6-101 | H | F | CF₃ | EtNHCO | 1 |
| 6-102 | H | F | CF₃ | tert-BuOC(=O) | 1 |
| 6-103 | Cl | H | Cl | H | 2 |
| 6-104 | Cl | H | Cl | MeCO | 2 |
| 6-105 | Cl | H | Cl | EtCO | 2 |

TABLE 6-continued

| Compound No. | X² | X³ | X⁴ | R⁴ | m |
|---|---|---|---|---|---|
| 6-106 | Cl | H | Cl | n-PrCO | 2 |
| 6-107 | Cl | H | Cl | cyclo-PrCO | 2 |
| 6-108 | Cl | H | Cl | cyclo-PrCH₂CO | 2 |
| 6-109 | Cl | H | Cl | CF₃CH₂CO | 2 |
| 6-110 | Cl | H | Cl | CH₃SCH₂CO | 2 |
| 6-111 | Cl | H | Cl | CH₃SOCH₂CO | 2 |
| 6-112 | Cl | H | Cl | CH₃SO₂CH₂CO | 2 |
| 6-113 | Cl | H | Cl | CH₃OCH₂CH₂CO | 2 |
| 6-114 | Cl | H | Cl | CH₃OCH(Me)CH₂CO | 2 |
| 6-115 | Cl | H | Cl | EtNHCO | 2 |
| 6-116 | Cl | H | Cl | tert-BuOC(=O) | 2 |
| 6-117 | Br | H | Br | H | 2 |
| 6-118 | Br | H | Br | MeCO | 2 |
| 6-119 | Br | H | Br | EtCO | 2 |
| 6-120 | Br | H | Br | n-PrCO | 2 |
| 6-121 | Br | H | Br | cyclo-PrCO | 2 |
| 6-122 | Br | H | Br | cyclo-PrCH₂CO | 2 |
| 6-123 | Br | H | Br | CF₃CH₂CO | 2 |
| 6-124 | Br | H | Br | CH₃SCH₂CO | 2 |
| 6-125 | Br | H | Br | CH₃SOCH₂CO | 2 |
| 6-126 | Br | H | Br | CH₃SO₂CH₂CO | 2 |
| 6-127 | Br | H | Br | CH₃OCH₂CH₂CO | 2 |
| 6-128 | Br | H | Br | CH₃OCH(Me)CH₂CO | 2 |
| 6-129 | Br | H | Br | EtNHCO | 2 |
| 6-130 | Br | H | Br | tert-BuOC(=O) | 2 |
| 6-131 | Cl | Cl | Cl | H | 2 |
| 6-132 | Cl | Cl | Cl | MeCO | 2 |
| 6-133 | Cl | Cl | Cl | EtCO | 2 |
| 6-134 | Cl | Cl | Cl | n-PrCO | 2 |
| 6-135 | Cl | Cl | Cl | cyclo-PrCO | 2 |
| 6-136 | Cl | Cl | Cl | cyclo-PrCH₂CO | 2 |
| 6-137 | Cl | Cl | Cl | CF₃CH₂CO | 2 |
| 6-138 | Cl | Cl | Cl | CH₃SCH₂CO | 2 |
| 6-139 | Cl | Cl | Cl | CH₃SOCH₂CO | 2 |
| 6-140 | Cl | Cl | Cl | CH₃SO₂CH₂CO | 2 |
| 6-141 | Cl | Cl | Cl | CH₃OCH₂CH₂CO | 2 |
| 6-142 | Cl | Cl | Cl | CH₃OCH(Me)CH₂CO | 2 |
| 6-143 | Cl | Cl | Cl | EtNHCO | 2 |
| 6-144 | Cl | Cl | Cl | tert-BuOC(=O) | 2 |
| 6-145 | CF₃ | H | H | H | 2 |
| 6-146 | CF₃ | H | H | MeCO | 2 |
| 6-147 | CF₃ | H | H | EtCO | 2 |
| 6-148 | CF₃ | H | H | n-PrCO | 2 |
| 6-149 | CF₃ | H | H | cyclo-PrCO | 2 |
| 6-150 | CF₃ | H | H | cyclo-PrCH₂CO | 2 |
| 6-151 | CF₃ | H | H | CF₃CH₂CO | 2 |
| 6-152 | CF₃ | H | H | CH₃SCH₂CO | 2 |
| 6-153 | CF₃ | H | H | CH₃SOCH₂CO | 2 |
| 6-154 | CF₃ | H | H | CH₃SO₂CH₂CO | 2 |
| 6-155 | CF₃ | H | H | CH₃OCH₂CH₂CO | 2 |
| 6-156 | CF₃ | H | H | CH₃OCH(Me)CH₂CO | 2 |
| 6-157 | CF₃ | H | H | EtNHCO | 2 |
| 6-158 | CF₃ | H | H | tert-BuOC(=O) | 2 |
| 6-159 | CF₃ | H | CF₃ | H | 2 |
| 6-160 | CF₃ | H | CF₃ | MeCO | 2 |
| 6-161 | CF₃ | H | CF₃ | EtCO | 2 |
| 6-162 | CF₃ | H | CF₃ | n-PrCO | 2 |
| 6-163 | CF₃ | H | CF₃ | cyclo-PrCO | 2 |
| 6-164 | CF₃ | H | CF₃ | cyclo-PrCH₂CO | 2 |
| 6-165 | CF₃ | H | CF₃ | CF₃CH₂CO | 2 |
| 6-166 | CF₃ | H | CF₃ | CH₃SCH₂CO | 2 |
| 6-167 | CF₃ | H | CF₃ | CH₃SOCH₂CO | 2 |
| 6-168 | CF₃ | H | CF₃ | CH₃SO₂CH₂CO | 2 |
| 6-169 | CF₃ | H | CF₃ | CH₃OCH₂CH₂CO | 2 |
| 6-170 | CF₃ | H | CF₃ | CH₃OCH(Me)CH₂CO | 2 |
| 6-171 | CF₃ | H | CF₃ | EtNHCO | 2 |
| 6-172 | CF₃ | H | CF₃ | tert-BuOC(=O) | 2 |
| 6-173 | Cl | Cl | CF₃ | H | 2 |
| 6-174 | Cl | Cl | CF₃ | MeCO | 2 |
| 6-175 | Cl | Cl | CF₃ | EtCO | 2 |
| 6-176 | Cl | Cl | CF₃ | cyclo-PrCO | 2 |
| 6-177 | Cl | Cl | CF₃ | CH₃SCH₂CO | 2 |
| 6-178 | Cl | Cl | CF₃ | CF₃CH₂CO | 2 |
| 6-179 | Cl | Cl | CF₃ | EtNHCO | 2 |
| 6-180 | Cl | Cl | CF₃ | tert-BuOC(=O) | 2 |
| 6-181 | Cl | H | CF₃ | H | 2 |
| 6-182 | Cl | H | CF₃ | MeCO | 2 |
| 6-183 | Cl | H | CF₃ | EtCO | 2 |
| 6-184 | Cl | H | CF₃ | cyclo-PrCO | 2 |
| 6-185 | Cl | H | CF₃ | CH₃SCH₂CO | 2 |
| 6-186 | Cl | H | CF₃ | CF₃CH₂CO | 2 |
| 6-187 | Cl | H | CF₃ | EtNHCO | 2 |
| 6-188 | Cl | H | CF₃ | tert-BuOC(=O) | 2 |
| 6-189 | F | H | CF₃ | H | 2 |
| 6-190 | F | H | CF₃ | MeCO | 2 |
| 6-191 | F | H | CF₃ | EtCO | 2 |
| 6-192 | F | H | CF₃ | cyclo-PrCO | 2 |
| 6-193 | F | H | CF₃ | CH₃SCH₂CO | 2 |
| 6-194 | F | H | CF₃ | CF₃CH₂CO | 2 |
| 6-195 | F | H | CF₃ | EtNHCO | 2 |
| 6-196 | F | H | CF₃ | tert-BuOC(=O) | 2 |
| 6-197 | H | F | CF₃ | H | 2 |
| 6-198 | H | F | CF₃ | MeCO | 2 |
| 6-199 | H | F | CF₃ | EtCO | 2 |
| 6-200 | H | F | CF₃ | cyclo-PrCO | 2 |
| 6-201 | H | F | CF₃ | CH₃SCH₂CO | 2 |
| 6-202 | H | F | CF₃ | CF₃CH₂CO | 2 |
| 6-203 | H | F | CF₃ | EtNHCO | 2 |
| 6-204 | H | F | CF₃ | tert-BuOC(=O) | 2 |
| 6-205 | OCF₃ | H | H | EtCO | 1 |
| 6-206 | SCF₃ | H | H | EtCO | 1 |
| 6-207 | SOCF₃ | H | H | EtCO | 1 |
| 6-208 | SO₂CF₃ | H | H | EtCO | 1 |

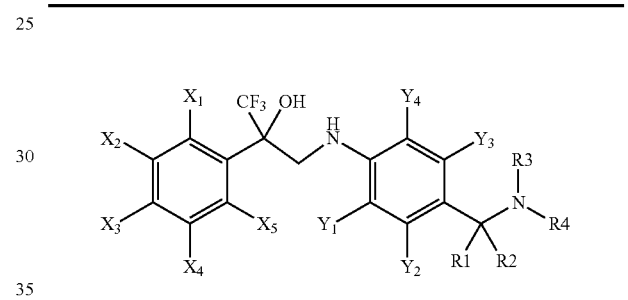

Wherein, $X^1, X^5, Y^1, Y^2, Y^4, R^2$ and $R^3$ represent hydrogen.

TABLE 7

| Compound No. | X² | X³ | X⁴ | Y³ | R¹ | R⁴ |
|---|---|---|---|---|---|---|
| 7-1 | Cl | H | Cl | CF₃ | H | H |
| 7-2 | Cl | H | Cl | CF₃ | H | MeCO |
| 7-3 | Cl | H | Cl | CF₃ | H | EtCO |
| 7-4 | Cl | H | Cl | CF₃ | H | n-PrCO |
| 7-5 | Cl | H | Cl | CF₃ | H | cyclo-PrCO |
| 7-6 | Cl | H | Cl | CF₃ | H | cyclo-PrCH₂CO |
| 7-7 | Cl | H | Cl | CF₃ | H | CF₃CH₂CO |
| 7-8 | Cl | H | Cl | CF₃ | H | CH₃SCH₂CO |
| 7-9 | Cl | H | Cl | CF₃ | H | CH₃SOCH₂CO |
| 7-10 | Cl | H | Cl | CF₃ | H | CH₃SO₂CH₂CO |
| 7-11 | Cl | H | Cl | CF₃ | H | CH₃OCH₂CH₂CO |
| 7-12 | Cl | H | Cl | CF₃ | H | CH₃OCH(Me)CH₂CO |
| 7-13 | Cl | H | Cl | CF₃ | H | EtNHCO |
| 7-14 | Cl | H | Cl | CF₃ | H | tert-BuOC(=O) |
| 7-15 | Cl | Cl | Cl | CF₃ | H | H |
| 7-16 | Cl | Cl | Cl | CF₃ | H | MeCO |
| 7-17 | Cl | Cl | Cl | CF₃ | H | EtCO |
| 7-18 | Cl | Cl | Cl | CF₃ | H | n-PrCO |
| 7-19 | Cl | Cl | Cl | CF₃ | H | cyclo-PrCO |
| 7-20 | Cl | Cl | Cl | CF₃ | H | cyclo-PrCH₂CO |
| 7-21 | Cl | Cl | Cl | CF₃ | H | CF₃CH₂CO |
| 7-22 | Cl | Cl | Cl | CF₃ | H | CH₃SCH₂CO |
| 7-23 | Cl | Cl | Cl | CF₃ | H | CH₃SOCH₂CO |
| 7-24 | Cl | Cl | Cl | CF₃ | H | CH₃SO₂CH₂CO |
| 7-25 | Cl | Cl | Cl | CF₃ | H | CH₃OCH₂CH₂CO |
| 7-26 | Cl | Cl | Cl | CF₃ | H | CH₃OCH(Me)CH₂CO |
| 7-27 | Cl | Cl | Cl | CF₃ | H | EtNHCO |
| 7-28 | Cl | Cl | Cl | CF₃ | H | tert-BuOC(=O) |
| 7-29 | Cl | Cl | Cl | Cl | H | H |
| 7-30 | Cl | Cl | Cl | Cl | H | MeCO |
| 7-31 | Cl | Cl | Cl | Cl | H | EtCO |

TABLE 7-continued

| Compound No. | $X^2$ | $X^3$ | $X^4$ | $Y^3$ | $R^1$ | $R^4$ |
|---|---|---|---|---|---|---|
| 7-32 | Cl | Cl | Cl | Cl | H | n-PrCO |
| 7-33 | Cl | Cl | Cl | Cl | H | cyclo-PrCO |
| 7-34 | Cl | Cl | Cl | Cl | H | cyclo-PrCH$_2$CO |
| 7-35 | Cl | Cl | Cl | Cl | H | CF$_3$CH$_2$CO |
| 7-36 | Cl | Cl | Cl | Cl | H | CH$_3$SCH$_2$CO |
| 7-37 | Cl | Cl | Cl | Cl | H | CH$_3$SOCH$_2$CO |
| 7-38 | Cl | Cl | Cl | Cl | H | CH$_3$SO$_2$CH$_2$CO |
| 7-39 | Cl | Cl | Cl | Cl | H | CH$_3$OCH$_2$CH$_2$CO |
| 7-40 | Cl | Cl | Cl | Cl | H | CH$_3$OCH(Me)CH$_2$CO |
| 7-41 | Cl | Cl | Cl | Cl | H | EtNHCO |
| 7-42 | Cl | Cl | Cl | Cl | H | tert-BuOC(=O) |
| 7-43 | Cl | Cl | Cl | Me | H | H |
| 7-44 | Cl | Cl | Cl | Me | H | MeCO |
| 7-45 | Cl | Cl | Cl | Me | H | EtCO |
| 7-46 | Cl | Cl | Cl | Me | H | n-PrCO |
| 7-47 | Cl | Cl | Cl | Me | H | cyclo-PrCO |
| 7-48 | Cl | Cl | Cl | Me | H | cyclo-PrCH$_2$CO |
| 7-49 | Cl | Cl | Cl | Me | H | CF$_3$CH$_2$CO |
| 7-50 | Cl | Cl | Cl | Me | H | CH$_3$SCH$_2$CO |
| 7-51 | Cl | Cl | Cl | Me | H | CH$_3$SOCH$_2$CO |
| 7-52 | Cl | Cl | Cl | Me | H | CH$_3$SO$_2$CH$_2$CO |
| 7-53 | Cl | Cl | Cl | Me | H | CH$_3$OCH$_2$CH$_2$CO |
| 7-54 | Cl | Cl | Cl | Me | H | CH$_3$OCH(Me)CH$_2$CO |
| 7-55 | Cl | Cl | Cl | Me | H | EtNHCO |
| 7-56 | Cl | Cl | Cl | Me | H | tert-BuOC(=O) |
| 7-57 | Cl | Cl | Cl | H | H | H |
| 7-58 | Cl | Cl | Cl | H | H | MeCO |
| 7-59 | Cl | Cl | Cl | H | H | EtCO |
| 7-60 | Cl | Cl | Cl | H | H | n-PrCO |
| 7-61 | Cl | Cl | Cl | H | H | cyclo-PrCO |
| 7-62 | Cl | Cl | Cl | H | H | cyclo-PrCH$_2$CO |
| 7-63 | Cl | Cl | Cl | H | H | CF$_3$CH$_2$CO |
| 7-64 | Cl | Cl | Cl | H | H | CH$_3$SCH$_2$CO |
| 7-65 | Cl | Cl | Cl | H | H | CH$_3$SOCH$_2$CO |
| 7-66 | Cl | Cl | Cl | H | H | CH$_3$SO$_2$CH$_2$CO |
| 7-67 | Cl | Cl | Cl | H | H | CH$_3$OCH$_2$CH$_2$CO |
| 7-68 | Cl | Cl | Cl | H | H | CH$_3$OCH(Me)CH$_2$CO |
| 7-69 | Cl | Cl | Cl | H | H | EtNHCO |
| 7-70 | Cl | Cl | Cl | H | H | tert-BuOC(=O) |
| 7-71 | CF$_3$ | H | H | CF$_3$ | H | H |
| 7-72 | CF$_3$ | H | H | CF$_3$ | H | MeCO |
| 7-73 | CF$_3$ | H | H | CF$_3$ | H | EtCO |
| 7-74 | CF$_3$ | H | H | CF$_3$ | H | n-PrCO |
| 7-75 | CF$_3$ | H | H | CF$_3$ | H | cyclo-PrCO |
| 7-76 | CF$_3$ | H | H | CF$_3$ | H | cyclo-PrCH$_2$CO |
| 7-77 | CF$_3$ | H | H | CF$_3$ | H | CF$_3$CH$_2$CO |
| 7-78 | CF$_3$ | H | H | CF$_3$ | H | CH$_3$SCH$_2$CO |
| 7-79 | CF$_3$ | H | H | CF$_3$ | H | CH$_3$SOCH$_2$CO |
| 7-80 | CF$_3$ | H | H | CF$_3$ | H | CH$_3$SO$_2$CH$_2$CO |
| 7-81 | CF$_3$ | H | H | CF$_3$ | H | CH$_3$OCH$_2$CH$_2$CO |
| 7-82 | CF$_3$ | H | H | CF$_3$ | H | CH$_3$OCH(Me)CH$_2$CO |
| 7-83 | CF$_3$ | H | H | CF$_3$ | H | EtNHCO |
| 7-84 | CF$_3$ | H | H | CF$_3$ | H | tert-BuOC(=O) |
| 7-85 | CF$_3$ | H | H | Cl | H | H |
| 7-86 | CF$_3$ | H | H | Cl | H | MeCO |
| 7-87 | CF$_3$ | H | H | Cl | H | EtCO |
| 7-88 | CF$_3$ | H | H | Cl | H | n-PrCO |
| 7-89 | CF$_3$ | H | H | Cl | H | cyclo-PrCO |
| 7-90 | CF$_3$ | H | H | Cl | H | cyclo-PrCH$_2$CO |
| 7-91 | CF$_3$ | H | H | Cl | H | CF$_3$CH$_2$CO |
| 7-92 | CF$_3$ | H | H | Cl | H | CH$_3$SCH$_2$CO |
| 7-93 | CF$_3$ | H | H | Cl | H | CH$_3$SOCH$_2$CO |
| 7-94 | CF$_3$ | H | H | Cl | H | CH$_3$SO$_2$CH$_2$CO |
| 7-95 | CF$_3$ | H | H | Cl | H | CH$_3$OCH$_2$CH$_2$CO |
| 7-96 | CF$_3$ | H | H | Cl | H | CH$_3$OCH(Me)CH$_2$CO |
| 7-97 | CF$_3$ | H | H | Cl | H | EtNHCO |
| 7-98 | CF$_3$ | H | H | Cl | H | tert-BuOC(=O) |
| 7-99 | CF$_3$ | H | H | Me | H | H |
| 7-100 | CF$_3$ | H | H | Me | H | MeCO |
| 7-101 | CF$_3$ | H | H | Me | H | EtCO |
| 7-102 | CF$_3$ | H | H | Me | H | n-PrCO |
| 7-103 | CF$_3$ | H | H | Me | H | cyclo-PrCO |
| 7-104 | CF$_3$ | H | H | Me | H | cyclo-PrCH$_2$CO |
| 7-105 | CF$_3$ | H | H | Me | H | CF$_3$CH$_2$CO |
| 7-106 | CF$_3$ | H | H | Me | H | CH$_3$SCH$_2$CO |
| 7-107 | CF$_3$ | H | H | Me | H | CH$_3$SOCH$_2$CO |
| 7-108 | CF$_3$ | H | H | Me | H | CH$_3$SO$_2$CH$_2$CO |
| 7-109 | CF$_3$ | H | H | Me | H | CH$_3$OCH$_2$CH$_2$CO |
| 7-110 | CF$_3$ | H | H | Me | H | CH$_3$OCH(Me)CH$_2$CO |
| 7-111 | CF$_3$ | H | H | Me | H | EtNHCO |
| 7-112 | CF$_3$ | H | H | Me | H | tert-BuOC(=O) |
| 7-113 | CF$_3$ | H | H | H | H | H |
| 7-114 | CF$_3$ | H | H | H | H | MeCO |
| 7-115 | CF$_3$ | H | H | H | H | EtCO |
| 7-116 | CF$_3$ | H | H | H | H | n-PrCO |
| 7-117 | CF$_3$ | H | H | H | H | cyclo-PrCO |
| 7-118 | CF$_3$ | H | H | H | H | cyclo-PrCH$_2$CO |
| 7-119 | CF$_3$ | H | H | H | H | CF$_3$CH$_2$CO |
| 7-120 | CF$_3$ | H | H | H | H | CH$_3$SCH$_2$CO |
| 7-121 | CF$_3$ | H | H | H | H | CH$_3$SOCH$_2$CO |
| 7-122 | CF$_3$ | H | H | H | H | CH$_3$SO$_2$CH$_2$CO |
| 7-123 | CF$_3$ | H | H | H | H | CH$_3$OCH$_2$CH$_2$CO |
| 7-124 | CF$_3$ | H | H | H | H | CH$_3$OCH(Me)CH$_2$CO |
| 7-125 | CF$_3$ | H | H | H | H | EtNHCO |
| 7-126 | CF$_3$ | H | H | H | H | tert-BuOC(=O) |
| 7-127 | CF$_3$ | H | CF$_3$ | CF$_3$ | H | H |
| 7-128 | CF$_3$ | H | CF$_3$ | CF$_3$ | H | MeCO |
| 7-129 | CF$_3$ | H | CF$_3$ | CF$_3$ | H | EtCO |
| 7-130 | CF$_3$ | H | CF$_3$ | CF$_3$ | H | n-PrCO |
| 7-131 | CF$_3$ | H | CF$_3$ | CF$_3$ | H | cyclo-PrCO |
| 7-132 | CF$_3$ | H | CF$_3$ | CF$_3$ | H | cyclo-PrCH$_2$CO |
| 7-133 | CF$_3$ | H | CF$_3$ | CF$_3$ | H | CF$_3$CH$_2$CO |
| 7-134 | CF$_3$ | H | CF$_3$ | CF$_3$ | H | CH$_3$SCH$_2$CO |
| 7-135 | CF$_3$ | H | CF$_3$ | CF$_3$ | H | CH$_3$SOCH$_2$CO |
| 7-136 | CF$_3$ | H | CF$_3$ | CF$_3$ | H | CH$_3$SO$_2$CH$_2$CO |
| 7-137 | CF$_3$ | H | CF$_3$ | CF$_3$ | H | CH$_3$OCH$_2$CH$_2$CO |
| 7-138 | CF$_3$ | H | CF$_3$ | CF$_3$ | H | CH$_3$OCH(Me)CH$_2$CO |
| 7-139 | CF$_3$ | H | CF$_3$ | CF$_3$ | H | EtNHCO |
| 7-140 | CF$_3$ | H | CF$_3$ | CF$_3$ | H | tert-BuOC(=O) |
| 7-141 | CF$_3$ | H | CF$_3$ | Cl | H | H |
| 7-142 | CF$_3$ | H | CF$_3$ | Cl | H | MeCO |
| 7-143 | CF$_3$ | H | CF$_3$ | Cl | H | EtCO |
| 7-144 | CF$_3$ | H | CF$_3$ | Cl | H | n-PrCO |
| 7-145 | CF$_3$ | H | CF$_3$ | Cl | H | cyclo-PrCO |
| 7-146 | CF$_3$ | H | CF$_3$ | Cl | H | cyclo-PrCH$_2$CO |
| 7-147 | CF$_3$ | H | CF$_3$ | Cl | H | CF$_3$CH$_2$CO |
| 7-148 | CF$_3$ | H | CF$_3$ | Cl | H | CH$_3$SCH$_2$CO |
| 7-149 | CF$_3$ | H | CF$_3$ | Cl | H | CH$_3$SOCH$_2$CO |
| 7-150 | CF$_3$ | H | CF$_3$ | Cl | H | CH$_3$SO$_2$CH$_2$CO |
| 7-151 | CF$_3$ | H | CF$_3$ | Cl | H | CH$_3$OCH$_2$CH$_2$CO |
| 7-152 | CF$_3$ | H | CF$_3$ | Cl | H | CH$_3$OCH(Me)CH$_2$CO |
| 7-153 | CF$_3$ | H | CF$_3$ | Cl | H | EtNHCO |
| 7-154 | CF$_3$ | H | CF$_3$ | Cl | H | tert-BuOC(=O) |
| 7-155 | CF$_3$ | H | CF$_3$ | Me | H | H |
| 7-156 | CF$_3$ | H | CF$_3$ | Me | H | MeCO |
| 7-157 | CF$_3$ | H | CF$_3$ | Me | H | EtCO |
| 7-158 | CF$_3$ | H | CF$_3$ | Me | H | n-PrCO |
| 7-159 | CF$_3$ | H | CF$_3$ | Me | H | cyclo-PrCO |
| 7-160 | CF$_3$ | H | CF$_3$ | Me | H | cyclo-PrCH$_2$CO |
| 7-161 | CF$_3$ | H | CF$_3$ | Me | H | CF$_3$CH$_2$CO |
| 7-162 | CF$_3$ | H | CF$_3$ | Me | H | CH$_3$SCH$_2$CO |
| 7-163 | CF$_3$ | H | CF$_3$ | Me | H | CH$_3$SOCH$_2$CO |
| 7-164 | CF$_3$ | H | CF$_3$ | Me | H | CH$_3$SO$_2$CH$_2$CO |
| 7-165 | CF$_3$ | H | CF$_3$ | Me | H | CH$_3$OCH$_2$CH$_2$CO |
| 7-166 | CF$_3$ | H | CF$_3$ | Me | H | CH$_3$OCH(Me)CH$_2$CO |
| 7-167 | CF$_3$ | H | CF$_3$ | Me | H | EtNHCO |
| 7-168 | CF$_3$ | H | CF$_3$ | Me | H | tert-BuOC(=O) |
| 7-169 | CF$_3$ | H | CF$_3$ | H | H | H |
| 7-170 | CF$_3$ | H | CF$_3$ | H | H | MeCO |
| 7-171 | CF$_3$ | H | CF$_3$ | H | H | EtCO |
| 7-172 | CF$_3$ | H | CF$_3$ | H | H | n-PrCO |
| 7-173 | CF$_3$ | H | CF$_3$ | H | H | cyclo-PrCO |
| 7-174 | CF$_3$ | H | CF$_3$ | H | H | cyclo-PrCH$_2$CO |
| 7-175 | CF$_3$ | H | CF$_3$ | H | H | CF$_3$CH$_2$CO |
| 7-176 | CF$_3$ | H | CF$_3$ | H | H | CH$_3$SCH$_2$CO |
| 7-177 | CF$_3$ | H | CF$_3$ | H | H | CH$_3$SOCH$_2$CO |
| 7-178 | CF$_3$ | H | CF$_3$ | H | H | CH$_3$SO$_2$CH$_2$CO |
| 7-179 | CF$_3$ | H | CF$_3$ | H | H | CH$_3$OCH$_2$CH$_2$CO |
| 7-180 | CF$_3$ | H | CF$_3$ | H | H | CH$_3$OCH(Me)CH$_2$CO |
| 7-181 | CF$_3$ | H | CF$_3$ | H | H | EtNHCO |
| 7-182 | CF$_3$ | H | CF$_3$ | H | H | tert-BuOC(=O) |
| 7-183 | Cl | Cl | CF$_3$ | CF$_3$ | H | H |
| 7-184 | Cl | Cl | CF$_3$ | CF$_3$ | H | MeCO |
| 7-185 | Cl | Cl | CF$_3$ | CF$_3$ | H | EtCO |
| 7-186 | Cl | Cl | CF$_3$ | CF$_3$ | H | cyclo-PrCO |
| 7-187 | Cl | Cl | CF$_3$ | CF$_3$ | H | CH$_3$SCH$_2$CO |

TABLE 7-continued

| Compound No. | X² | X³ | X⁴ | Y³ | R¹ | R⁴ |
|---|---|---|---|---|---|---|
| 7-188 | Cl | Cl | CF₃ | CF₃ | H | CF₃CH₂CO |
| 7-189 | Cl | Cl | CF₃ | CF₃ | H | EtNHCO |
| 7-190 | Cl | Cl | CF₃ | CF₃ | H | tert-BuOC(=O) |
| 7-191 | Cl | H | CF₃ | CF₃ | H | H |
| 7-192 | Cl | H | CF₃ | CF₃ | H | MeCO |
| 7-193 | Cl | H | CF₃ | CF₃ | H | EtCO |
| 7-194 | Cl | H | CF₃ | CF₃ | H | cyclo-PrCO |
| 7-195 | Cl | H | CF₃ | CF₃ | H | CH₃SCH₂CO |
| 7-196 | Cl | H | CF₃ | CF₃ | H | CF₃CH₂CO |
| 7-197 | Cl | H | CF₃ | CF₃ | H | EtNHCO |
| 7-198 | Cl | H | CF₃ | CF₃ | H | tert-BuOC(=O) |
| 7-199 | F | H | CF₃ | CF₃ | H | H |
| 7-200 | F | H | CF₃ | CF₃ | H | MeCO |
| 7-201 | F | H | CF₃ | CF₃ | H | EtCO |
| 7-202 | F | H | CF₃ | CF₃ | H | cyclo-PrCO |
| 7-203 | F | H | CF₃ | CF₃ | H | CH₃SCH₂CO |
| 7-204 | F | H | CF₃ | CF₃ | H | CF₃CH₂CO |
| 7-205 | F | H | CF₃ | CF₃ | H | EtNHCO |
| 7-206 | F | H | CF₃ | CF₃ | H | tert-BuOC(=O) |
| 7-207 | H | F | CF₃ | CF₃ | H | H |
| 7-208 | H | F | CF₃ | CF₃ | H | MeCO |
| 7-209 | H | F | CF₃ | CF₃ | H | EtCO |
| 7-210 | H | F | CF₃ | CF₃ | H | cyclo-PrCO |
| 7-211 | H | F | CF₃ | CF₃ | H | CH₃SCH₂CO |
| 7-212 | H | F | CF₃ | CF₃ | H | CF₃CH₂CO |
| 7-213 | H | F | CF₃ | CF₃ | H | EtNHCO |
| 7-214 | H | F | CF₃ | CF₃ | H | tert-BuOC(=O) |
| 7-215 | Cl | H | Cl | Br | H | H |
| 7-216 | Cl | H | Cl | Br | H | MeCO |
| 7-217 | Cl | H | Cl | Br | H | EtCO |
| 7-218 | Cl | H | Cl | Br | H | n-PrCO |
| 7-219 | Cl | H | Cl | Br | H | cyclo-PrCO |
| 7-220 | Cl | H | Cl | Br | H | cyclo-PrCH₂CO |
| 7-221 | Cl | H | Cl | Br | H | CF₃CH₂CO |
| 7-222 | Cl | H | Cl | Br | H | CH₃SCH₂CO |
| 7-223 | Cl | H | Cl | Br | H | CH₃SOCH₂CO |
| 7-224 | Cl | H | Cl | Br | H | CH₃SO₂CH₂CO |
| 7-225 | Cl | H | Cl | Br | H | CH₃OCH₂CH₂CO |
| 7-226 | Cl | H | Cl | Br | H | CH₃OCH(Me)CH₂CO |
| 7-227 | Cl | H | Cl | Br | H | EtNHCO |
| 7-228 | Cl | H | Cl | Br | H | tert-BuOC(=O) |
| 7-229 | Cl | Cl | Cl | Br | H | H |
| 7-230 | Cl | Cl | Cl | Br | H | MeCO |
| 7-231 | Cl | Cl | Cl | Br | H | EtCO |
| 7-232 | Cl | Cl | Cl | Br | H | n-PrCO |
| 7-233 | Cl | Cl | Cl | Br | H | cyclo-PrCO |
| 7-234 | Cl | Cl | Cl | Br | H | cyclo-PrCH₂CO |
| 7-235 | Cl | Cl | Cl | Br | H | CF₃CH₂CO |
| 7-236 | Cl | Cl | Cl | Br | H | CH₃SCH₂CO |
| 7-237 | Cl | Cl | Cl | Br | H | CH₃SOCH₂CO |
| 7-238 | Cl | Cl | Cl | Br | H | CH₃SO₂CH₂CO |
| 7-239 | Cl | Cl | Cl | Br | H | CH₃OCH₂CH₂CO |
| 7-240 | Cl | Cl | Cl | Br | H | CH₃OCH(Me)CH₂CO |
| 7-241 | Cl | Cl | Cl | Br | H | EtNHCO |
| 7-242 | Cl | Cl | Cl | Br | H | tert-BuOC(=O) |
| 7-243 | CF₃ | H | H | Br | H | H |
| 7-244 | CF₃ | H | H | Br | H | MeCO |
| 7-245 | CF₃ | H | H | Br | H | EtCO |
| 7-246 | CF₃ | H | H | Br | H | n-PrCO |
| 7-247 | CF₃ | H | H | Br | H | cyclo-PrCO |
| 7-248 | CF₃ | H | H | Br | H | cyclo-PrCH₂CO |
| 7-249 | CF₃ | H | H | Br | H | CF₃CH₂CO |
| 7-250 | CF₃ | H | H | Br | H | CH₃SCH₂CO |
| 7-251 | CF₃ | H | H | Br | H | CH₃SOCH₂CO |
| 7-252 | CF₃ | H | H | Br | H | CH₃SO₂CH₂CO |
| 7-253 | CF₃ | H | H | Br | H | CH₃OCH₂CH₂CO |
| 7-254 | CF₃ | H | H | Br | H | CH₃OCH(Me)CH₂CO |
| 7-255 | CF₃ | H | H | Br | H | EtNHCO |
| 7-256 | CF₃ | H | H | Br | H | tert-BuOC(=O) |
| 7-257 | CF₃ | H | CF₃ | Br | H | H |
| 7-258 | CF₃ | H | CF₃ | Br | H | MeCO |
| 7-259 | CF₃ | H | CF₃ | Br | H | EtCO |
| 7-260 | CF₃ | H | CF₃ | Br | H | n-PrCO |
| 7-261 | CF₃ | H | CF₃ | Br | H | cyclo-PrCO |
| 7-262 | CF₃ | H | CF₃ | Br | H | cyclo-PrCH₂CO |
| 7-263 | CF₃ | H | CF₃ | Br | H | CF₃CH₂CO |
| 7-264 | CF₃ | H | CF₃ | Br | H | CH₃SCH₂CO |
| 7-265 | CF₃ | H | CF₃ | Br | H | CH₃SOCH₂CO |
| 7-266 | CF₃ | H | CF₃ | Br | H | CH₃SO₂CH₂CO |
| 7-267 | CF₃ | H | CF₃ | Br | H | CH₃OCH₂CH₂CO |
| 7-268 | CF₃ | H | CF₃ | Br | H | CH₃OCH(Me)CH₂CO |
| 7-269 | CF₃ | H | CF₃ | Br | H | EtNHCO |
| 7-270 | CF₃ | H | CF₃ | Br | H | tert-BuOC(=O) |
| 7-271 | Br | H | Br | CF₃ | H | H |
| 7-272 | Br | H | Br | CF₃ | H | MeCO |
| 7-273 | Br | H | Br | CF₃ | H | EtCO |
| 7-274 | Br | H | Br | CF₃ | H | n-PrCO |
| 7-275 | Br | H | Br | CF₃ | H | cyclo-PrCO |
| 7-276 | Br | H | Br | CF₃ | H | cyclo-PrCH₂CO |
| 7-277 | Br | H | Br | CF₃ | H | CF₃CH₂CO |
| 7-278 | Br | H | Br | CF₃ | H | CH₃SCH₂CO |
| 7-279 | Br | H | Br | CF₃ | H | CH₃SOCH₂CO |
| 7-280 | Br | H | Br | CF₃ | H | CH₃SO₂CH₂CO |
| 7-281 | Br | H | Br | CF₃ | H | CH₃OCH₂CH₂CO |
| 7-282 | Br | H | Br | CF₃ | H | CH₃OCH(Me)CH₂CO |
| 7-283 | Br | H | Br | CF₃ | H | EtNHCO |
| 7-284 | Br | H | Br | CF₃ | H | tert-BuOC(=O) |
| 7-285 | Br | H | Br | Cl | H | H |
| 7-286 | Br | H | Br | Cl | H | MeCO |
| 7-287 | Br | H | Br | Cl | H | EtCO |
| 7-288 | Br | H | Br | Cl | H | n-PrCO |
| 7-289 | Br | H | Br | Cl | H | cyclo-PrCO |
| 7-290 | Br | H | Br | Cl | H | cyclo-PrCH₂CO |
| 7-291 | Br | H | Br | Cl | H | CF₃CH₂CO |
| 7-292 | Br | H | Br | Cl | H | CH₃SCH₂CO |
| 7-293 | Br | H | Br | Cl | H | CH₃SOCH₂CO |
| 7-294 | Br | H | Br | Cl | H | CH₃SO₂CH₂CO |
| 7-295 | Br | H | Br | Cl | H | CH₃OCH₂CH₂CO |
| 7-296 | Br | H | Br | Cl | H | CH₃OCH(Me)CH₂CO |
| 7-297 | Br | H | Br | Cl | H | EtNHCO |
| 7-298 | Br | H | Br | Cl | H | tert-BuOC(=O) |
| 7-299 | Br | H | Br | Br | H | H |
| 7-300 | Br | H | Br | Br | H | MeCO |
| 7-301 | Br | H | Br | Br | H | EtCO |
| 7-302 | Br | H | Br | Br | H | n-PrCO |
| 7-303 | Br | H | Br | Br | H | cyclo-PrCO |
| 7-304 | Br | H | Br | Br | H | cyclo-PrCH₂CO |
| 7-305 | Br | H | Br | Br | H | CF₃CH₂CO |
| 7-306 | Br | H | Br | Br | H | CH₃SCH₂CO |
| 7-307 | Br | H | Br | Br | H | CH₃SOCH₂CO |
| 7-308 | Br | H | Br | Br | H | CH₃SO₂CH₂CO |
| 7-309 | Br | H | Br | Br | H | CH₃OCH₂CH₂CO |
| 7-310 | Br | H | Br | Br | H | CH₃OCH(Me)CH₂CO |
| 7-311 | Br | H | Br | Br | H | EtNHCO |
| 7-312 | Br | H | Br | Br | H | tert-BuOC(=O) |
| 7-313 | Br | H | Br | Me | H | H |
| 7-314 | Br | H | Br | Me | H | MeCO |
| 7-315 | Br | H | Br | Me | H | EtCO |
| 7-316 | Br | H | Br | Me | H | n-PrCO |
| 7-317 | Br | H | Br | Me | H | cyclo-PrCO |
| 7-318 | Br | H | Br | Me | H | cyclo-PrCH₂CO |
| 7-319 | Br | H | Br | Me | H | CF₃CH₂CO |
| 7-320 | Br | H | Br | Me | H | CH₃SCH₂CO |
| 7-321 | Br | H | Br | Me | H | CH₃SOCH₂CO |
| 7-322 | Br | H | Br | Me | H | CH₃SO₂CH₂CO |
| 7-323 | Br | H | Br | Me | H | CH₃OCH₂CH₂CO |
| 7-324 | Br | H | Br | Me | H | CH₃OCH(Me)CH₂CO |
| 7-325 | Br | H | Br | Me | H | EtNHCO |
| 7-326 | Br | H | Br | Me | H | tert-BuOC(=O) |
| 7-327 | Br | H | Br | H | H | H |
| 7-328 | Br | H | Br | H | H | MeCO |
| 7-329 | Br | H | Br | H | H | EtCO |
| 7-330 | Br | H | Br | H | H | n-PrCO |
| 7-331 | Br | H | Br | H | H | cyclo-PrCO |
| 7-332 | Br | H | Br | H | H | cyclo-PrCH₂CO |
| 7-333 | Br | H | Br | H | H | CF₃CH₂CO |
| 7-334 | Br | H | Br | H | H | CH₃SCH₂CO |
| 7-335 | Br | H | Br | H | H | CH₃SOCH₂CO |
| 7-336 | Br | H | Br | H | H | CH₃SO₂CH₂CO |
| 7-337 | Br | H | Br | H | H | CH₃OCH₂CH₂CO |
| 7-338 | Br | H | Br | H | H | CH₃OCH(Me)CH₂CO |
| 7-339 | Br | H | Br | H | H | EtNHCO |
| 7-340 | Br | H | Br | H | H | tert-BuOC(=O) |
| 7-341 | Cl | H | Cl | H | Me | H |
| 7-342 | Cl | H | Cl | H | Me | MeCO |
| 7-343 | Cl | H | Cl | H | Me | EtCO |

TABLE 7-continued

| Compound No. | X² | X³ | X⁴ | Y³ | R¹ | R⁴ |
|---|---|---|---|---|---|---|
| 7-344 | Cl | H | Cl | H | Me | n-PrCO |
| 7-345 | Cl | H | Cl | H | Me | cyclo-PrCO |
| 7-345-a | Cl | H | Cl | H | Me | cyclo-PrCO |
| 7-346 | Cl | H | Cl | H | Me | cyclo-PrCH₂CO |
| 7-347 | Cl | H | Cl | H | Me | CF₃CH₂CO |
| 7-348 | Cl | H | Cl | H | Me | CH₃SCH₂CO |
| 7-349 | Cl | H | Cl | H | Me | CH₃SOCH₂CO |
| 7-350 | Cl | H | Cl | H | Me | CH₃SO₂CH₂CO |
| 7-351 | Cl | H | Cl | H | Me | CH₃OCH₂CH₂CO |
| 7-352 | Cl | H | Cl | H | Me | CH₃OCH(Me)CH₂CO |
| 7-353 | Cl | H | Cl | H | Me | EtNHCO |
| 7-354 | Cl | H | Cl | H | Me | tert-BuOC(=O) |
| 7-355 | Br | H | Br | H | Me | H |
| 7-356 | Br | H | Br | H | Me | MeCO |
| 7-357 | Br | H | Br | H | Me | EtCO |
| 7-358 | Br | H | Br | H | Me | n-PrCO |
| 7-359 | Br | H | Br | H | Me | cyclo-PrCO |
| 7-360 | Br | H | Br | H | Me | cyclo-PrCH₂CO |
| 7-361 | Br | H | Br | H | Me | CF₃CH₂CO |
| 7-362 | Br | H | Br | H | Me | CH₃SCH₂CO |
| 7-363 | Br | H | Br | H | Me | CH₃SOCH₂CO |
| 7-364 | Br | H | Br | H | Me | CH₃SO₂CH₂CO |
| 7-365 | Br | H | Br | H | Me | CH₃OCH₂CH₂CO |
| 7-366 | Br | H | Br | H | Me | CH₃OCH(Me)CH₂CO |
| 7-367 | Br | H | Br | H | Me | EtNHCO |
| 7-368 | Br | H | Br | H | Me | tert-BuOC(=O) |
| 7-369 | Cl | Cl | Cl | H | Me | H |
| 7-370 | Cl | Cl | Cl | H | Me | MeCO |
| 7-370-a | Cl | Cl | Cl | H | Me | MeCO |
| 7-371 | Cl | Cl | Cl | H | Me | EtCO |
| 7-371-a | Cl | Cl | Cl | H | Me | EtCO |
| 7-371-b | Cl | Cl | Cl | H | Me | EtCO |
| 7-372 | Cl | Cl | Cl | H | Me | n-PrCO |
| 7-373 | Cl | Cl | Cl | H | Me | cyclo-PrCO |
| 7-373-a | Cl | Cl | Cl | H | Me | cyclo-PrCO |
| 7-374 | Cl | Cl | Cl | H | Me | cyclo-PrCH₂CO |
| 7-374-a | Cl | Cl | Cl | H | Me | cyclo-PrCH₂CO |
| 7-375 | Cl | Cl | Cl | H | Me | CF₃CH₂CO |
| 7-375-a | Cl | Cl | Cl | H | Me | CF₃CH₂CO |
| 7-376 | Cl | Cl | Cl | H | Me | CH₃SCH₂CO |
| 7-377 | Cl | Cl | Cl | H | Me | CH₃SOCH₂CO |
| 7-378 | Cl | Cl | Cl | H | Me | CH₃SO₂CH₂CO |
| 7-379 | Cl | Cl | Cl | H | Me | CH₃OCH₂CH₂CO |
| 7-379-a | Cl | Cl | Cl | H | Me | CH₃OCH₂CH₂CO |
| 7-380 | Cl | Cl | Cl | H | Me | CH₃OCH(Me)CH₂CO |
| 7-381 | Cl | Cl | Cl | H | Me | EtNHCO |
| 7-382 | Cl | Cl | Cl | H | Me | tert-BuOC(=O) |
| 7-383 | CF₃ | H | H | H | Me | H |
| 7-384 | CF₃ | H | H | H | Me | MeCO |
| 7-385 | CF₃ | H | H | H | Me | EtCO |
| 7-386 | CF₃ | H | H | H | Me | n-PrCO |
| 7-387 | CF₃ | H | H | H | Me | cyclo-PrCO |
| 7-388 | CF₃ | H | H | H | Me | cyclo-PrCH₂CO |
| 7-389 | CF₃ | H | H | H | Me | CF₃CH₂CO |
| 7-390 | CF₃ | H | H | H | Me | CH₃SCH₂CO |
| 7-391 | CF₃ | H | H | H | Me | CH₃SOCH₂CO |
| 7-392 | CF₃ | H | H | H | Me | CH₃SO₂CH₂CO |
| 7-393 | CF₃ | H | H | H | Me | CH₃OCH₂CH₂CO |
| 7-394 | CF₃ | H | H | H | Me | CH₃OCH(Me)CH₂CO |
| 7-395 | CF₃ | H | H | H | Me | EtNHCO |
| 7-396 | CF₃ | H | H | H | Me | tert-BuOC(=O) |
| 7-397 | CF₃ | H | CF₃ | H | Me | H |
| 7-398 | CF₃ | H | CF₃ | H | Me | MeCO |
| 7-398-a | CF₃ | H | CF₃ | H | Me | MeCO |
| 7-399 | CF₃ | H | CF₃ | H | Me | EtCO |
| 7-399-a | CF₃ | H | CF₃ | H | Me | EtCO |
| 7-399-b | CF₃ | H | CF₃ | H | Me | EtCO |
| 7-400 | CF₃ | H | CF₃ | H | Me | n-PrCO |
| 7-401 | CF₃ | H | CF₃ | H | Me | cyclo-PrCO |
| 7-401-a | CF₃ | H | CF₃ | H | Me | cyclo-PrCO |
| 7-402 | CF₃ | H | CF₃ | H | Me | cyclo-PrCH₂CO |
| 7-402-a | CF₃ | H | CF₃ | H | Me | cyclo-PrCH₂CO |
| 7-403 | CF₃ | H | CF₃ | H | Me | CF₃CH₂CO |
| 7-403-a | CF₃ | H | CF₃ | H | Me | CF₃CH₂CO |
| 7-404 | CF₃ | H | CF₃ | H | Me | CH₃SCH₂CO |
| 7-405 | CF₃ | H | CF₃ | H | Me | CH₃SOCH₂CO |
| 7-406 | CF₃ | H | CF₃ | H | Me | CH₃SO₂CH₂CO |
| 7-407 | CF₃ | H | CF₃ | H | Me | CH₃OCH₂CH₂CO |
| 7-407-a | CF₃ | H | CF₃ | H | Me | CH₃OCH₂CH₂CO |
| 7-408 | CF₃ | H | CF₃ | H | Me | CH₃OCH(Me)CH₂CO |
| 7-409 | CF₃ | H | CF₃ | H | Me | EtNHCO |
| 7-410 | CF₃ | H | CF₃ | H | Me | tert-BuOC(=O) |
| 7-411 | Cl | Cl | CF₃ | H | Me | H |
| 7-412 | Cl | Cl | CF₃ | H | Me | MeCO |
| 7-413 | Cl | Cl | CF₃ | H | Me | EtCO |
| 7-414 | Cl | Cl | CF₃ | H | Me | cyclo-PrCO |
| 7-415 | Cl | Cl | CF₃ | H | Me | CH₃SCH₂CO |
| 7-416 | Cl | Cl | CF₃ | H | Me | CF₃CH₂CO |
| 7-417 | Cl | Cl | CF₃ | H | Me | EtNHCO |
| 7-418 | Cl | Cl | CF₃ | H | Me | tert-BuOC(=O) |
| 7-419 | Cl | H | CF₃ | H | Me | H |
| 7-420 | Cl | H | CF₃ | H | Me | MeCO |
| 7-421 | Cl | H | CF₃ | H | Me | EtCO |
| 7-422 | Cl | H | CF₃ | H | Me | cyclo-PrCO |
| 7-423 | Cl | H | CF₃ | H | Me | CH₃SCH₂CO |
| 7-424 | Cl | H | CF₃ | H | Me | CF₃CH₂CO |
| 7-425 | Cl | H | CF₃ | H | Me | EtNHCO |
| 7-426 | Cl | H | CF₃ | H | Me | tert-BuOC(=O) |
| 7-427 | F | H | CF₃ | H | Me | H |
| 7-428 | F | H | CF₃ | H | Me | MeCO |
| 7-429 | F | H | CF₃ | H | Me | EtCO |
| 7-430 | F | H | CF₃ | H | Me | cyclo-PrCO |
| 7-431 | F | H | CF₃ | H | Me | CH₃SCH₂CO |
| 7-432 | F | H | CF₃ | H | Me | CF₃CH₂CO |
| 7-433 | F | H | CF₃ | H | Me | EtNHCO |
| 7-434 | F | H | CF₃ | H | Me | tert-BuOC(=O) |
| 7-435 | H | F | CF₃ | H | Me | H |
| 7-436 | H | F | CF₃ | H | Me | MeCO |
| 7-437 | H | F | CF₃ | H | Me | EtCO |
| 7-438 | H | F | CF₃ | H | Me | cyclo-PrCO |
| 7-439 | H | F | CF₃ | H | Me | CH₃SCH₂CO |
| 7-440 | H | F | CF₃ | H | Me | CF₃CH₂CO |
| 7-441 | H | F | CF₃ | H | Me | EtNHCO |
| 7-442 | H | F | CF₃ | H | Me | tert-BuOC(=O) |
| 7-443 | OCF₃ | H | H | CF₃ | H | EtCO |
| 7-444 | SCF₃ | H | H | CF₃ | H | EtCO |
| 7-445 | SOCF₃ | H | H | CF₃ | H | EtCO |
| 7-446 | SO₂CF₃ | H | H | CF₃ | H | EtCO |

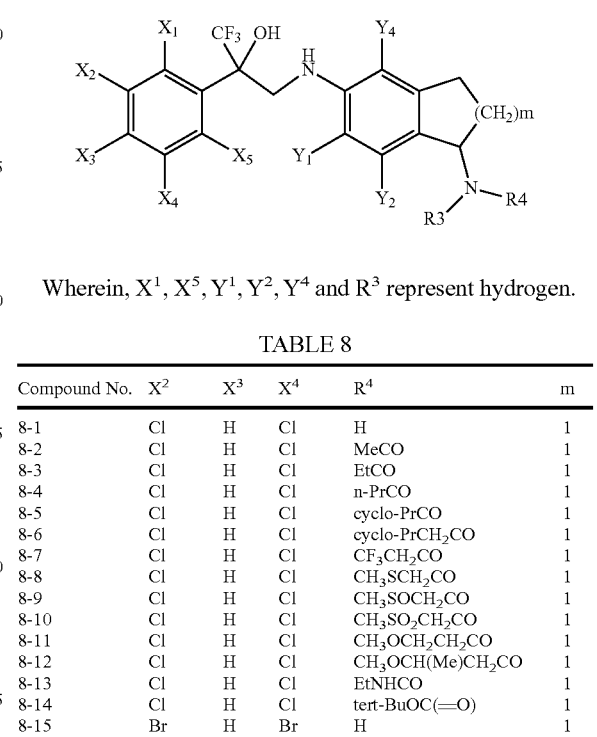

Wherein, $X^1$, $X^5$, $Y^1$, $Y^2$, $Y^4$ and $R^3$ represent hydrogen.

TABLE 8

| Compound No. | X² | X³ | X⁴ | R⁴ | m |
|---|---|---|---|---|---|
| 8-1 | Cl | H | Cl | H | 1 |
| 8-2 | Cl | H | Cl | MeCO | 1 |
| 8-3 | Cl | H | Cl | EtCO | 1 |
| 8-4 | Cl | H | Cl | n-PrCO | 1 |
| 8-5 | Cl | H | Cl | cyclo-PrCO | 1 |
| 8-6 | Cl | H | Cl | cyclo-PrCH₂CO | 1 |
| 8-7 | Cl | H | Cl | CF₃CH₂CO | 1 |
| 8-8 | Cl | H | Cl | CH₃SCH₂CO | 1 |
| 8-9 | Cl | H | Cl | CH₃SOCH₂CO | 1 |
| 8-10 | Cl | H | Cl | CH₃SO₂CH₂CO | 1 |
| 8-11 | Cl | H | Cl | CH₃OCH₂CH₂CO | 1 |
| 8-12 | Cl | H | Cl | CH₃OCH(Me)CH₂CO | 1 |
| 8-13 | Cl | H | Cl | EtNHCO | 1 |
| 8-14 | Cl | H | Cl | tert-BuOC(=O) | 1 |
| 8-15 | Br | H | Br | H | 1 |

TABLE 8-continued

| Compound No. | X² | X³ | X⁴ | R⁴ | m |
|---|---|---|---|---|---|
| 8-16 | Br | H | Br | MeCO | 1 |
| 8-17 | Br | H | Br | EtCO | 1 |
| 8-18 | Br | H | Br | n-PrCO | 1 |
| 8-19 | Br | H | Br | cyclo-PrCO | 1 |
| 8-20 | Br | H | Br | cyclo-PrCH₂CO | 1 |
| 8-21 | Br | H | Br | CF₃CH₂CO | 1 |
| 8-22 | Br | H | Br | CH₃SCH₂CO | 1 |
| 8-23 | Br | H | Br | CH₃SOCH₂CO | 1 |
| 8-24 | Br | H | Br | CH₃SO₂CH₂CO | 1 |
| 8-25 | Br | H | Br | CH₃OCH₂CH₂CO | 1 |
| 8-26 | Br | H | Br | CH₃OCH(Me)CH₂CO | 1 |
| 8-27 | Br | H | Br | EtNHCO | 1 |
| 8-28 | Br | H | Br | tert-BuOC(=O) | 1 |
| 8-29 | Cl | Cl | Cl | H | 1 |
| 8-30 | Cl | Cl | Cl | MeCO | 1 |
| 8-31 | Cl | Cl | Cl | EtCO | 1 |
| 8-32 | Cl | Cl | Cl | n-PrCO | 1 |
| 8-33 | Cl | Cl | Cl | cyclo-PrCO | 1 |
| 8-34 | Cl | Cl | Cl | cyclo-PrCH₂CO | 1 |
| 8-35 | Cl | Cl | Cl | CF₃CH₂CO | 1 |
| 8-36 | Cl | Cl | Cl | CH₃SCH₂CO | 1 |
| 8-37 | Cl | Cl | Cl | CH₃SOCH₂CO | 1 |
| 8-38 | Cl | Cl | Cl | CH₃SO₂CH₂CO | 1 |
| 8-39 | Cl | Cl | Cl | CH₃OCH₂CH₂CO | 1 |
| 8-40 | Cl | Cl | Cl | CH₃OCH(Me)CH₂CO | 1 |
| 8-41 | Cl | Cl | Cl | EtNHCO | 1 |
| 8-42 | Cl | Cl | Cl | tert-BuOC(=O) | 1 |
| 8-43 | CF₃ | H | H | H | 1 |
| 8-44 | CF₃ | H | H | MeCO | 1 |
| 8-45 | CF₃ | H | H | EtCO | 1 |
| 8-46 | CF₃ | H | H | n-PrCO | 1 |
| 8-47 | CF₃ | H | H | cyclo-PrCO | 1 |
| 8-48 | CF₃ | H | H | cyclo-PrCH₂CO | 1 |
| 8-49 | CF₃ | H | H | CF₃CH₂CO | 1 |
| 8-50 | CF₃ | H | H | CH₃SCH₂CO | 1 |
| 8-51 | CF₃ | H | H | CH₃SOCH₂CO | 1 |
| 8-52 | CF₃ | H | H | CH₃SO₂CH₂CO | 1 |
| 8-53 | CF₃ | H | H | CH₃OCH₂CH₂CO | 1 |
| 8-54 | CF₃ | H | H | CH₃OCH(Me)CH₂CO | 1 |
| 8-55 | CF₃ | H | H | EtNHCO | 1 |
| 8-56 | CF₃ | H | H | tert-BuOC(=O) | 1 |
| 8-57 | CF₃ | H | CF₃ | H | 1 |
| 8-58 | CF₃ | H | CF₃ | MeCO | 1 |
| 8-59 | CF₃ | H | CF₃ | EtCO | 1 |
| 8-60 | CF₃ | H | CF₃ | n-PrCO | 1 |
| 8-61 | CF₃ | H | CF₃ | cyclo-PrCO | 1 |
| 8-62 | CF₃ | H | CF₃ | cyclo-PrCH₂CO | 1 |
| 8-63 | CF₃ | H | CF₃ | CF₃CH₂CO | 1 |
| 8-64 | CF₃ | H | CF₃ | CH₃SCH₂CO | 1 |
| 8-65 | CF₃ | H | CF₃ | CH₃SOCH₂CO | 1 |
| 8-66 | CF₃ | H | CF₃ | CH₃SO₂CH₂CO | 1 |
| 8-67 | CF₃ | H | CF₃ | CH₃OCH₂CH₂CO | 1 |
| 8-68 | CF₃ | H | CF₃ | CH₃OCH(Me)CH₂CO | 1 |
| 8-69 | CF₃ | H | CF₃ | EtNHCO | 1 |
| 8-70 | CF₃ | H | CF₃ | tert-BuOC(=O) | 1 |
| 8-71 | Cl | Cl | CF₃ | H | 1 |
| 8-72 | Cl | Cl | CF₃ | MeCO | 1 |
| 8-73 | Cl | Cl | CF₃ | EtCO | 1 |
| 8-74 | Cl | Cl | CF₃ | cyclo-PrCO | 1 |
| 8-75 | Cl | Cl | CF₃ | CH₃SCH₂CO | 1 |
| 8-76 | Cl | Cl | CF₃ | CF₃CH₂CO | 1 |
| 8-77 | Cl | Cl | CF₃ | EtNHCO | 1 |
| 8-78 | Cl | Cl | CF₃ | tert-BuOC(=O) | 1 |
| 8-79 | Cl | H | CF₃ | H | 1 |
| 8-80 | Cl | H | CF₃ | MeCO | 1 |
| 8-81 | Cl | H | CF₃ | EtCO | 1 |
| 8-82 | Cl | H | CF₃ | cyclo-PrCO | 1 |
| 8-83 | Cl | H | CF₃ | CH₃SCH₂CO | 1 |
| 8-84 | Cl | H | CF₃ | CF₃CH₂CO | 1 |
| 8-85 | Cl | H | CF₃ | EtNHCO | 1 |
| 8-86 | Cl | H | CF₃ | tert-BuOC(=O) | 1 |
| 8-87 | F | H | CF₃ | H | 1 |
| 8-88 | F | H | CF₃ | MeCO | 1 |
| 8-89 | F | H | CF₃ | EtCO | 1 |
| 8-90 | F | H | CF₃ | cyclo-PrCO | 1 |
| 8-91 | F | H | CF₃ | CH₃SCH₂CO | 1 |
| 8-92 | F | H | CF₃ | CF₃CH₂CO | 1 |
| 8-93 | F | H | CF₃ | EtNHCO | 1 |
| 8-94 | F | H | CF₃ | tert-BuOC(=O) | 1 |
| 8-95 | H | F | CF₃ | H | 1 |
| 8-96 | H | F | CF₃ | MeCO | 1 |
| 8-97 | H | F | CF₃ | EtCO | 1 |
| 8-98 | H | F | CF₃ | cyclo-PrCO | 1 |
| 8-99 | H | F | CF₃ | CH₃SCH₂CO | 1 |
| 8-100 | H | F | CF₃ | CF₃CH₂CO | 1 |
| 8-101 | H | F | CF₃ | EtNHCO | 1 |
| 8-102 | H | F | CF₃ | tert-BuOC(=O) | 1 |
| 8-103 | Cl | H | Cl | H | 2 |
| 8-104 | Cl | H | Cl | MeCO | 2 |
| 8-105 | Cl | H | Cl | EtCO | 2 |
| 8-106 | Cl | H | Cl | n-PrCO | 2 |
| 8-107 | Cl | H | Cl | cyclo-PrCO | 2 |
| 8-108 | Cl | H | Cl | cyclo-PrCH₂CO | 2 |
| 8-109 | Cl | H | Cl | CF₃CH₂CO | 2 |
| 8-110 | Cl | H | Cl | CH₃SCH₂CO | 2 |
| 8-111 | Cl | H | Cl | CH₃SOCH₂CO | 2 |
| 8-112 | Cl | H | Cl | CH₃SO₂CH₂CO | 2 |
| 8-113 | Cl | H | Cl | CH₃OCH₂CH₂CO | 2 |
| 8-114 | Cl | H | Cl | CH₃OCH(Me)CH₂CO | 2 |
| 8-115 | Cl | H | Cl | EtNHCO | 2 |
| 8-116 | Cl | H | Cl | tert-BuOC(=O) | 2 |
| 8-117 | Br | H | Br | H | 2 |
| 8-118 | Br | H | Br | MeCO | 2 |
| 8-119 | Br | H | Br | EtCO | 2 |
| 8-120 | Br | H | Br | n-PrCO | 2 |
| 8-121 | Br | H | Br | cyclo-PrCO | 2 |
| 8-122 | Br | H | Br | cyclo-PrCH₂CO | 2 |
| 8-123 | Br | H | Br | CF₃CH₂CO | 2 |
| 8-124 | Br | H | Br | CH₃SCH₂CO | 2 |
| 8-125 | Br | H | Br | CH₃SOCH₂CO | 2 |
| 8-126 | Br | H | Br | CH₃SO₂CH₂CO | 2 |
| 8-127 | Br | H | Br | CH₃OCH₂CH₂CO | 2 |
| 8-128 | Br | H | Br | CH₃OCH(Me)CH₂CO | 2 |
| 8-129 | Br | H | Br | EtNHCO | 2 |
| 8-130 | Br | H | Br | tert-BuOC(=O) | 2 |
| 8-131 | Cl | Cl | Cl | H | 2 |
| 8-132 | Cl | Cl | Cl | MeCO | 2 |
| 8-133 | Cl | Cl | Cl | EtCO | 2 |
| 8-134 | Cl | Cl | Cl | n-PrCO | 2 |
| 8-135 | Cl | Cl | Cl | cyclo-PrCO | 2 |
| 8-136 | Cl | Cl | Cl | cyclo-PrCH₂CO | 2 |
| 8-137 | Cl | Cl | Cl | CF₃CH₂CO | 2 |
| 8-138 | Cl | Cl | Cl | CH₃SCH₂CO | 2 |
| 8-139 | Cl | Cl | Cl | CH₃SOCH₂CO | 2 |
| 8-140 | Cl | Cl | Cl | CH₃SO₂CH₂CO | 2 |
| 8-141 | Cl | Cl | Cl | CH₃OCH₂CH₂CO | 2 |
| 8-142 | Cl | Cl | Cl | CH₃OCH(Me)CH₂CO | 2 |
| 8-143 | Cl | Cl | Cl | EtNHCO | 2 |
| 8-144 | Cl | Cl | Cl | tert-BuOC(=O) | 2 |
| 8-145 | CF₃ | H | H | H | 2 |
| 8-146 | CF₃ | H | H | MeCO | 2 |
| 8-147 | CF₃ | H | H | EtCO | 2 |
| 8-148 | CF₃ | H | H | n-PrCO | 2 |
| 8-149 | CF₃ | H | H | cyclo-PrCO | 2 |
| 8-150 | CF₃ | H | H | cyclo-PrCH₂CO | 2 |
| 8-151 | CF₃ | H | H | CF₃CH₂CO | 2 |
| 8-152 | CF₃ | H | H | CH₃SCH₂CO | 2 |
| 8-153 | CF₃ | H | H | CH₃SOCH₂CO | 2 |
| 8-154 | CF₃ | H | H | CH₃SO₂CH₂CO | 2 |
| 8-155 | CF₃ | H | H | CH₃OCH₂CH₂CO | 2 |
| 8-156 | CF₃ | H | H | CH₃OCH(Me)CH₂CO | 2 |
| 8-157 | CF₃ | H | H | EtNHCO | 2 |
| 8-158 | CF₃ | H | H | tert-BuOC(=O) | 2 |
| 8-159 | CF₃ | H | CF₃ | H | 2 |
| 8-160 | CF₃ | H | CF₃ | MeCO | 2 |
| 8-161 | CF₃ | H | CF₃ | EtCO | 2 |
| 8-162 | CF₃ | H | CF₃ | n-PrCO | 2 |
| 8-163 | CF₃ | H | CF₃ | cyclo-PrCO | 2 |
| 8-164 | CF₃ | H | CF₃ | cyclo-PrCH₂CO | 2 |
| 8-165 | CF₃ | H | CF₃ | CF₃CH₂CO | 2 |
| 8-166 | CF₃ | H | CF₃ | CH₃SCH₂CO | 2 |
| 8-167 | CF₃ | H | CF₃ | CH₃SOCH₂CO | 2 |
| 8-168 | CF₃ | H | CF₃ | CH₃SO₂CH₂CO | 2 |
| 8-169 | CF₃ | H | CF₃ | CH₃OCH₂CH₂CO | 2 |
| 8-170 | CF₃ | H | CF₃ | CH₃OCH(Me)CH₂CO | 2 |
| 8-171 | CF₃ | H | CF₃ | EtNHCO | 2 |

TABLE 8-continued

| Compound No. | $X^2$ | $X^3$ | $X^4$ | $R^4$ | m |
|---|---|---|---|---|---|
| 8-172 | $CF_3$ | H | $CF_3$ | tert-BuOC(=O) | 2 |
| 8-173 | Cl | Cl | $CF_3$ | H | 2 |
| 8-174 | Cl | Cl | $CF_3$ | MeCO | 2 |
| 8-175 | Cl | Cl | $CF_3$ | EtCO | 2 |
| 8-176 | Cl | Cl | $CF_3$ | cyclo-PrCO | 2 |
| 8-177 | Cl | Cl | $CF_3$ | $CH_3SCH_2CO$ | 2 |
| 8-178 | Cl | Cl | $CF_3$ | $CF_3CH_2CO$ | 2 |
| 8-179 | Cl | Cl | $CF_3$ | EtNHCO | 2 |
| 8-180 | Cl | Cl | $CF_3$ | tert-BuOC(=O) | 2 |
| 8-181 | Cl | H | $CF_3$ | H | 2 |
| 8-182 | Cl | H | $CF_3$ | MeCO | 2 |
| 8-183 | Cl | H | $CF_3$ | EtCO | 2 |
| 8-184 | Cl | H | $CF_3$ | cyclo-PrCO | 2 |
| 8-185 | Cl | H | $CF_3$ | $CH_3SCH_2CO$ | 2 |
| 8-186 | Cl | H | $CF_3$ | $CF_3CH_2CO$ | 2 |
| 8-187 | Cl | H | $CF_3$ | EtNHCO | 2 |
| 8-188 | Cl | H | $CF_3$ | tert-BuOC(=O) | 2 |
| 8-189 | F | H | $CF_3$ | H | 2 |
| 8-190 | F | H | $CF_3$ | MeCO | 2 |
| 8-191 | F | H | $CF_3$ | EtCO | 2 |
| 8-192 | F | H | $CF_3$ | cyclo-PrCO | 2 |
| 8-193 | F | H | $CF_3$ | $CH_3SCH_2CO$ | 2 |
| 8-194 | F | H | $CF_3$ | $CF_3CH_2CO$ | 2 |
| 8-195 | F | H | $CF_3$ | EtNHCO | 2 |
| 8-196 | F | H | $CF_3$ | tert-BuOC(=O) | 2 |
| 8-197 | H | F | $CF_3$ | H | 2 |
| 8-198 | H | F | $CF_3$ | MeCO | 2 |
| 8-199 | H | F | $CF_3$ | EtCO | 2 |
| 8-200 | H | F | $CF_3$ | cyclo-PrCO | 2 |
| 8-201 | H | F | $CF_3$ | $CH_3SCH_2CO$ | 2 |
| 8-202 | H | F | $CF_3$ | $CF_3CH_2CO$ | 2 |
| 8-203 | H | F | $CF_3$ | EtNHCO | 2 |
| 8-204 | H | F | $CF_3$ | tert-BuOC(=O) | 2 |
| 8-205 | $OCF_3$ | H | H | EtCO | 1 |
| 8-206 | $SCF_3$ | H | H | EtCO | 1 |
| 8-207 | $SOCF_3$ | H | H | EtCO | 1 |
| 8-208 | $SO_2CF_3$ | H | H | EtCO | 1 |

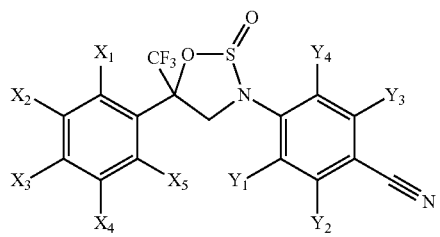

Wherein, $X^1$, $X^5$, $Y^1$, $Y^2$ and $Y^4$ represent hydrogen.

TABLE 9

| Compound No. | $X^2$ | $X^3$ | $X^4$ | $Y^3$ |
|---|---|---|---|---|
| 9-1 | Cl | H | Cl | $CF_3$ |
| 9-2 | Cl | H | Cl | Cl |
| 9-3 | Cl | H | Cl | Br |
| 9-4 | Cl | H | Cl | Me |
| 9-5 | Cl | H | Cl | H |
| 9-6 | Br | H | Br | $CF_3$ |
| 9-7 | Br | H | Br | Cl |
| 9-8 | Br | H | Br | Br |
| 9-9 | Br | H | Br | Me |
| 9-10 | Br | H | Br | H |
| 9-11 | Cl | Cl | Cl | $CF_3$ |
| 9-12 | Cl | Cl | Cl | Cl |
| 9-13 | Cl | Cl | Cl | Me |
| 9-14 | Cl | Cl | Cl | H |
| 9-15 | $CF_3$ | H | H | $CF_3$ |
| 9-16 | $CF_3$ | H | H | Cl |
| 9-17 | $CF_3$ | H | H | Me |
| 9-18 | $CF_3$ | H | H | H |
| 9-19 | $CF_3$ | H | $CF_3$ | $CF_3$ |
| 9-20 | $CF_3$ | H | $CF_3$ | Cl |
| 9-21 | $CF_3$ | H | $CF_3$ | Me |
| 9-22 | $CF_3$ | H | $CF_3$ | H |
| 9-23 | Cl | Cl | $CF_3$ | $CF_3$ |
| 9-24 | Cl | H | $CF_3$ | $CF_3$ |
| 9-25 | F | H | $CF_3$ | $CF_3$ |
| 9-26 | H | F | $CF_3$ | $CF_3$ |
| 9-27 | $OCF_3$ | H | H | $CF_3$ |
| 9-28 | $SCF_3$ | H | H | $CF_3$ |
| 9-29 | $SOCF_3$ | H | H | $CF_3$ |
| 9-30 | $SO_2CF_3$ | H | H | $CF_3$ |

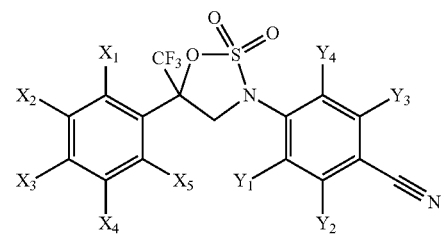

Wherein, $X^1$, $X^5$, $Y^1$, $Y^2$ and $Y^4$ represent hydrogen.

TABLE 10

| Compound No. | $X^2$ | $X^3$ | $X^4$ | $Y^3$ |
|---|---|---|---|---|
| 10-1 | Cl | H | Cl | $CF_3$ |
| 10-2 | Cl | H | Cl | Cl |
| 10-3 | Cl | H | Cl | Br |
| 10-4 | Cl | H | Cl | Me |
| 10-5 | Cl | H | Cl | H |
| 10-6 | Br | H | Br | $CF_3$ |
| 10-7 | Br | H | Br | Cl |
| 10-8 | Br | H | Br | Br |
| 10-9 | Br | H | Br | Me |
| 10-10 | Br | H | Br | H |
| 10-11 | Cl | Cl | Cl | $CF_3$ |
| 10-12 | Cl | Cl | Cl | Cl |
| 10-13 | Cl | Cl | Cl | Me |
| 10-14 | Cl | Cl | Cl | H |
| 10-15 | $CF_3$ | H | H | $CF_3$ |
| 10-16 | $CF_3$ | H | H | Cl |
| 10-17 | $CF_3$ | H | H | Me |
| 10-18 | $CF_3$ | H | H | H |
| 10-19 | $CF_3$ | H | $CF_3$ | $CF_3$ |
| 10-20 | $CF_3$ | H | $CF_3$ | Cl |
| 10-21 | $CF_3$ | H | $CF_3$ | Me |
| 10-22 | $CF_3$ | H | $CF_3$ | H |
| 10-23 | Cl | Cl | $CF_3$ | $CF_3$ |
| 10-24 | Cl | H | $CF_3$ | $CF_3$ |
| 10-25 | F | H | $CF_3$ | $CF_3$ |
| 10-26 | H | F | $CF_3$ | $CF_3$ |
| 10-27 | $OCF_3$ | H | H | $CF_3$ |
| 10-28 | $SCF_3$ | H | H | $CF_3$ |
| 10-29 | $SOCF_3$ | H | H | $CF_3$ |
| 10-30 | $SO_2CF_3$ | H | H | $CF_3$ |

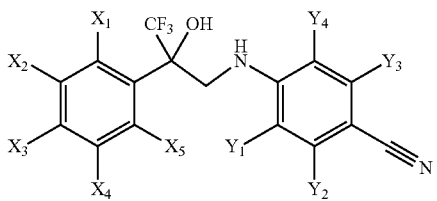

Wherein, $X^1$, $X^5$, $Y^1$, $Y^2$ and $Y^4$ represent hydrogen.

TABLE 11

| Compound No. | $X^2$ | $X^3$ | $X^4$ | $Y^3$ |
|---|---|---|---|---|
| 11-1 | Cl | H | Cl | $CF_3$ |
| 11-2 | Cl | H | Cl | Cl |
| 11-3 | Cl | H | Cl | Br |
| 11-4 | Cl | H | Cl | Me |
| 11-5 | Cl | H | Cl | H |
| 11-6 | Br | H | Br | $CF_3$ |
| 11-7 | Br | H | Br | Cl |
| 11-8 | Br | H | Br | Br |
| 11-9 | Br | H | Br | Me |

TABLE 11-continued

| Compound No. | $X^2$ | $X^3$ | $X^4$ | $Y^3$ |
|---|---|---|---|---|
| 11-10 | Br | H | Br | H |
| 11-11 | Cl | Cl | Cl | $CF_3$ |
| 11-12 | Cl | Cl | Cl | Cl |
| 11-13 | Cl | Cl | Cl | Me |
| 11-14 | Cl | Cl | Cl | H |
| 11-15 | $CF_3$ | H | H | $CF_3$ |
| 11-16 | $CF_3$ | H | H | Cl |
| 11-17 | $CF_3$ | H | H | Me |
| 11-18 | $CF_3$ | H | H | H |
| 11-19 | $CF_3$ | H | $CF_3$ | $CF_3$ |
| 11-20 | $CF_3$ | H | $CF_3$ | Cl |
| 11-21 | $CF_3$ | H | $CF_3$ | Me |
| 11-22 | $CF_3$ | H | $CF_3$ | H |
| 11-23 | Cl | Cl | $CF_3$ | $CF_3$ |
| 11-24 | Cl | H | $CF_3$ | $CF_3$ |
| 11-25 | F | H | $CF_3$ | $CF_3$ |
| 11-26 | H | F | $CF_3$ | $CF_3$ |
| 11-27 | $OCF_3$ | H | H | $CF_3$ |
| 11-28 | $SCF_3$ | H | H | $CF_3$ |
| 11-29 | $SOCF_3$ | H | H | $CF_3$ |
| 11-30 | $SO_2CF_3$ | H | H | $CF_3$ |

(NMR Table)

TABLE 12

| Compound No. | 1H-NMR |
|---|---|
| 1-17 | 1H-NMR (CDCl3) δ: 1.13-1.16 (3H, m), 2.18-2.23 (3H, m), 3.77-3.81 (1H, m), 4.12-4.15 (1H, m), 4.50 (2H, d), 5.20 (2H, d), 5.73 (1H, br s), 6.67 (1H, d), 6.77 (1H, d), 7.48 (1H, d), 7.59 (2H, s). |
| 1-19 | 1H-NMR (CDCl3) δ: 7.59 (2H, s), 7.48 (1H, d), 6.77 (1H, d), 6.68 (1H, s), 5.88 (1H, s), 5.20 (2H, d), 4.52 (2H, d), 1.30 (1H, m), 0.98 (2H, m), 0.73 (2H, m). |
| 3-17 | 1H-NMR (CDCl3) δ: 1.14-1.16 (3H, m), 2.17-2.27 (2H, m), 4.09-4.74 (4H, m), 5.80 (1H, br s), 7.22-7.65 (5H, m). |
| 3-19 | 1H-NMR (CDCl3) δ: 7.64 (3H, m), 7.33 (2H, d), 5.97 (1H, s), 4.56 (4H, m), 1.34 (1H, m), 1.02-0.97 (2H, m), 0.80-0.75 (2H, m). |
| 3-20 | 1H-NMR (CDCl3) δ: 7.47 (2H, m), 7.21-7.00 (2H, m), 6.34 (1H, m), 4.58-4.05 (3H, m), 3.60 (1H, m), 2.01 (2H, m), 0.84-0.66 (1H, m), 0.50-0.39 (2H, m), 0.00 (2H, m). |
| 3-73 | 1H-NMR (CDCl3) δ: 1.11-1.18 (3H, m), 2.16-2.24 (2H, m), 4.07-4.40 (4H, m), 5.82 (1H, br s), 7.21-7.92 (7H, m). |
| 3-382 | 1H-NMR (CDCl3) δ: 7.63 (2H, s), 7.48-7.33 (3H, m), 7.14 (1H, m), 6.66 (1H, d), 4.68 (1H, m), 4.24 (1H, m), 4.15 (1H, m), 1.43 (12H, m). |
| 4-3 | 1H-NMR (CDCl3) δ: 1.04-1.07 (3H, m), 1.64-1.74 (1H, m), 2.08-2.18 (2H, m), 2.42-2.46 (1H, m), 2.69-2.85 (2H, m), 4.10-4.27 (1H, m), 4.46-4.57 (1H, m), 5.27-5.30 (1H, m), 6.04-6.07 (1H, m), 6.80-7.01 (2H, m), 7.10-7.23 (1H, m), 7.36-7.44 (3H, m). |
| 5-17 | 1H-NMR (CDCl3) δ: 7.68-7.47 (4H, m), 7.29 (1H, m), 5.87 (1H, m), 4.67-4.23 (4H, m), 2.28-2.18 (2H, m), 1.18-1.11 (3H, t). |
| 5-19 | 1H-NMR (CDCl3) δ: 7.73-7.18 (5H, m), 6.11 (1H, m), 4.40 (4H, m), 1.43-1.31 (1H, m), 0.95 (2H, m), 0.78 (2H, m). |
| 5-20 | 1H-NMR (CDCl3) δ: 7.66-7.55 (3H, m), 7.37-7.19 (2H, m), 6.38 (1H, m), 4.64-4.55 (2H, m), 4.38 (1H, m), 4.23 (1H, m), 2.19-2.13 (2H, m), 0.97-0.85 (1H, m), 0.63-0.55 (2H, m), 0.17 (2H, m). |
| 5-374-a | 1H-NMR (CDCl3) δ: 7.60 (2H, m), 7.32 (4H, m), 6.11 (1H, m), 5.18-5.08 (1H, m), 4.56 (1H, m), 4.23 (1H, m), 2.15 (2H, m), 1.46 (3H, m), 0.96 (1H, m), 0.61 (2H, m), 0.19 (2H, m). |
| 5-375-a | 1H-NMR (CDCl3) δ: 7.60 (2H, m), 7.46-7.39 (2H, m), 7.27 (2H, m), 6.46 (1H, m), 5.12-5.03 (1H, m), 4.59 (1H, m), 4.28 (1H, m), 3.01 (2H, m), 1.51-1.43 (3H, m). |
| 6-3 | 1H-NMR (CDCl3) δ: 1.20 (3H, t), 1.81-1.84 (1H, m), 2.26 (2H, q), 2.62-2.65 (1H, m), 2.89-2.97 (2H, m), 4.24 (1H, d), 4.60 (1H, d), 5.50-5.56 (2H, m), 7.13-7.16 (1H, m), 7.28-7.32 (2H, m), 7.46 (2H, s), 7.52 (1H, s). |
| 7-17 | 1H-NMR (CDCl3) δ: 1.14 (3H, t), 2.21 (2H, q), 3.63-3.66 (1H, m), 3.88-3.93 (1H, m), 3.98-4.00 (1H, m), 4.40-4.43 (3H, m), 5.74 (1H, br s), 6.70-6.71 (1H, m), 6.86 (1H, m), 7.27-7.30 (1H, m), 7.64 (2H, s). |
| 7-19 | 1H-NMR (CDCl3) δ: 7.64 (2H, m), 7.10 (1H, m), 6.75 (1H, m), 6.54 (1H, m), 6.11 (1H, m), 5.53 (1H, m), 4.35 (2H, m), 4.22-4.14 (1H, m), 3.76 (2H, m), 1.37 (1H, m), 0.92 (2H, m), 0.79 (2H, m). |
| 7-20 | 1H-NMR (CDCl3) δ: 7.65 (2H, s), 6.84 (1H, d), 6.64 (1H, d), 6.33 (1H, s), 4.88 (1H, s), 4.45 (2H, d), 4.09 (1H, s), 3.77 (2H, m), 2.17 (1H, m), 0.89 (1H, m), 0.62-0.56 (2H, m), 0.16 (2H, m). |
| 7-21 | 1H-NMR (CDCl3) δ: 3.21 (2H, d), 3.65-3.68 (1H, m), 3.87-3.91 (1H, m), 4.48 (2H, d), 6.74 (1H, m), 6.86 (1H, s), 6.95 (1H, br s), 7.27-7.29 (1H, m), 7.64 (2H, s). |
| 7-73 | 1H-NMR (CDCl3) δ: 1.14 (3H, t), 2.19-2.22 (2H, m), 3.69-3.72 (1H, m), 3.96-4.00 (2H, m), 4.45 (2H, d), 5.70 (1H, br s), 6.75 (1H, d), 6.86 (1H, s), 7.35 (1H, m), 7.56-7.59 (1H, m), 7.69 (1H, d), 7.80 (1H, d.), 7.91 (1H, s). |

TABLE 12-continued

| Compound No. | 1H-NMR |
|---|---|
| 7-371-a | 1H-NMR (CDCl3) δ: 7.63 (2H, m), 7.33-7.02 (3H, m), 6.55 (1H, m), 5.74 (1H, m), 5.14 (1H, m), 5.00 (1H, m), 3.73 (2H, m), 2.23-2.13 (2H, m), 1.46-1.40 (3H, d), 1.13 (3H, t). |
| 7-373-a | 1H-NMR (CDCl3) δ: 7.63 (2H, m), 7.08 (2H, m), 6.59 (2H, m), 5.84 (1H, m), 5.01-4.94 (1H, m), 4.70 (1H, m), 3.92-3.54 (2H, m), 1.49-1.42 (3H, m), 1.36-1.27 (1H, m), 0.92 (2H, m), 0.71 (2H, m). |
| 9-11 | 1H-NMR (CDCl3) δ: 4.33 (1H, dd), 4.67 (1H, dd), 7.31-7.39 (2H, m), 7.62 (2H, d), 7.83-7.86 (1H, m). |
| 10-11 | 1H-NMR (CDCl3) δ: 4.36 (1H, d), 4.73 (1H, d), 7.57-7.64 (4H, m), 7.92 (1H, d). |
| 11-11 | 1H-NMR (CDCl3) δ: 3.77 (1H, dd), 3.93 (1H, dd), 4.47 (1H, br s), 6.78-6.81 (1H, m), 6.92 (1H, d), 7.58-7.61 (3H, m). |

Unless other methods are mentioned specifically, the sample solution preparation was prepared as follows.
Solvent: 3 parts by weight of dimethyl formamide
Emulsifier: 1 part by weight of polyoxyethylene alkyl phenyl ether
To prepare a suitable concoction including the active compound, 1 part by weight of the active compound was mixed with the above amount of the solvent containing the above amount of the emulsifier, and the resulting mixture was diluted with water to predetermined concentrations.

Biological Test Example 1

Test on *Tetranychus urticae*

(Test Method)
50 to 100 of adult *Tetranychus urticae* were inoculated to leaves at 2-leaf stage of Egyptian bean planted in pots of 6 cm in diameter, to which, 1 day later, the above prepared water diluted solution of the active compound at the predetermined concentration was sufficiently sprayed with a spray gun. After the compounds were sprayed, the pots were left in a greenhouse and the acaricidal ratio was calculated seven days later. 100% acaricidal ratio means death of all the mites, while 0% acaricidal ratio means none of the mites were dead.
(Test Result)
In the Biological Test Example 1 above, the following compounds as a representative example showed a pest-controlling efficacy of 100% acaricidal ratio at 100 ppm of an effective component concentration: Compound No. 1-17, 1-19, 5-17, 5-19, 5-20, 5-374-a and 5-375-a.

Biological Test Example 2

Test on *Aulacophora femoralis*

(Test Method)
Leaves of cucumbers were immersed in the water-diluted solution containing the active compound at the predetermined concentration which was prepared above and, after the solution was air-dried, the resultant leaves were put onto sterilized black soil in a plastic cup, into which five of the 2nd-instar larvae of *Aulacophora femoralis* were then released. The cup was covered with a lid and maintained in a temperature controlled room at 25° C. having humidity of 50 to 60%. Seven days later, the number of dead larvae was counted to calculate the pesticidal ratio. 100% pesticidal ratio means death of all the larvae, while 0% pesticidal ratio means no dead larvae.
(Test Result)
In the Biological Test Example 2 above, the following compounds as a representative example showed a pest-controlling efficacy of 100% pesticidal ratio at 100 ppm of an effective component concentration: Compound No. 1-17, 1-19, 3-17, 3-19, 3-20, 5-17, 5-19, 5-20, 5-374-a, 5-375-a and 7-19.

Biological Test Example 3

Test on Larvae of *Spodoptera litura* (a Method Using Artificial Feeds)

(Test Method)
Powdery artificial feeds (trade name: SILK MATE, manufactured by Nihon Nosan Kogyo, Japan, 2.3 g) were added to a plastic cup (diameter: 7.5 cm, height: 4 cm) to achieve a certain thickness. Water-diluted liquid (5 mL) of the active compound prepared above having predetermined concentration was evenly poured thereto and allowed to stand until the feeds are solidified. Five of the 3rd-instar larvae of *Spodoptera litura* were released in each cup, and covered with a lid. The cups were put in a temperature controlled room at 25° C. having humidity of 50 to 60%, and the number of dead larvae after 7 days was determined to calculate the pesticidal ratio. 100% pesticidal ratio means death of all the larvae, while 0% pesticidal ratio means no dead larvae.
(Test Result)
In the Biological Test Example 3 above, the following compounds as a representative example showed a pest-controlling efficacy of 100% pesticidal ratio at 100 ppm of an effective component concentration: Compound No. 1-17, 1-19, 3-17, 3-19, 3-20, 4-3, 5-17, 5-19, 5-20, 5-374-a, 5-375-a, 6-3, 7-19 and 10-11.

The invention claimed is:
1. An Aryl heterocycle derivative that is represented by Formula (I)

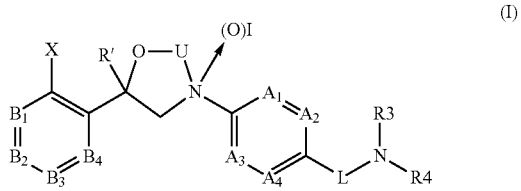

(I)

wherein R' represents $C_{1-12}$ alkyl or $C_{1-12}$ haloalkyl,
l represents 0 or 1,
U represents $CH_2$, S=O or $SO_2$,
$A_1$, $A_2$, $A_3$ and $A_4$ each independently represent C—Y or N, with the proviso that two of $A_1$, $A_2$, $A_3$ and $A_4$ may simultaneously represent N, or two Ys may form, together with the carbon atom to which they are bound, a benzene ring or a 5- to 6-membered heteroaromatic ring when $A_1$ and $A_2$ represent C—Y, $B_1$, $B_2$, $B_3$ and $B_4$ each independently represent C—X or N, L represents $(CR^1R^2)_n$, n represents 1, 2 or 3, $R^1$ and $R^2$ each independently represent hydrogen, cyano, $C_{1-12}$ alkyl, $C_{3-8}$ cycloalkyl, $C_{3-8}$ cycloalkyl-$C_{1-12}$ alkyl, $C_{2-6}$ alkenyl, $C_{2-6}$ alkynyl, $C_{1-12}$ alkoxy-carbonyl or $C_{1-12}$ thioalkoxy-carbonyl, and herein, each group from $C_{1-12}$ alkyl to $C_{1-12}$ thioalkoxy-carbonyl above may be optionally substituted with halogen, or $R^1$ and $R^2$ may form, together with the carbon atom to which they are bound, a 3- to 6-membered hydrocarbon ring, or $R^1$ may form, together with Y of $A_2$, $C_{2-3}$ alkylene when n represents 1 and $A_2$ represents C—Y, $R^3$ represents hydrogen, amino, hydroxy, cyano, $C_{1-12}$ alkyl, $C_{1-12}$ alkoxy, $C_{1-12}$ alkyl-carbonylamino, $C_{1-12}$ alkylamino, $C_{3-8}$ cycloalkyl, $C_{2-12}$ alkenyl, $C_{2-12}$ alkynyl, $C_{1-12}$ alkyl-carbonyl, —CH$_2$—R$^5$, —C(=O)R$^5$ or C(=S)R$^5$, and herein, each group from $C_{1-12}$ alkyl to $C_{1-12}$ alkyl-carbonyl above may be optionally substituted, $R^4$ represents hydrogen, cyano, formyl, thioformyl, $C_{1-12}$ alkyl-carbonyl, $C_{1-12}$ alkyl-thiocarbonyl, $C_{1-12}$ alkylamino-carbonyl, $C_{1-12}$ alkylamino-thiocarbonyl, $C_{2-24}$ (total carbon number) dialkylamino-carbonyl, $C_{2-24}$ (total carbon number) dialkylamino-thiocarbonyl, $C_{1-12}$ alkoxyamino-carbonyl, $C_{1-12}$ alkoxyamino-thiocarbonyl, $C_{1-12}$ alkoxy-carbonyl, $C_{1-12}$ alkoxy-$C_{1-12}$ alkyl-carbonyl, $C_{1-12}$ thioalkoxy-$C_{1-12}$ alkyl-carbonyl, $C_{1-12}$ alkylsulfenyl-$C_{1-12}$ alkyl-carbonyl, $C_{1-12}$ alkylsulfonyl-$C_{1-12}$ alkyl-carbonyl, $C_{1-12}$ alkoxy-thiocarbonyl, $C_{1-12}$ thioalkoxy-carbonyl, $C_{1-12}$ thioalkoxy-thiocarbonyl, $C_{1-12}$ alkylsulfonyl, $C_{3-8}$ cycloalkyl-carbonyl, $C_{3-8}$ cycloalkyl-$C_{1-12}$ alkyl-carbonyl, $C_{2-12}$ alkenyl-carbonyl, $C_{2-12}$ alkynyl-carbonyl, $C_{3-8}$ cycloalkylamino-carbonyl, $C_{2-12}$ alkenylamino-carbonyl, $C_{2-12}$ alkynylamino-carbonyl, —C(=O)R$^5$ or C(=S)R$^5$, and herein, each group from $C_{1-12}$ alkyl-carbonyl to $C_{2-12}$ alkylamino-carbonyl above may be optionally substituted, or $R^3$ and $R^4$ may form, together with the nitrogen atom to which they are bound, a 3- to 6-membered heterocycle, and herein, the heterocycle may be optionally substituted with X, keto, thioketo, or nitroimino, X and Y, which may be the same or different from each other, represent hydrogen, halogen, nitro, cyano, hydroxy, mercapto, SF$_5$, amino, $C_{1-12}$ alkyl, $C_{3-8}$ cycloalkyl, $C_{1-12}$ alkoxy, $C_{1-12}$ alkylthio, $C_{1-12}$ alkylsulfinyl, $C_{1-12}$ alkylsulfonyl, $C_{1-12}$ alkylsulfonyloxy, $C_{1-12}$ alkylaminosulfonyl, $C_{2-24}$ (total carbon number) dialkylaminosulfonyl, $C_{1-12}$ alkylcarbonylamino, benzoylamino, tri($C_{1-12}$ alkyl)silyl, $C_{1-12}$ alkoxyimino, $C_{1-12}$ alkylsulfinylimino, $C_{1-12}$ alkylsulfonylimino, $C_{1-12}$ alkoxy-carbonyl, $C_{1-12}$ alkylcarbonyl, aminocarbonyl, $C_{1-12}$ alkylamino-carbonyl, amino-thiocarbonyl, $C_{1-12}$ alkylamino-thiocarbonyl, $C_{2-24}$ (total carbon number) dialkylamino-carbonyl or $C_{2-24}$ (total carbon number) dialkylamino-thiocarbonyl, and herein, each group from $C_{1-12}$ alkyl to $C_{2-24}$ (total carbon number) dialkylamino-thiocarbonyl above may be optionally substituted, and $R^5$ represents a phenyl group which may be optionally substituted or a 5- to 6-membered heterocyclic group that contains at least one hetero atom optionally selected from the group consisting of N, O, and S, and may be optionally substituted.

2. The Aryl heterocycle derivative according to claim 1, in which

R' represents $C_{1-6}$ alkyl or $C_{1-6}$ haloalkyl, $A_1$, $A_2$, $A_3$ and $A_4$ each independently represent C—Y or N, $B_1$, $B_2$, $B_3$ and $B_4$ each independently represent C—X or N, X and Y each independently represent hydrogen, halogen, nitro, cyano, hydroxy, mercapto, amino, SF$_5$, $C_{1-6}$ alkyl, $C_{3-7}$ cycloalkyl, $C_{1-6}$ alkoxy, $C_{1-6}$ alkylthio, $C_{1-6}$ alkylsulfinyl, $C_{1-6}$ alkylsulfonyl, $C_{1-6}$ alkylsulfonyloxy, $C_{1-6}$ alkylaminosulfonyl, di($C_{1-6}$ alkyl)amino-sulfonyl, $C_{1-6}$ alkyl-carbonylamino, benzoylamino, tri($C_{1-6}$ alkyl)silyl, $C_{1-6}$ alkoxyimino, $C_{1-6}$ alkylsulfinylimino, $C_{1-6}$ alkylsulfonylimino, $C_{1-6}$ alkoxy-carbonyl, $C_{1-6}$ alkyl-carbonyl, aminocarbonyl, $C_{1-6}$ alkylamino-carbonyl, aminothiocarbonyl, $C_{1-6}$ alkylamino-thiocarbonyl, di($C_{1-6}$ alkyl)amino-carbonyl or di($C_{1-6}$ alkyl)amino-thiocarbonyl, and herein, each group from $C_{1-6}$ alkyl to di($C_{1-6}$ alkyl)amino-thiocarbonyl above may be optionally substituted with halogen, $R^1$ and $R^2$ each independently represent hydrogen, cyano, $C_{1-6}$ alkyl, $C_{3-7}$ cycloalkyl, $C_{3-7}$ cycloalkyl-$C_{1-6}$ alkyl, $C_{2-6}$ alkenyl, $C_{2-6}$ alkynyl, $C_{1-6}$ alkoxy-carbonyl or $C_{1-6}$ thioalkoxy-carbonyl, and herein, each group from $C_{1-6}$ alkyl to $C_{1-6}$ thioalkoxy-carbonyl above may be optionally substituted with halogen, or $R^1$ and $R^2$ may form, together with the carbon atom to which they are bound, a 3- to 6-membered hydrocarbon ring, or $R^1$ may form, together with Y of $A_2$, $C_{2-3}$ alkylene when n represents 1 and $A_2$ represents C—Y, $R^3$ represents hydrogen, amino, hydroxy, cyano, $C_{1-6}$ alkyl, $C_{1-6}$ alkoxy, $C_{1-6}$ alkyl-carbonylamino, $C_{1-6}$ alkylamino, $C_{3-7}$ cycloalkyl, $C_{2-6}$ alkenyl, $C_{2-6}$ alkynyl, $C_{1-6}$ alkyl-carbonyl, —CH$_2$—R$^5$, —C(=O)R$^5$ or C(=S)R$^5$, and herein, each group from $C_{1-6}$ alkyl to $C_{1-6}$ alkyl-carbonyl above may be optionally substituted with halogen, $R^4$ represents hydrogen, cyano, formyl, thioformyl, $C_{1-6}$ alkyl-carbonyl, $C_{1-6}$ alkyl-thiocarbonyl, $C_{1-6}$ alkylamino-carbonyl, $C_{1-6}$ alkylamino-thiocarbonyl, di($C_{1-6}$ alkyl) amino-carbonyl, di($C_{1-6}$ alkyl)amino-thiocarbonyl, $C_{1-6}$ alkoxyamino-carbonyl, $C_{1-6}$ alkoxyamino-thiocarbonyl, $C_{1-6}$ alkoxy-carbonyl, $C_{1-6}$ alkoxy-$C_{1-6}$ alkyl-carbonyl, $C_{1-6}$ thioalkoxy-$C_{1-6}$ alkyl-carbonyl, $C_{1-6}$ alkylsulfenyl-$C_{1-6}$ alkyl-carbonyl, $C_{1-6}$ alkylsulfonyl-$C_{1-6}$ alkyl-carbonyl, $C_{1-6}$ alkoxy-thiocarbonyl, $C_{1-6}$ thioalkoxy-carbonyl, $C_{1-6}$ thioalkoxy-thiocarbonyl, $C_{1-6}$ alkylsulfonyl, $C_{3-7}$ cycloalkyl-carbonyl, $C_{3-7}$ cycloalkyl-$C_{1-6}$ alkyl-carbonyl, $C_{2-6}$ alkenyl-carbonyl, $C_{2-6}$ alkynyl-carbonyl, $C_{3-7}$ cycloalkylamino-carbonyl, $C_{2-6}$ alkenylamino-carbonyl, $C_{2-6}$ alkynylamino-carbonyl, —C(=O)R$^5$ or C(=S)R$^5$, and herein, each group from $C_{1-6}$ alkyl-carbonyl to $C_{2-6}$ alkynylamino-carbonyl above may be optionally substituted with halogen, and $R^5$ represents a phenyl group which may be optionally substituted or a 5- to 6-membered heterocyclic group that contains at least one hetero atom optionally selected from the group consisting of N, O, and S, and may be optionally substituted.

3. The Aryl heterocycle derivative according to claim 1, in which

R' represents $C_{1-4}$ alkyl or $C_{1-4}$ haloalkyl, $A_1$, $A_2$, $A_3$ and $A_4$ each independently represent C—Y or N, $B_1$, $B_2$, $B_3$ and $B_4$ each independently represent C—X or N, X and Y each independently represent hydrogen, halogen, nitro, cyano, hydroxy, mercapto, amino, SF$_5$, $C_{1-4}$ alkyl, $C_{3-6}$ cycloalkyl, $C_{1-4}$ alkoxy, $C_{1-4}$ alkylthio, $C_{1-4}$ alkylsulfinyl, $C_{1-4}$ alkylsulfonyl, $C_{1-4}$ alkylsulfonyloxy, $C_{1-4}$ alkylaminosulfonyl, di($C_{1-4}$ alkyl)amino-sulfonyl, $C_{1-4}$ alkyl-carbonylamino, benzoylamino, tri($C_{1-4}$ alkyl)silyl, $C_{1-4}$ alkoxyimino, $C_{1-4}$ alkylsulfinylimino, $C_{1-4}$ alkylsulfonylimino, $C_{1-4}$ alkoxy-carbonyl, $C_{1-4}$ alkyl-carbonyl, aminocarbonyl, $C_{1-4}$ alkylamino-carbonyl, aminothiocarbonyl, $C_{1-4}$ alkylamino-thiocarbonyl, di($C_{1-4}$ alkyl)amino-carbonyl or di($C_{1-4}$ alkyl)amino-thiocarbonyl, and herein, each group from $C_{1-4}$ alkyl to di($C_{1-4}$ alkyl)amino-thiocarbonyl above may be optionally substituted with halogen, $R^1$ and $R^2$ each independently represent hydrogen, cyano, $C_{1-4}$ alkyl, $C_{3-6}$ cycloalkyl, $C_{3-6}$ cycloalkyl-$C_{1-4}$ alkyl, $C_{2-4}$ alkenyl, $C_{2-4}$ alkynyl, $C_{1-4}$ alkoxy-carbonyl or $C_{1-4}$ thioalkoxy-carbonyl, and herein, each group from $C_{1-4}$ alkyl to $C_{1-4}$ thioalkoxy-carbonyl above may be optionally substituted with halogen, or $R^1$ and $R^2$ may form, together with the carbon atom to which they are bound, a 3- to 6-membered hydrocarbon ring, or $R^1$ may form, together with Y of $A_2$, $C_{2-3}$ alkylene when n represents 1 and $A_2$ represents C—Y, $R^3$ represents hydrogen, amino, hydroxy, cyano, $C_{1-4}$ alkyl, $C_{1-4}$ alkoxy, $C_{1-4}$ alkyl-carbonylamino, $C_{1-4}$ alkylamino, $C_{3-6}$ cycloalkyl, $C_2$ alkenyl, $C_2$ alkynyl, $C_{1-4}$ alkyl-carbonyl, —$CH_2$—$R^5$, —C(=O)$R^5$ or C(=S)$R^5$, and herein, each group from $C_{1-4}$ alkyl to $C_{1-4}$ alkyl-carbonyl above may be optionally substituted with halogen, $R^4$ represents hydrogen, cyano, formyl, thioformyl, $C_{1-4}$ alkyl-carbonyl, $C_{1-4}$ alkyl-thiocarbonyl, $C_{1-4}$ alkylamino-carbonyl, $C_{1-4}$ alkylamino-thiocarbonyl, di($C_{1-4}$ alkyl) amino-carbonyl, di($C_{1-4}$ alkyl)amino-thiocarbonyl, $C_{1-4}$ alkoxyamino-carbonyl, $C_{1-4}$ alkoxyamino-thiocarbonyl, $C_{1-4}$ alkoxy-carbonyl, $C_{1-4}$ alkoxy-$C_{1-4}$ alkyl-carbonyl, $C_{1-4}$ thioalkoxy-$C_{1-4}$ alkyl-carbonyl, $C_{1-4}$ alkylsulfenyl-$C_{1-4}$ alkyl-carbonyl, $C_{1-4}$ alkylsulfonyl-$C_{1-4}$ alkyl-carbonyl, $C_{1-4}$ alkoxy-thiocarbonyl, $C_{1-4}$ thioalkoxy-carbonyl, $C_{1-4}$ thioalkoxy-thiocarbonyl, $C_{1-4}$ alkylsulfonyl, $C_{3-6}$ cycloalkyl-carbonyl, $C_{3-6}$ cycloalkyl-$C_{1-4}$ alkyl-carbonyl, $C_{2-4}$ alkenyl-carbonyl, $C_{2-4}$ alkynyl-carbonyl, $C_{3-6}$ cycloalkylamino-carbonyl, $C_{2-4}$ alkenylamino-carbonyl, $C_{2-4}$ alkynylamino-carbonyl, —C(=O)$R^5$ or C(=S)$R^5$, and herein, each group from $C_{1-4}$ alkyl-carbonyl to $C_{2-4}$ alkynylamino-carbonyl above may be optionally substituted with halogen, and $R^5$ represents a phenyl group which may be optionally substituted or a 5- to 6-membered heterocyclic group that contains at least one hetero atom optionally selected from the group consisting of N, O, and S, and may be optionally substituted.

4. A pesticide comprising as an effective component, an Aryl heterocycle derivative described in claim 1.

5. An agent for controlling an animal parasite comprising as an effective component, an Aryl heterocycle derivative described in claim 1.

6. A compound that is represented by Formula (II):

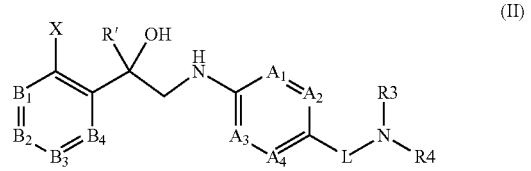

(II)

wherein R' represents $C_{1-12}$ alkyl or $C_{1-12}$ haloalkyl,
$A_1$, $A_2$, $A_3$ and $A_4$ each independently represent C—Y or N, with the proviso that two of $A_1$, $A_2$, $A_3$ and $A_4$ may simultaneously represent N, or two Ys may form, together with the carbon atom to which they are bound, a benzene ring or a 5- to 6-membered heteroaromatic ring when $A_1$ and $A_2$ represent C—Y, $B_1$, $B_2$, $B_3$ and $B_4$ each independently represent C—X or N,
L represents $(CR^1R^2)_n$,
n represents 1, 2 or 3, $R^1$ and $R^2$ each independently represent hydrogen, cyano, $C_{1-12}$ alkyl, $C_{3-8}$ cycloalkyl, $C_{3-8}$ cycloalkyl-$C_{1-12}$ alkyl, $C_{2-6}$ alkenyl, $C_{2-6}$ alkynyl, $C_{1-12}$ alkoxy-carbonyl or $C_{1-12}$ thioalkoxycarbonyl, and herein, each group from $C_{1-12}$ alkyl to $C_{1-12}$ thioalkoxy-carbonyl above may be optionally substituted with halogen, or $R^1$ and $R^2$ may form, together with the carbon atom to which they are bound, a 3- to 6-membered hydrocarbon ring, or $R^1$ may form, together with Y of $A_2$, $C_{2-3}$ alkylene when n represents 1 and $A_2$ represents C—Y, $R^3$ represents hydrogen, amino, hydroxy, cyano, $C_{1-12}$ alkyl, $C_{1-12}$ alkoxy, $C_{1-12}$ alkyl-carbonylamino, $C_{1-12}$ alkylamino, $C_{3-8}$ cycloalkyl, $C_{2-12}$ alkenyl, $C_{2-12}$ alkynyl, $C_{1-12}$ alkyl-carbonyl, —$CH_2$—$R^5$, —C(=O)$R^5$ or C(=S)$R^5$, and herein, each group from $C_{1-12}$ alkyl to $C_{1-12}$ alkyl-carbonyl above may be optionally substituted, $R^4$ represents hydrogen, cyano, formyl, thioformyl, $C_{1-12}$ alkyl-carbonyl, $C_{1-12}$ alkyl-thiocarbonyl, $C_{1-12}$ alkylamino-carbonyl, $C_{1-12}$ alkylamino-thiocarbonyl, $C_{2-24}$ (total carbon number) dialkylamino-carbonyl, $C_{2-24}$ (total carbon number) dialkylamino-thiocarbonyl, $C_{1-12}$ alkoxyamino-carbonyl, $C_{1-12}$ alkoxyamino-thiocarbonyl, $C_{1-12}$ alkoxy-carbonyl, $C_{1-12}$ alkoxy-$C_{1-12}$ alkyl-carbonyl, $C_{1-12}$ thioalkoxy-$C_{1-12}$ alkyl-carbonyl, $C_{1-12}$ alkylsulfenyl-$C_{1-12}$ alkyl-carbonyl, $C_{1-12}$ alkylsulfonyl-$C_{1-12}$ alkyl-carbonyl, $C_{1-12}$ alkoxy-thiocarbonyl, $C_{1-12}$ thioalkoxy-carbonyl, $C_{1-12}$ thioalkoxy-thiocarbonyl, $C_{1-12}$ alkylsulfonyl, $C_{3-8}$ cycloalkyl-carbonyl, $C_{3-8}$ cycloalkyl-$C_{1-12}$ alkyl-carbonyl, $C_{2-12}$ alkenyl-carbonyl, $C_{2-12}$ alkynyl-carbonyl, $C_{3-8}$ cycloalkylamino-carbonyl, $C_{2-12}$ alkenylamino-carbonyl, $C_{2-12}$ alkynylamino-carbonyl, —C(=O)$R^5$ or C(=S)$R^5$, and herein, each group from $C_{1-12}$ alkyl-carbonyl to $C_{2-12}$ alkynylamino-carbonyl above may be optionally substituted, or $R^3$ and $R^4$ may form, together with the nitrogen atom to which they are bound, a 3- to 6-membered heterocycle, and herein, the heterocycle may be optionally substituted with X, keto, thioketo, or nitroimino, X and Y, which may be the same or different from each other, represent hydrogen, halogen, nitro, cyano, hydroxy, mercapto, $SF_5$, amino, $C_{1-12}$ alkyl, $C_{3-8}$ cycloalkyl, $C_{1-12}$ alkoxy, $C_{1-12}$ alkylthio, $C_{1-12}$ alkylsulfinyl, $C_{1-12}$ alkylsulfonyl, $C_{1-12}$ alkylsulfonyloxy, $C_{1-12}$ alkylaminosulfonyl, $C_{2-24}$ (total carbon number) dialkylaminosulfonyl, $C_{1-12}$ alkylcarbonylamino, benzoylamino, tri($C_{1-12}$ alkyl)silyl, $C_{1-12}$ alkoxyimino, $C_{1-12}$ alkylsulfinylimino, $C_{1-12}$ alkylsulfonylimino, $C_{1-12}$ alkoxy-carbonyl, $C_{1-12}$ alkylcarbonyl, aminocarbonyl, $C_{1-12}$ alkylamino-carbonyl, amino-thiocarbonyl, $C_{1-12}$ alkylamino-thiocarbonyl, $C_{2-24}$ (total carbon number) dialkylamino-carbonyl or $C_{2-24}$ (total carbon number) dialkylamino-thiocarbonyl, and herein, each group from $C_{1-12}$ alkyl to $C_{2-24}$ (total carbon number) dialkylamino-thiocarbonyl above may be optionally substituted, and $R^5$ represents a phenyl group which may be optionally substituted or a 5- to 6-membered heterocyclic group that contains at least one hetero atom optionally selected from the group consisting of N, O, and S, and may be optionally substituted.

7. A compound that is represented by Formula (III):

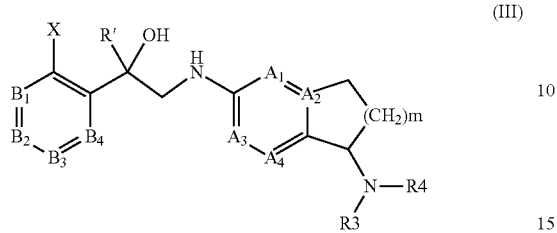

(III)

wherein R' represents $C_{1-12}$ alkyl or $C_{1-12}$ haloalkyl, $A_1$, $A_3$ and $A_4$ each independently represent C—Y or N, with the proviso that two of $A_1$, $A_3$ and $A_4$ may simultaneously represent N, $B_1$, $B_2$, $B_3$ and $B_4$ each independently represent C—X or N, m represents 1 or 2, $R^3$ represents hydrogen, amino, hydroxy, cyano, $C_{1-12}$ alkyl, $C_{1-12}$ alkoxy, $C_{1-12}$ alkyl-carbonylamino, $C_{1-12}$ alkylamino, $C_{3-8}$ cycloalkyl, $C_{2-12}$ alkenyl, $C_{2-12}$ alkynyl, $C_{1-12}$ alkyl-carbonyl, —CH$_2$—R$^5$, —C(=O)R$^5$ or C(=S)R$^5$, and herein, each group from $C_{1-12}$ alkyl to $C_{1-12}$ alkyl-carbonyl above may be optionally substituted, $R^4$ represents hydrogen, cyano, formyl, thioformyl, $C_{1-12}$ alkyl-carbonyl, $C_{1-12}$ alkyl-thiocarbonyl, $C_{1-12}$ alkylamino-carbonyl, $C_{1-12}$ alkylamino-thiocarbonyl, $C_{2-24}$ (total carbon number) dialkylamino-carbonyl, $C_{2-24}$ (total carbon number) dialkylamino-thiocarbonyl, $C_{1-12}$ alkoxyamino-carbonyl, $C_{1-12}$ alkoxyamino-thiocarbonyl, $C_{1-12}$ alkoxy-carbonyl, $C_{1-12}$ alkoxy-$C_{1-12}$ alkyl-carbonyl, $C_{1-12}$ thioalkoxy-$C_{1-12}$ alkyl-carbonyl, $C_{1-12}$ alkylsulfenyl-$C_{1-12}$ alkyl-carbonyl, $C_{1-12}$ alkylsulfonyl-$C_{1-12}$ alkyl-carbonyl, $C_{1-12}$ alkoxy-thiocarbonyl, $C_{1-12}$ thioalkoxy-carbonyl, $C_{1-12}$ thioalkoxy-thiocarbonyl, $C_{1-12}$ alkylsulfonyl, $C_{3-8}$ cycloalkyl-carbonyl, $C_{3-8}$ cycloalkyl-$C_{1-12}$ alkyl-carbonyl, $C_{2-12}$ alkenyl-carbonyl, $C_{2-12}$ alkynyl-carbonyl, $C_{3-8}$ cycloalkylamino-carbonyl, $C_{2-12}$ alkenylamino-carbonyl, $C_{2-12}$ alkynylamino-carbonyl, —C(=O)R$^5$ or C(=S)R$^5$, and herein, each group from $C_{1-12}$ alkyl-carbonyl to $C_{2-12}$ alkynylamino-carbonyl above may be optionally substituted, or $R^3$ and $R^4$ may form, together with the nitrogen atom to which they are bound, a 3- to 6-membered heterocycle, and herein, the heterocycle may be optionally substituted with X, keto, thioketo, or nitroimino, X and Y, which may be the same or different from each other, represent hydrogen, halogen, nitro, cyano, hydroxy, mercapto, SF$_5$, amino, $C_{1-12}$ alkyl, $C_{3-8}$ cycloalkyl, $C_{1-12}$ alkoxy, $C_{1-12}$ alkylthio, $C_{1-12}$ alkylsulfinyl, $C_{1-12}$ alkylsulfonyl, $C_{1-12}$ alkylsulfonyloxy, $C_{1-12}$ alkylaminosulfonyl, $C_{2-24}$ (total carbon number) dialkylaminosulfonyl, $C_{1-12}$ alkylcarbonylamino, benzoylamino, tri($C_{1-12}$ alkyl)silyl, $C_{1-12}$ alkoxyimino, $C_{1-12}$ alkylsulfinylimino, $C_{1-12}$ alkylsulfonylimino, $C_{1-12}$ alkoxy-carbonyl, $C_{1-12}$ alkylcarbonyl, aminocarbonyl, $C_{1-12}$ alkylamino-carbonyl, amino-thiocarbonyl, $C_{1-12}$ alkylamino-thiocarbonyl, $C_{2-24}$ (total carbon number) dialkylamino-carbonyl or $C_{2-24}$ (total carbon number) dialkylamino-thiocarbonyl, and herein, each group from $C_{1-12}$ alkyl to $C_{2-24}$ (total carbon number) dialkylamino-thiocarbonyl above may be optionally substituted, and $R^5$ represents a phenyl group which may be optionally substituted or a 5- to 6-membered heterocyclic group that contains at least one hetero atom optionally selected from the group consisting of N, O, and S, and may be optionally substituted.

8. A compound that is represented by Formula (IV):

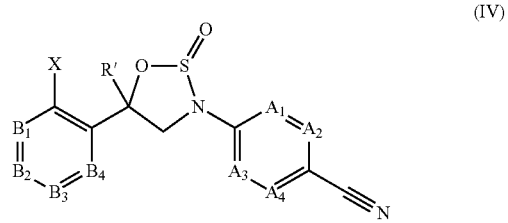

(IV)

wherein R' represents $C_{1-12}$ alkyl or $C_{1-12}$ haloalkyl, $A_1$, $A_2$, $A_3$ and $A_4$ each independently represent C—Y or N, with the proviso that two of $A_1$, $A_2$, $A_3$ and $A_4$ may simultaneously represent N, or two Ys may form, together with the carbon atom to which they are bound, a benzene ring or a 5- to 6-membered heteroaromatic ring when $A_1$ and $A_2$ represent C—Y, $B_1$, $B_2$, $B_3$ and $B_4$ each independently represent C—X or N, X and Y, which may be the same or different from each other, represent hydrogen, halogen, nitro, cyano, hydroxy, mercapto, SF$_5$, amino, $C_{1-12}$ alkyl, $C_{3-8}$ cycloalkyl, $C_{1-12}$ alkoxy, $C_{1-12}$ alkylthio, $C_{1-12}$ alkylsulfinyl, $C_{1-12}$ alkylsulfonyl, $C_{1-12}$ alkylsulfonyloxy, $C_{1-12}$ alkylaminosulfonyl, $C_{2-24}$ (total carbon number) dialkylaminosulfonyl, $C_{1-12}$ alkylcarbonylamino, benzoylamino, tri($C_{1-12}$ alkyl)silyl, $C_{1-12}$ alkoxyimino, $C_{1-12}$ alkylsulfinylimino, $C_{1-12}$ alkylsulfonylimino, $C_{1-12}$ alkoxy-carbonyl, $C_{1-12}$ alkylcarbonyl, aminocarbonyl, $C_{1-12}$ alkylamino-carbonyl, amino-thiocarbonyl, $C_{1-12}$ alkylamino-thiocarbonyl, $C_{2-24}$ (total carbon number) dialkylamino-carbonyl or $C_{2-24}$ (total carbon number) dialkylamino-thiocarbonyl, and herein, each group from $C_{1-12}$ alkyl to $C_{2-24}$ (total carbon number) dialkylamino-thiocarbonyl may be substituted.

9. A compound that is represented by Formula (V):

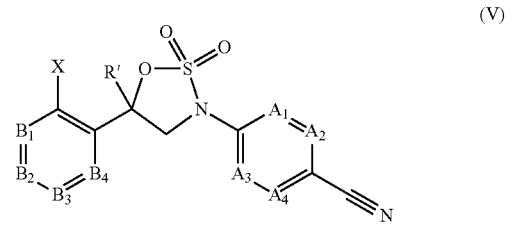

(V)

wherein R' represents $C_{1-12}$ alkyl or $C_{1-12}$ haloalkyl, $A_1$, $A_2$, $A_3$ and $A_4$ each independently represent C—Y or N, with the proviso that two of $A_1$, $A_2$, $A_3$ and $A_4$ may simultaneously represent N, or two Ys may form, together with the carbon atom to which they are bound, a benzene ring or a 5- to 6-membered heteroaromatic ring when $A_1$ and $A_2$ represent C—Y, $B_1$, $B_2$, $B_3$ and $B_4$ each independently represent C—X or N, X and Y, which may be the same or different from each other, represent hydrogen, halogen, nitro, cyano, hydroxy, mercapto, SF$_5$, amino, $C_{1-12}$ alkyl, $C_{3-8}$ cycloalkyl, $C_{1-12}$ alkoxy, $C_{1-12}$ alkylthio, $C_{1-12}$ alkylsulfinyl, $C_{1-12}$ alkylsulfonyl, $C_{1-12}$ alkylsulfonyloxy, $C_{1-12}$ alkylaminosulfonyl, $C_{2-24}$ (total carbon number) dialkylaminosulfonyl, $C_{1-12}$ alkylcarbonylamino, benzoylamino, tri($C_{1-12}$ alkyl)silyl, $C_{1-12}$ alkoxyimino, $C_{1-12}$ alkylsulfinylimino, $C_{1-12}$ alkylsulfonylimino, $C_{1-12}$ alkoxy-carbonyl, $C_{1-12}$ alkylcarbonyl, aminocarbonyl, $C_{1-12}$ alkylamino-carbonyl, amino-thiocarbonyl, $C_{1-12}$ alkylamino-thiocarbonyl, $C_{2-24}$ (total carbon number) dialkylamino-carbonyl or $C_{2-24}$ (total carbon number) dialkylamino-thiocarbonyl, and herein, each group from $C_{1-12}$ alkyl to $C_{2-24}$ (total carbon number) dialkylamino-thiocarbonyl may be substituted.

10. A compound that is represented by Formula (VI):

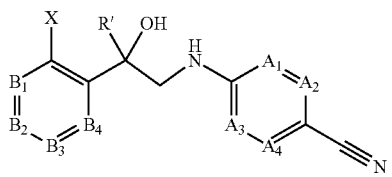

(VI)

wherein R' represents $C_{1-12}$ alkyl or $C_{1-12}$ haloalkyl, $A_1$, $A_2$, $A_3$ and $A_4$ each independently represent C—Y or N, with the proviso that two of $A_1$, $A_2$, $A_3$ and $A_4$ may simultaneously represent N, or two Ys may form, together with the carbon atom to which they are bound, a benzene ring or a 5- to 6-membered heteroaromatic ring when $A_1$ and $A_2$ represent C—Y, $B_1$, $B_2$, $B_3$ and $B_4$ each independently represent C—X or N, X and Y, which may be the same or different from each other, represent hydrogen, halogen, nitro, cyano, hydroxy, mercapto, $SF_5$, amino, $C_{1-12}$ alkyl, $C_{3-8}$ cycloalkyl, $C_{1-12}$ alkoxy, $C_{1-12}$ alkylthio, $C_{1-12}$ alkylsulfinyl, $C_{1-12}$ alkylsulfonyl, $C_{1-12}$ alkylsulfonyloxy, $C_{1-12}$ alkylaminosulfonyl, $C_{2-24}$ (total carbon number) dialkylaminosulfonyl, $C_{1-12}$ alkylcarbonylamino, benzoylamino, tri($C_{1-12}$ alkyl)silyl, $C_{1-12}$ alkoxyimino, $C_{1-12}$ alkylsulfinylimino, $C_{1-12}$ alkylsulfonylimino, $C_{1-12}$ alkoxy-carbonyl, $C_{1-12}$ alkylcarbonyl, aminocarbonyl, $C_{1-12}$ alkylamino-carbonyl, amino-thiocarbonyl, $C_{1-12}$ alkylamino-thiocarbonyl, $C_{2-24}$ (total carbon number) dialkylamino-carbonyl or $C_{2-24}$ (total carbon number) dialkylamino-thiocarbonyl, and herein, each group from $C_{1-12}$ alkyl to $C_{2-24}$ (total carbon number) dialkylamino-thiocarbonyl may be substituted.

11. The compound of claim 10, wherein R' represents $C_{1-12}$ haloalkyl.

* * * * *